United States Patent
Iwabuchi et al.

(10) Patent No.: US 6,734,181 B2
(45) Date of Patent: May 11, 2004

(54) PYRROLOPYRIDAZINE COMPOUNDS

(75) Inventors: Haruo Iwabuchi, Urawa (JP); Masahiko Hagihara, Ube (JP); Nobuhiko Shibakawa, Ube (JP); Keiji Matsunobu, Ube (JP); Hiroshi Fujiwara, Ube (JP)

(73) Assignees: Sankyo Company, Limited, Tokyo (JP); Ube Industries, Ltd., Ube (JP)

( * ) Notice: Subject to any disclaimer, the term of this patent is extended or adjusted under 35 U.S.C. 154(b) by 0 days.

(21) Appl. No.: 10/215,246

(22) Filed: Aug. 8, 2002

(65) Prior Publication Data

US 2004/0014762 A1 Jan. 22, 2004

Related U.S. Application Data

(63) Continuation of application No. PCT/JP01/00820, filed on Feb. 6, 2001.

(30) Foreign Application Priority Data

Feb. 10, 2000 (JP) .......................... 2000-033627

(51) Int. Cl.$^7$ .................. A61K 31/5025; C07D 487/04
(52) U.S. Cl. .......................... 514/248; 544/236
(58) Field of Search ............... 544/236; 514/248

(56) References Cited

U.S. PATENT DOCUMENTS

| | | |
|---|---|---|
| 5,534,515 A | 7/1996 | Grundler |
| 5,753,664 A | 5/1998 | Aono et al. |
| 6,063,782 A | 5/2000 | Kimura et al. |
| 2002/0156079 A1 | 10/2002 | Hagihara et al. |

FOREIGN PATENT DOCUMENTS

| | | |
|---|---|---|
| EP | 1 186 607 A1 | 3/2002 |
| WO | WO 91/17164 A1 | 11/1991 |
| WO | WO 92/06979 A1 | 4/1992 |
| WO | WO 00/77003 A1 | 12/2000 |

OTHER PUBLICATIONS

U.S. patent application Ser. No. 10/021,214, Hagihara et al., not yet published.
English language translation of the International Preliminary Examination Report PCT/IPEA/409 in the parent International Application PCT/JP01/00820 (date of completion of Report: Jan. 17, 2002).

*Primary Examiner*—Emily Bernhardt
*Assistant Examiner*—Camelia Styles
(74) *Attorney, Agent, or Firm*—Frishauf, Holtz, Goodman & Chick, P.C.

(57) ABSTRACT

A pyrrolopyridazine compound having the formula (I) or a pharmaceutically acceptable salt thereof:

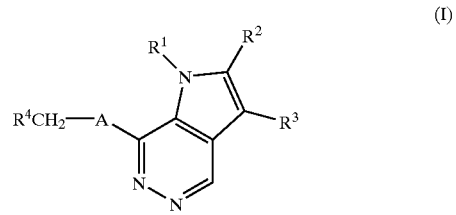

wherein, $R^1$ is a $C_2$–$C_6$ alkenyl group, a halogeno $C_2$–$C_6$ alkenyl group, a $C_3$–$C_7$ cycloalkyl group which may be optionally substituted or a $C_3$–$C_7$ cycloalkyl- $C_1$–$C_6$ alkyl group which may be optionally substituted. $R^2$ is a $C_1$–$C_6$ alkyl group. $R^3$ is a hydroxymethyl group, a $C_2$–$C_6$ aliphatic acyloxymethyl group, a $C_6$–$C_{10}$ arylcarbonyloxymethyl group which may be optionally substituted, a $C_1$–$C_6$ alkoxycarbonyloxymethyl group, a formyl group, a carboxyl group, a $C_1$–$C_6$ alkoxycarbonyl group or a $C_6$–$C_{10}$ aryloxycarbonyl group which may be optionally substituted. $R^4$ is a $C_6$–$C_{10}$ aryl group which may be optionally substituted. A is an imino group, an oxygen atom or a sulfur atom. These compounds exhibit excellent gastric acid secretory inhibition activity and gastric mucous membrane protection activity etc. They are useful for prevention or treatment of ulcerative diseases and for *Helicobacter pylori* infections.

40 Claims, No Drawings

PYRROLOPYRIDAZINE COMPOUNDS

This is a continuation application of international application PCT/JP01/00820 filed Feb. 6, 2001.

TECHNICAL FIELD

This invention relates to pyrrolopyridazine derivatives or pharmaceutically acceptable salts thereof; to pharmaceutical compositions comprising a pyrrolopyridazine derivative or a pharmaceutically acceptable salt thereof (preferably compositions for the prevention or treatment of ulcerative disease) as an active ingredient; to the use of a pyrrolopyridazine derivative or a pharmaceutically acceptable salt thereof in the preparation of a pharmaceutical composition (preferably a composition for the prevention or treatment of ulcerative disease); or to a method for the prevention or treatment of disease (preferably ulcerative disease), which method comprises administering a pharmaceutically effective amount of a pyrrolopyridazine derivative or a pharmaceutically acceptable salt thereof to a warm-blooded animal (preferably a human).

BACKGROUND OF THE INVENTION

It has been considered that an imbalance between aggressive factors and protective factors against the gastric mucous membrane induces peptic ulcers. Gastric acid secretion is an aggressive factor and suppression of gastric acid secretion is useful in the prevention and treatment of the disease. Anticholinergic agents, histamine $H_2$ receptor antagonists such as cimetidine and the like and proton pump inhibitors such as omeprazole and the like have been clinically used as a gastric acid secretion inhibitor. Although these agents are excellent therapeutic agents for ulcerative disease, the disease may recur after cessation of the therapy. It has been recently reported that *Helicobacter pylon* relates to recurrence of the ulcerative disease. Actually there have been some attempts to use a gastric acid secretion inhibitor in combination with an antibacterial agent for treatment of the disease.

Accordingly a compound that exhibits potent gastric acid secretory inhibition activity, excellent gastric mucous membrane protection activity and potent antibacterial activity against *Helicobacter pylori* would be expected to be an excellent medicament (preferably a prophylactic and therapeutic agent for ulcerative disease).

Some pyrrolopyridazine derivatives that have gastric acid secretory inhibition activity and gastric mucous membrane protection activity have been known (for example, WO 91/17164, WO 92/06979, WO 93/08190 and the like). The activity against *Helicobacter pylori* of some pyrrolopyridazine derivatives has also been known (for example, Japanese Patent Application Publication Hei 7-247285 and the like).

DISCLOSURE OF THE INVENTION

The inventors have continued an investigation on the pharmacological activities of pyrrolopyridazine derivatives in order to discover a medicament (preferably an agent for ulcerative disease) that exhibits potent gastric acid secretory inhibition activity, protects gastric mucous membranes and has excellent antibacterial activity against *Helicobacter pylori* for a long time. As a result, they found that some pyrrolopyridazine derivatives substituted with specific substituents at the 3-position exhibit potent gastric acid secretory inhibition activity and gastric mucous membrane protection activity and exhibit excellent antibacterial activity against *Helicobacter pylori*.

The pyrrolopyridazine derivative, i.e., compound, of the present invention has the following formula:

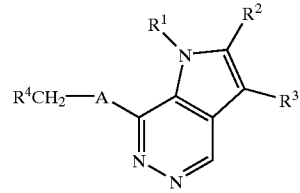

(I)

wherein:
$R^1$ represents a $C_2$–$C_6$ alkenyl group, a halogeno $C_2$–$C_6$ alkenyl group, a $C_3$–$C_7$ cycloalkyl group which may be optionally substituted with $C_1$–$C_6$ alkyl or a $C_3$–$C_7$ cycloalkyl-$C_1$–$C_6$ alkyl group which may be optionally substituted with $C_1$–$C_6$ alkyl; $R^2$ represents a $C_1$–$C_6$ alkyl group;

$R^3$ represents a hydroxymethyl group, a $C_2$–$C_6$ aliphatic acyloxymethyl group, a $C_6$–$C_{10}$ arylcarbonyloxymethyl group which may be optionally substituted with substituents selected from the group consisting of $C_1$–$C_6$ alkyl, $C_1$–$C_6$ alkoxy and halogeno, a $C_1$–$C_6$ alkoxycarbonyloxymethyl group, a formyl group, a carboxyl group, a $C_1$–$C_6$ alkoxycarbonyl group or a $C_6$–$C_{10}$ aryloxycarbonyl group which may be optionally substituted with substituents selected from the group consisting of $C_1$–$C_6$ alkyl, $C_1$–$C_6$ alkoxy and halogeno;

$R^4$ represents a $C_6$–$C_{10}$ aryl group which may be optionally substituted with substituents selected from the group consisting of $C_1$–$C_6$ alkyl, halogeno $C_1$–$C_6$ alkyl, $C_1$–$C_6$ alkoxy, halogeno $C_1$–$C_6$ alkoxy and halogeno;

A represents an imino group, an oxygen atom or a sulfur atom;

In the formula (I) described above:
The $C_1$–$C_6$ alkyl group in the definition of $R^2$ or the $C_1$–$C_6$ alkyl moiety included in the definition of $R^1$, $R^3$ or $R^4$ is, for example, a methyl, ethyl, propyl, isopropyl, butyl, isobutyl, s-butyl t-butyl, pentyl or hexyl group; preferably a $C_1$–$C_4$ alkyl group; more preferably a methyl or ethyl group; and most preferably a methyl group.

The $C_2$–$C_6$ alkenyl group or $C_2$–$C_6$ alkenyl moiety of the halogeno $C_2$–$C_6$ alkenyl group in the definition of $R^1$ is, for example, a vinyl, 1-propenyl, 2-propenyl, isopropenyl, 1-butenyl, 2-butenyl, 1-methyl-1-propenyl, 1-methyl-2-propenyl, 2-methyl-1-propenyl, 2-methyl-2-propenyl, 2-pentenyl or 2-hexenyl group; preferably a $C_2$–$C_4$ alkenyl group, more preferably a $C_3$–$C_4$ alkenyl group; still more preferably a 2-propenyl or 2-butenyl group; and most preferably a 2-butenyl group.

A typical example of a halogeno $C_2$–$C_6$ alkenyl group in the definition of $R^1$ is, for example, a 2,2-difluorovinyl, 3-fluoro-2-propenyl, 3-chloro-2-propenyl, 3-bromo-2-propenyl, 3-iodo-2-propenyl, 3,3-difluoro-2-propenyl, 2,3-dichloro-2-propenyl, 3,3-dichloro-2-propenyl, 2,3-dibromo-2-propenyl, 3,3-dibromo-2-propenyl, 4,4,4-trifluoro-2-butenyl, 5-fluoro-2-pentenyl or 6-fluoro-2-hexenyl group; preferably a 3-chloro-2-propenyl, 3,3-difluoro-2-propenyl, 3,3-dichloro-2-propenyl or 4,4,4-trifluoro-2-butenyl group; and more preferably a 3-chloro-2-propenyl, 3,3-difluoro-2-propenyl or 3,3-dichloro-2-propenyl group.

The $C_3$–$C_7$ cycloalkyl moiety of the $C_3$–$C_7$ cycloalkyl group which may be optionally substituted with a $C_1$–$C_6$ alkyl group or of the $C_3$–$C_7$ cycloalkyl-$C_1$–$C_6$ alkyl group which may be optionally substituted with a $C_1$–$C_6$ alkyl group in the definition of $R^1$ is, for example, a cyclopropyl, cyclobutyl, cyclopentyl, cyclohexyl or cycloheptyl group; preferably a $C_3$–$C_6$ cycloalkyl group; more preferably a cyclopropyl, cyclopentyl or cyclohexyl group; and most preferably a cyclopropyl group.

A typical example of the $C_3$–$C_7$ cycloalkyl group which may be optionally substituted with a $C_1$–$C_6$ alkyl group in the definition of $R^1$ is, for example, a cyclopropyl, 2-ethylcyclopropyl, 2-thylcyclopropyl, 2-ropylcyclopropyl, 2-exylcyclopropyl, cyclobutyl, 2-methylcyclobutyl, cyclopentyl, 2-methylcyclopentyl, 2-ethylcyclopentyl, cyclohexyl, 2-methylcyclohexyl or cycloheptyl group; preferably a cyclopropyl, 2-methylcyclopropyl, 2-ethylcyclopropyl, cyclobutyl, cyclopentyl, 2-methylcyclopentyl, cyclohexyl or 2-methylcyclohexyl group; more preferably a cyclopropyl, 2-methylcyclopropyl, cyclopentyl, 2-methylcyclopentyl, cyclohexy or 2-methylcyclohexyl group; and most preferably a cyclopropyl or 2-methylcyclopropyl group.

A typical example of the $C_3$–$C_7$ cycloalkyl-$C_1$–$C_6$ alkyl group which may be optionally substituted with a $C_1$–$C_6$ alkyl group in the definition of $R^1$ is, for example, a cyclopropylmethyl, 2-cyclopropylethyl, 2-methylcyclopropylmethyl, 2-(2-methylcyclopropyl)ethyl, 3-(2-methylcyclopropyl)propyl, 6-(2-methylcyclopropyl)hexyl, 2-ethylcyclopropylmethyl, 2-propylcyclopropylmethyl, 2-hexylcyclopropylmethyl, cyclobutylmethyl, 2-methylcyclobutylmethyl, cyclopentylmethyl, 2-cyclopentylethyl, 2-methylcyclopentylmethyl, 2-(2-methylcyclopentyl)ethyl, 2-ethylcyclopentylmethyl, cyclohexylmethyl, 2-cyclohexylethyl, 2-methylcyclohexylmethyl, 2-(2-methylcyclohexyl)ethyl or cycloheptylmethyl group; preferably a cyclopropylmethyl, 2-cyclopropylethyl, 2-methylcyclopropylmethyl, 2-(2-methylcyclopropyl)ethyl, 2-ethylcyclopropylmethyl, cyclobutylmethyl, 2-methylcyclobutylmethyl, cyclopentylmethyl, 2-methylcyclopentylmethyl, cyclohexylmethyl or 2-methylcyclohexylmethyl group; more preferably a cyclopropylmethyl, 2-methylcyclopropylmethyl, 2-ethylcyclopropylmethyl, cyclobutylmethyl, 2-methylcyclobutylmethyl, cyclopentylmethyl or 2-methylcyclohexylmethyl group; more preferably a cyclopropylmethyl, 2-methylcyclopropylmethyl, cyclopentylmethyl or 2-methylcyclohexylmethyl group; still more preferably a cyclopropylmethyl or 2-methylcyclopropylmethyl group; and most preferably a 2-methylcyclopropylmethyl group.

The $C_2$–$C_6$ aliphatic acyl moiety of the $C_2$–$C_6$ aliphatic acyloxymethyl group in the definition of $R^3$ is, for example, an acetyl, propionyl, butyryl, isobutyryl, valeryl, isovaleryl or hexanoyl group; preferably a $C_2$–$C_4$ aliphatic acyl group; more preferably a $C_2$–$C_3$ aliphatic acyl group; and most preferably an acetyl group.

The $C_1$–$C_6$ alkoxy moiety of a substituent of the aryl group or a $C_1$–$C_6$ alkoxy moiety of the halogeno $C_1$–$C_6$ alkoxy group of a substituent of the aryl group in the definition of $R^3$ and $R^4$ or the $C_1$–$C_6$ alkoxy moiety of the $C_1$–$C_6$ alkoxycarbonyloxymethyl group and the $C_1$–$C_6$ alkoxycarbonyl group in the definition of $R^3$ is, for example, a methoxy, ethoxy, propoxy, isopropoxy, butoxy, isobutoxy, s-butoxy, t-butoxy, pentyloxy or hexyloxy group; preferably a $C_1$–$C_4$ alkoxy group; more preferably a methoxy or ethoxy group; and most preferably a methoxy group.

The halogen atom included in the definition of $R^1$, $R^3$ and $R^4$ is, for example, a fluorine, chlorine, bromine or iodine atom; preferably a fluorine, chlorine or bromine atom; more preferably a fluorine or chlorine atom.

The $C_6$–$C_{10}$ aryl moiety of the optionally substituted $C_6$–$C_{10}$ aryl moiety in the definition of $R^3$ or of the optionally substituted $C_6$–$C_{10}$ aryl group in the definition of $R^4$ is, for example, a phenyl or naphthyl group; preferably a phenyl group.

The number of the substitutents on the aryl group is, for example from 1 to 5; preferably from 1 to 3; more preferably 1 or 2; and most preferably one.

The preferred $C_6$–$C_{10}$ aryl moiety which may be optionally substituted with substituents selected from the group consisting of $C_1$–$C_6$ alkyl, $C_1$–$C_6$ alkoxy and halogeno in the definition of $R^3$ is, for example, a phenyl, methylphenyl, dimethylphenyl, methoxyphenyl, dimethoxyphenyl, fluorophenyl, chlorophenyl, bromophenyl, difluorophenyl, chlorofluorophenyl, dichlorophenyl, naphthyl, methylnaphtyl, methoxynaphthyl, fluoronaphthyl, chloronaphthyl or bromonaphthyl group; more preferably a phenyl, methylphenyl, methoxyphenyl, fluorophenyl or chlorophenyl group; most preferably a phenyl or methylphenyl group.

The preferred $C_6$–$C_{10}$ aryl group which may be optionally substituted with substituents selected from the group consisting of $C_1$–$C_6$ alkyl, halogeno $C_1$–$C_6$ alkyl, $C_1$–$C_6$ alkoxy, halogeno $C_1$–$C_6$ alkoxy, and halogeno in the definition of $R^4$ is, for example, a phenyl, methylphenyl, trifluoromethylphenyl, methoxyphenyl, trifluoromethoxyphenyl, difluoromethoxyphenyl, fluorophenyl, chlorophenyl, bromophenyl, difluorophenyl, chlorofluorophenyl, dichlorophenyl, trifluorophenyl, trichlorophenyl, naphthyl, methylnaphtyl, methoxynaphthyl, fluoronaphthyl, chloronaphthyl or bromonaphthyl group; more preferably a phenyl, 4-methylphenyl, 4-trifluoromethylphenyl, 4-methoxyphenyl, 4-trifluoromethoxyphenyl, 4-difluoromethoxyphenyl, 2-, 3- or 4-fluorophenyl, 2-, 3- or 4-chlorophenyl, 4-bromophenyl, 2,4- or 2,6-difluorophenyl, 4-cloro-2-fluorophenyl, 2-chloro-4-fluorophenyl, 2,4- or 2,6-dichlorophenyl, 2,4,6-trifluorophenyl or 2,4,6-trichlorophenyl group; still more preferably a 4-fluorophenyl, 4-chlorophenyl, 2,4-difluorophenyl, 2,6-difluorophenyl, 4chloro-2-fluorophenyl, 2-chloro-4-fluorophenyl, 2,4-dichlorophenyl or 2,6-dichlorophenyl group; and most preferably a 4-fluorophenyl, 2,4-difluorophenyl or 4-chlorophenyl group.

The preferred group A is an oxygen atom or a sulfur atom; more preferably an oxygen atom.

The compound of formula (I) in this invention can exist as an optical isomer due to an asymmetric carbon atom(s) or as a geometrical isomer due to a double bond(s) or to ring structure. The present invention encompasses a single isomer and mixtures of such isomers.

The pharmaceutically acceptable salts of compounds of formula (I) are acid addition salts. Examples of such salt are, for example, a hydrohalogenic acid salt such as hydrofluoride, hydrochloride, hydrobromide, hydroiodide; a nitrate; a perchlorate; a sulfate; a phosphate; a carbonate; a $C_1$–$C_6$ alkylsulfonate which may be optionally substituted with fluorine atoms, such as methanesulfonate, trifluoromethanesulfonate, ethanesulfonate, pentafluoroethanesulfonate, propanesulfonate, butanesulfonate, pentanesulfonate, hexanesulfonate; a $C_6$–$C_{10}$ arylsulfonate such as benzenesulfonate, p-toluenesulfonate; a carboxylate such as acetate, propionate, lactate, benzoate, fumarate, maleate, succinate, citrate, tartrate, oxalate, malonate; or an amino acid salt such as glutamate or aspartate; preferably a hydrochloride, sulfate or carboxylate and most preferably a hydrochloride.

The compounds of formula (I) in this invention or salts thereof can exist as hydrates. The present invention encompasses such hydrates.

Preferred compounds of formula (I) are:

(1) a compound wherein $R^1$ is a $C_2$–$C_4$ alkenyl group, a $C_3$–$C_4$ alkenyl group substituted with fluoro or chloro, a $C_3$–$C_6$ cycloalkyl group which may be optionally substituted with $C_1$–$C_2$ alkyl or a $C_3$–$C_6$ cycloalkyl-$C_1$–$C_2$ alkyl group which may be substituted with $C_1$–$C_2$ alkyl;

(2) a compound wherein $R^1$ is a $C_3$–$C_4$ alkenyl group, a 3-chloro-2-propenyl group, a 3,3-difluoro-2-propenyl group, a 3,3-dichloro-2-propenyl group, a cyclopropyl group, a 2-methylcyclopropyl group, a 2-ethylcyclopropyl group, a cyclobutyl group, a cyclopentyl group, a 2-methylcyclopentyl group, a cyclohexyl group, a 2-methylcyclohexyl group, a cyclopropylmethyl group, a 2-methylcyclopropylmethyl group, a 2-ethylcyclopropylmethyl group, a cyclobutylmethyl group, a 2-methylcyclobutylmethyl group, a cyclopentylmethyl group or a 2-methylcyclohexylmethyl group;

(3) a compound wherein $R^1$ is a 2-propenyl group, a 2-butenyl group, a cyclopropyl group, a 2-methylcyclopropyl group, a cyclopentyl group, a 2-methylcyclopentyl group, a cyclohexyl group, a 2-methylcyclohexyl group, a cyclopropylmethyl group, a 2-methylcyclopropylmethyl group, a cyclopentylmethyl group or a 2-methylcyclohexylmethyl group;

(4) a compound wherein $R^1$ is a 2-propenyl group, a 2-butenyl group, a cyclopropyl group, a 2-methylcyclopropyl group, a cyclopropylmethyl group or a 2-methylcyclopropylmethyl group;

(5) a compound wherein $R^1$ is a 2-butenyl group, a cyclopropylmethyl group or a 2-methylcyclopropylmethyl group;

(6) a compound wherein $R^2$ is a $C_1$–$C_4$ alkyl group;
(7) a compound wherein $R^2$ is a $C_1$–$C_2$ alkyl group;
(8) a compound wherein $R^2$ is a methyl group;

(9) a compound wherein $R^3$ is a hydroxymethyl group, a $C_2$–$C_6$ aliphatic acyloxymethyl group, a benzoyloxymethyl group which may be optionally substituted with methyl, methoxy, fluoro or chloro, a $C_1$–$C_4$ alkoxycarbonyloxymethyl group, a formyl group, a carboxyl group, a $C_1$–$C_4$ alkoxycarbonyl group or a phenyloxycarbonyl group which may be optionally substituted with methyl, methoxy, fluoro or chloro;

(10) a compound wherein $R^3$ is a hydroxymethyl group, a $C_2$–$C_6$ aliphatic acyloxymethyl group, a benzoyloxymethyl group, a $C_1$–$C_2$ alkoxycarbonyloxymethyl group, a formyl group, a carboxyl group, a $C_1$–$C_2$ alkoxycarbonyl group or a phenyloxycarbonyl group;

(11) a compound wherein $R^3$ is a hydroxymethyl group, a $C_2$–$C_4$ aliphatic acyloxymethyl group, a $C_1$–$C_2$ alkoxycarbonyloxymethyl group, a formyl group, a carboxyl group or a $C_1$–$C_2$ alkoxycarbonyl group;

(12) a compound wherein $R^3$ is a hydroxymethyl group, a $C_2$–$C_3$ aliphatic acyloxymethyl group, a formyl group or a carboxyl group;

(13) a compound wherein $R^3$ is a hydroxymethyl group or an acetoxymethyl group;

(14) a compound wherein $R^4$ is a phenyl group which is substituted with 1 to 3 substituents selected from the group consisting of $C_1$–$C_4$ alkyl, halogeno $C_1$–$C_4$ alkyl, $C_1$–$C_4$ alkoxy, halogeno $C_1$–$C_4$ alkoxy, fluoro, chloro and bromo;

(15) a compound wherein $R^4$ is a phenyl group which is substituted with 1 to 3 substituents selected from the group consisting of methyl, trifluoromethyl, methoxy, trifluoromethoxy, difluoromethoxy, fluoro, chloro and bromo;

(16) a compound wherein $R^4$ is a phenyl group which is substituted at the position(s) selected from the group consisting of 2-, 4- and 6-position of the phenyl group with 1 or 2 substituents selected from the group consisting of fluoro and chloro;

(17) a compound wherein $R^4$ is a phenyl group which is substituted at the 4-position, 2,4-positions or 2,6-positions of the phenyl group with 1 or 2 substituents selected from the group consisting of fluoro and chloro;

(18) a compound wherein A is an oxygen atom or a sufur atom; and

(19) a compound wherein A is an oxygen atom.

In each group of compounds (1)-(5), (6)-(8), (9)-(13), (14)-(17), or (18)-(19) described above, the larger the number of the compound is, the more preferable the compound, (similarly in the group of compounds (20)-(24) described below). Compounds wherein $R^1$, $R^2$, $R^3$, $R^4$ and A are optionally selected from groups of compounds (1)-(5), (6)-(8), (9)-(13), (14)-(17), and (18)-(19), respectively, are a preferable.

Such compounds are as follows for example:

(20) a compound wherein $R^1$ is a $C_2$–$C_4$ alkenyl group, a $C_3$–$C_4$ alkenyl group substituted with fluoro or chloro, a $C_3$–$C_6$ cycloalkyl group which may be optionally substituted with $C_1$–$C_2$ alkyl or a $C_3$–$C_6$ cycloalkyl-$C_1$–$C_2$ alkyl group which may be substituted with $C_1$–$C_2$ alkyl, $R^2$ is a $C_1$–$C_4$ alkyl group, $R^3$ is a hydroxymethyl group, a $C_2$–$C_6$ aliphatic acyloxymethyl group, a benzoyloxymethyl group which may be optionally substituted with methyl, methoxy, fluoro or chloro, a $C_1$–$C_4$ alkoxycarbonyloxymethyl group, a formyl group, a carboxyl group, a $C_1$–$C_4$ alkoxycarbonyl group or a phenyloxycarbonyl group which may be optionally substituted with methyl, methoxy, fluoro or chloro, $R^4$ is a phenyl group which is substituted with 1 to 3 substituents selected from the group consisting of $C_1$–$C_4$ alkyl, halogeno $C_1$–$C_4$ alkyl, $C_1$–$C_4$ alkoxy, halogeno-$C_1$–$C_4$ alkoxy, fluoro, chloro and bromo, A is an oxygen atom or a sufur atom;

(21) a compound wherein $R^1$ is a $C_3$–$C_4$ alkenyl group, a 3-chloro-2-propenyl group, a 3,3-difluoro-2-propenyl, a 3,3-dichloro-2-propenyl group, a cyclopropyl group, a 2-methylcyclpropyl group, a 2-ethylcyclopropyl group, a cyclobutyl group, a cyclopentyl group, a 2-methylcyclopentyl group, a cyclohexyl group, a 2-methylcyclohexyl group, a cyclopropylmethyl group, a 2-methylcyclopropylmethyl group, a 2-ethylcyclopropylmethyl group, a cyclobutylmethyl group, a 2-methylcyclobutylmethyl group, a cyclopentylmethyl group or a 2-methylcyclohexylmethyl group, $R^2$ is a $C_1$–$C_4$ alkyl group, $R^3$ is a hydroxymethyl group, a $C_2$–$C_6$ aliphatic acyloxymethyl group, a benzoyloxymethyl group, a $C_1$–$C_2$ alkoxycarbonyloxymethyl group, a formyl group, a carboxyl group, a $C_1$–$C_2$ alkoxycarbonyl group or a phenyloxycarbonyl group, $R^4$ is a phenyl group which is substituted with 1 to 3 substituents selected from the group consisting of methyl, trifluoromethyl, methoxy, trifluoromethoxy, difluoromethoxy, fluoro, chloro and bromo, A is an oxygen atom or a sulfur atom;

(22) a compound wherein $R^1$ is a 2-propenyl group, a 2-butenyl group, a cyclopropyl group, a 2-methylcyclopropyl group, a cyclopentyl group, a 2-methylcyclopentyl group, a cyclohexyl group, a 2-methylcyclohexyl group, a cyclopropylmethyl group, a 2-methylcyclopropylmethyl group, a cyclopentylmethyl group or a 2-methylcyclohexylmethyl group, $R^2$ is a $C_1$–$C_2$ alkyl group, $R^3$ is a hydroxymethyl group, a $C_2$–$C_4$ aliphatic acyloxymethyl group, a $C_1$–$C_2$ alkoxycarbonyloxymethyl group, a formyl group, a carboxyl group or a $C_1$–$C_2$ alkoxycarbonyl group, $R^4$ is a phenyl group which is substituted at the position(s) selected from the group consisting of 2-, 4- and 6-position of the phenyl group with 1 or 2 substituents selected from the group consisting of fluoro and chloro, A is an oxygen atom;

(23) a compound wherein $R^1$ is a 2-propenyl group, a 2-butenyl group, a cyclopropyl group, a 2-methylcyclopropyl group, a cyclopropylmethyl group or a 2-methylcyclopropylmethyl group, $R^2$ is a $C_1$–$C_2$ alkyl group, $R^3$ is a hydroxymethyl group, a $C_2$–$C_3$ aliphatic acyloxymethyl group, a formyl group or a carboxyl group, $R^4$ is a phenyl group which is substituted at the position(s) selected from the group consisting of 2-, 4- and 6-position of the phenyl group with 1 or 2 substituents selected from the group consisting of fluoro and chloro, A is an oxygen atom; and

(24) a compound wherein $R^1$ is a 2-butenyl group, a cyclopropylmethyl group of a 2-methylcyclopropylmethyl group $R^2$ is a methyl group, $R^3$ is a hydroxymethyl group or an acetoxymethyl group, $R^4$ is a phenyl group which is substituted at the 4position, 2,4-positions or, 2,6-positions of the phenyl group with 1 or 2 substituents selected from the group consisting of fluoro and chloro, A is an oxygen atom.

Preferred compounds of formula (I) can be exemplified in Table 1.

TABLE 1

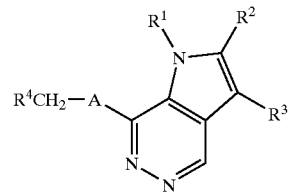

(I)

| Exemp. Comp. No. | $R^1$ | $R^2$ | $R^3$ | A | $R^4$ |
|---|---|---|---|---|---|
| 1 | CH=CHCH$_3$ | Me | CH$_2$OH | O | Ph |
| 2 | CH$_2$CH=CH$_2$ | Me | CH$_2$OH | O | Ph |
| 3 | CH$_2$C(CH$_3$)=CH$_2$ | Me | CH$_2$OH | O | Ph |
| 4 | CH$_2$CH=CHCH$_3$ | Me | CH$_2$OH | O | Ph |
| 5 | CH$_2$CH=CF$_2$ | Me | CH$_2$OH | O | Ph |
| 6 | Pr$^c$ | Me | CH$_2$OH | O | Ph |
| 7 | 2-MePr$^c$ | Me | CH$_2$OH | O | Ph |
| 8 | CH$_2$Pr$^c$ | Me | CH$_2$OH | O | Ph |
| 9 | CH$_2$(2-MePr$^c$) | Me | CH$_2$OH | O | Ph |
| 10 | CH$_2$Bu$^c$ | Me | CH$_2$OH | O | Ph |
| 11 | CH$_2$Pn$^c$ | Me | CH$_2$OH | O | Ph |
| 12 | CH$_2$Hx$^c$ | Me | CH$_2$OH | O | Ph |
| 13 | CH=CHCH$_2$ | Me | CH$_2$OH | O | 2-FPh |
| 14 | CH$_2$CH=CH$_2$ | Me | CH$_2$OH | O | 2-FPh |
| 15 | CH$_2$CH=CHCH$_3$ | Me | CH$_2$OH | O | 2-FPh |
| 16 | CH$_2$Pr$^c$ | Me | CH$_2$OH | O | 2-FPh |
| 17 | CH$_2$(2-MePr$^c$) | Me | CH$_2$OH | O | 2-FPh |
| 18 | CH=CH$_2$ | Me | CH$_2$OH | O | 4-FPh |
| 19 | CH=CHCH$_3$ | Me | CH$_2$OH | O | 4-FPh |
| 20 | CH$_2$CH=CH$_2$ | Me | CH$_2$OH | O | 4-FPh |
| 21 | CH$_2$C(CH$_3$)=CH$_2$ | Me | CH$_2$OH | O | 4-FPh |
| 22 | CH$_2$CH=CHCH$_3$ | Me | CH$_2$OH | O | 4-FPh |
| 23 | CH$_2$CH=CHCH$_2$CH$_3$ | Me | CH$_2$OH | O | 4-FPh |
| 24 | CH$_2$CH=CF$_2$ | Me | CH$_2$OH | O | 4-FPh |
| 25 | CH$_2$CH=CHCl | Me | CH$_2$OH | O | 4-FPh |
| 26 | CH$_2$CH=CCl$_2$ | Me | CH$_2$OH | O | 4-FPh |
| 27 | Pr$^c$ | Me | CH$_2$OH | O | 4-FPh |
| 28 | 2-MePr$^c$ | Me | CH$_2$OH | O | 4-FPh |
| 29 | Bu$^c$ | Me | CH$_2$OH | O | 4-FPh |
| 30 | Pn$^c$ | Me | CH$_2$OH | O | 4-FPh |
| 31 | Hx$^c$ | Me | CH$_2$OH | O | 4-FPh |
| 32 | CH$_2$Pr$^c$ | Me | CH$_2$OH | O | 4-FPh |
| 33 | CH$_2$(2-MePr$^c$) | Me | CH$_2$OH | O | 4-FPh |
| 34 | CH$_2$CH$_2$Pr$^c$ | Me | CH$_2$OH | O | 4-FPh |

TABLE 1-continued (I)

| Exemp. Comp. No. | R¹ | R² | R³ | A | R⁴ |
|---|---|---|---|---|---|
| 35 | $CH_2Bu^c$ | Me | $CH_2OH$ | O | 4-FPh |
| 36 | $CH_2Pn^c$ | Me | $CH_2OH$ | O | 4-FPh |
| 37 | $CH_2(2\text{-}MePn^c)$ | Me | $CH_2OH$ | O | 4-FPh |
| 38 | $CH_2Hx^c$ | Me | $CH_2OH$ | O | 4-FPh |
| 39 | $CH_2(2\text{-}MeHx^c)$ | Me | $CH_2OH$ | O | 4-FPh |
| 40 | $CH=CHCH_3$ | Me | $CH_2OH$ | O | 2,4-diFPh |
| 41 | $CH_2CH=CH_2$ | Me | $CH_2OH$ | O | 2,4-diFPh |
| 42 | $CH_2C(CH_3)=CH_2$ | Me | $CH_2OH$ | O | 2,4-diFPh |
| 43 | $CH_2CH=CHCH_3$ | Me | $CH_2OH$ | O | 2,4-diFPh |
| 44 | $CH_2CH=CF_2$ | Me | $CH_2OH$ | O | 2,4-diFPh |
| 45 | $Pr^c$ | Me | $CH_2OH$ | O | 2,4-diFPh |
| 46 | $2\text{-}MePr^c$ | Me | $CH_2OH$ | O | 2,4-diFPh |
| 47 | $CH_2Pr^c$ | Me | $CH_2OH$ | O | 2,4-diFPh |
| 48 | $CH_2(2\text{-}MePr^c)$ | Me | $CH_2OH$ | O | 2,4-diFPh |
| 49 | $CH_2Bu^c$ | Me | $CH_2OH$ | O | 2,4-diFPh |
| 50 | $CH_2Pn^c$ | Me | $CH_2OH$ | O | 2,4-diFPh |
| 51 | $CH_2Hx^c$ | Me | $CH_2OH$ | O | 2,4-diFPh |
| 52 | $CH=CHCH_3$ | Me | $CH_2OH$ | O | 2-ClPh |
| 53 | $CH_2CH=CH_2$ | Me | $CH_2OH$ | O | 2-ClPh |
| 54 | $CH_2CH=CHCH_3$ | Me | $CH_2OH$ | O | 2-ClPh |
| 55 | $CH_2Pr^c$ | Me | $CH_2OH$ | O | 2-ClPh |
| 56 | $CH_2(2\text{-}MePr^c)$ | Me | $CH_2OH$ | O | 2-ClPh |
| 57 | $CH=CHCH_3$ | Me | $CH_2OH$ | O | 4-ClPh |
| 58 | $CH_2CH=CH_2$ | Me | $CH_2OH$ | O | 4-ClPh |
| 59 | $CH_2CH=CHCH_3$ | Me | $CH_2OH$ | O | 4-ClPh |
| 60 | $CH_2Pr^c$ | Me | $CH_2OH$ | O | 4-ClPh |
| 61 | $CH_2(2\text{-}MePr^c)$ | Me | $CH_2OH$ | O | 4-ClPh |
| 62 | $CH_2CH=CH_2$ | Me | $CH_2OH$ | O | 2-F,4-ClPh |
| 63 | $CH_2CH=CHCH_3$ | Me | $CH_2OH$ | O | 2-F,4-ClPh |
| 64 | $CH_2Pr^c$ | Me | $CH_2OH$ | O | 2-F,4-ClPh |
| 65 | $CH_2(2\text{-}MePr^c)$ | Me | $CH_2OH$ | O | 2-F,4-ClPh |
| 66 | $CH_2CH=CH_2$ | Me | $CH_2OH$ | O | 2-Cl,4-FPh |
| 67 | $CH_2CH=CHCH_3$ | Me | $CH_2OH$ | O | 2-Cl,4-FPh |
| 68 | $CH_2Pr^c$ | Me | $CH_2OH$ | O | 2-Cl,4-FPh |
| 69 | $CH_2(2\text{-}MePr^c)$ | Me | $CH_2OH$ | O | 2-Cl,4-FPh |
| 70 | $CH_2CH=CH_2$ | Me | $CH_2OH$ | O | 2,4-diClPh |
| 71 | $CH_2CH=CHCH_3$ | Me | $CH_2OH$ | O | 2,4-diClPh |
| 72 | $CH_2Pr^c$ | Me | $CH_2OH$ | O | 2,4-diClPh |
| 73 | $CH_2(2\text{-}MePr^c)$ | Me | $CH_2OH$ | O | 2,4-diClPh |
| 74 | $CH=CHCH_3$ | Me | $CH_2OAc$ | O | Ph |
| 75 | $CH_2CH=CH_2$ | Me | $CH_2OAc$ | O | Ph |
| 76 | $CH_2C(CH_3)=CH_2$ | Me | $CH_2OAc$ | O | Ph |
| 77 | $CH_2CH=CHCH_3$ | Me | $CH_2OAc$ | O | Ph |
| 78 | $CH_2CH=CF_2$ | Me | $CH_2OAc$ | O | Ph |
| 79 | $Pr^c$ | Me | $CH_2OAc$ | O | Ph |
| 80 | $2\text{-}MePr^c$ | Me | $CH_2OAc$ | O | Ph |
| 81 | $CH_2Pr^c$ | Me | $CH_2OAc$ | O | Ph |
| 82 | $CH_2(2\text{-}MePr^c)$ | Me | $CH_2OAc$ | O | Ph |
| 83 | $CH_2Bu^c$ | Me | $CH_2OAc$ | O | Ph |
| 84 | $CH_2Pn^c$ | Me | $CH_2OAc$ | O | Ph |
| 85 | $CH_2Hx^c$ | Me | $CH_2OAc$ | O | Ph |
| 86 | $CH=CHCH_3$ | Me | $CH_2OAc$ | O | 2-FPh |
| 87 | $CH_2CH=CH_2$ | Me | $CH_2OAc$ | O | 2-FPh |
| 88 | $CH_2CH=CHCH_3$ | Me | $CH_2OAc$ | O | 2-FPh |
| 89 | $CH_2Pr^c$ | Me | $CH_2OAc$ | O | 2-FPh |
| 90 | $CH_2(2\text{-}MePr^c)$ | Me | $CH_2OAc$ | O | 2-FPh |
| 91 | $CH=CH_2$ | Me | $CH_2OAc$ | O | 4-FPh |
| 92 | $CH=CHCH_3$ | Me | $CH_2OAc$ | O | 4-FPh |
| 93 | $CH_2CH=CH_2$ | Me | $CH_2OAc$ | O | 4-FPh |
| 94 | $CH_2C(CH_3)=CH_2$ | Me | $CH_2OAc$ | O | 4-FPh |
| 95 | $CH_2CH=CHCH_3$ | Me | $CH_2OAc$ | O | 4-FPh |
| 96 | $CH_2CH=CHCH_2CH_3$ | Me | $CH_2OAc$ | O | 4-FPh |
| 97 | $CH_2CH=CF_2$ | Me | $CH_2OAc$ | O | 4-FPh |

TABLE 1-continued

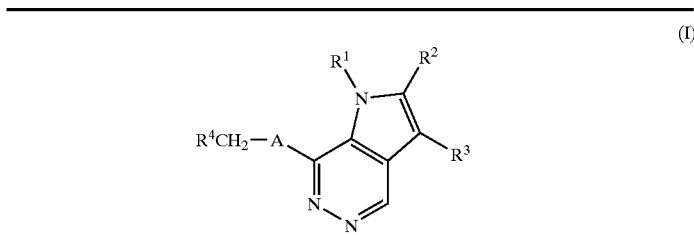

| Exemp. Comp. No. | $R^1$ | $R^2$ | $R^3$ | A | $R^4$ |
|---|---|---|---|---|---|
| 98 | $CH_2CH=CHCl$ | Me | $CH_2OAc$ | O | 4-FPh |
| 99 | $CH_2CH=CCl_2$ | Me | $CH_2OAc$ | O | 4-FPh |
| 100 | $Pr^c$ | Me | $CH_2OAc$ | O | 4-FPh |
| 101 | 2-$MePr^c$ | Me | $CH_2OAc$ | O | 4-FPh |
| 102 | $Bu^c$ | Me | $CH_2OAc$ | O | 4-FPh |
| 103 | $Pn^c$ | Me | $CH_2OAc$ | O | 4-FPh |
| 104 | $Hx^c$ | Me | $CH_2OAc$ | O | 4-FPh |
| 105 | $CH_2Pr^c$ | Me | $CH_2OAc$ | O | 4-FPh |
| 106 | $CH_2(2\text{-}MePr^c)$ | Me | $CH_2OAc$ | O | 4-FPh |
| 107 | $CH_2CH_2Pr^c$ | Me | $CH_2OAc$ | O | 4-FPh |
| 108 | $CH_2Bu^c$ | Me | $CH_2OAc$ | O | 4-FPh |
| 109 | $CH_2Pn^c$ | Me | $CH_2OAc$ | O | 4-FPh |
| 110 | $CH_2(2\text{-}MePn^c)$ | Me | $CH_2OAc$ | O | 4-FPh |
| 111 | $CH_2Hx^c$ | Me | $CH_2OAc$ | O | 4-FPh |
| 112 | $CH_2(2\text{-}MeHx^c)$ | Me | $CH_2OAc$ | O | 4-FPh |
| 113 | $CH=CHCH_3$ | Me | $CH_2OAc$ | O | 2,4-diFPh |
| 114 | $CH_2CH=CH_2$ | Me | $CH_2OAc$ | O | 2,4-diFPh |
| 115 | $CH_2C(CH_3)=CH_2$ | Me | $CH_2OAc$ | O | 2,4-diFPh |
| 116 | $CH_2CH=CHCH_3$ | Me | $CH_2OAc$ | O | 2,4-diFPh |
| 117 | $CH_2CH=CF_2$ | Me | $CH_2OAc$ | O | 2,4-diFPh |
| 118 | $Pr^c$ | Me | $CH_2OAc$ | O | 2,4-diFPh |
| 119 | 2-$MePr^c$ | Me | $CH_2OAc$ | O | 2,4-diFPh |
| 120 | $CH_2Pr^c$ | Me | $CH_2OAc$ | O | 2,4-diFPh |
| 121 | $CH_2(2\text{-}MePr^c)$ | Me | $CH_2OAc$ | O | 2,4-diFPh |
| 122 | $CH_2Bu^c$ | Me | $CH_2OAc$ | O | 2,4-diFPh |
| 123 | $CH_2Pn^c$ | Me | $CH_2OAc$ | O | 2,4-diFPh |
| 124 | $CH_2Hx^c$ | Me | $CH_2OAc$ | O | 2,4-diFPh |
| 125 | $CH=CHCH_3$ | Me | $CH_2OAc$ | O | 2-ClPh |
| 126 | $CH_2CH=CH_2$ | Me | $CH_2OAc$ | O | 2-ClPh |
| 127 | $CH_2CH=CHCH_3$ | Me | $CH_2OAc$ | O | 2-ClPh |
| 128 | $CH_2Pr^c$ | Me | $CH_2OAc$ | O | 2-ClPh |
| 129 | $CH_2(2\text{-}MePr^c)$ | Me | $CH_2OAc$ | O | 2-ClPh |
| 130 | $CH=CHCH_3$ | Me | $CH_2OAc$ | O | 4-ClPh |
| 131 | $CH_2CH=CH_2$ | Me | $CH_2OAc$ | O | 4-ClPh |
| 132 | $CH_2CH=CHCH_3$ | Me | $CH_2OAc$ | O | 4-ClPh |
| 133 | $CH_2Pr^c$ | Me | $CH_2OAc$ | O | 4-ClPh |
| 134 | $CH_2(2\text{-}MePr^c)$ | Me | $CH_2OAc$ | O | 4-ClPh |
| 135 | $CH_2CH=CH_2$ | Me | $CH_2OAc$ | O | 2-F,4-ClPh |
| 136 | $CH_2CH=CHCH_3$ | Me | $CH_2OAc$ | O | 2-F,4-ClPh |
| 137 | $CH_2Pr^c$ | Me | $CH_2OAc$ | O | 2-F,4-ClPh |
| 138 | $CH_2(2\text{-}MePr^c)$ | Me | $CH_2OAc$ | O | 2-F,4-ClPh |
| 139 | $CH_2CH=CH_2$ | Me | $CH_2OAc$ | O | 2-Cl,4-FPh |
| 140 | $CH_2CH=CHCH_3$ | Me | $CH_2OAc$ | O | 2-Cl,4-FPh |
| 141 | $CH_2Pr^c$ | Me | $CH_2OAc$ | O | 2-Cl,4-FPh |
| 142 | $CH_2(2\text{-}MePr^c)$ | Me | $CH_2OAc$ | O | 2-Cl,4-FPh |
| 143 | $CH_2CH=CH_2$ | Me | $CH_2OAc$ | O | 2,4-diClPh |
| 144 | $CH_2CH=CHCH_3$ | Me | $CH_2OAc$ | O | 2,4-diClPh |
| 145 | $CH_2Pr^c$ | Me | $CH_2OAc$ | O | 2,4-diClPh |
| 146 | $CH_2(2\text{-}MePr^c)$ | Me | $CH_2OAc$ | O | 2,4-diClPh |
| 147 | $CH=CHCH_3$ | Me | $CH_2OPrp$ | O | Ph |
| 148 | $CH_2CH=CH_2$ | Me | $CH_2OPrp$ | O | Ph |
| 149 | $CH_2CH=CHCH_3$ | Me | $CH_2OPrp$ | O | Ph |
| 150 | $CH_2CH=CF_2$ | Me | $CH_2OPrP$ | O | Ph |
| 151 | $Pr^c$ | Me | $CH_2OPrp$ | O | Ph |
| 152 | 2-$MePr^c$ | Me | $CH_2OPrp$ | O | Ph |
| 153 | $CH_2Pr^c$ | Me | $CH_2OPrp$ | O | Ph |
| 154 | $CH_2(2\text{-}MePr^c)$ | Me | $CH_2OPrp$ | O | Ph |
| 155 | $CH_2CH=CH_2$ | Me | $CH_2OPrp$ | O | 2-FPh |
| 156 | $CH_2CH=CHCH_3$ | Me | $CH_2OPrp$ | O | 2-FPh |
| 157 | $CH_2Pr^c$ | Me | $CH_2OPrp$ | O | 2-FPh |
| 158 | $CH_2(2\text{-}MePr^c)$ | Me | $CH_2OPrp$ | O | 2-FPh |
| 159 | $CH=CHCH_3$ | Me | $CH_2OPrp$ | O | 4-FPh |
| 160 | $CH_2CH=CH_2$ | Me | $CH_2OPrp$ | O | 4-FPh |

TABLE 1-continued

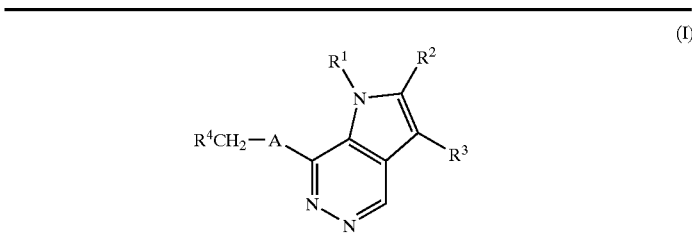

| Exemp. Comp. No. | R¹ | R² | R³ | A | R⁴ |
|---|---|---|---|---|---|
| 161 | CH₂CH=CHCH₃ | Me | CH₂OPrp | O | 4-FPh |
| 162 | CH₂CH=CF₂ | Me | CH₂OPrp | O | 4-FPh |
| 163 | CH₂CH=CHCl | Me | CH₂OPrp | O | 4-FPh |
| 164 | Prᶜ | Me | CH₂OPrp | O | 4-FPh |
| 165 | 2-MePrᶜ | Me | CH₂OPrp | O | 4-FPh |
| 166 | CH₂Prᶜ | Me | CH₂OPrp | O | 4-FPh |
| 167 | CH₂(2-MePrᶜ) | Me | CH₂OPrp | O | 4-FPh |
| 168 | CH₂Buᶜ | Me | CH₂OPrp | O | 4-FPh |
| 169 | CH₂Pnᶜ | Me | CH₂OPrp | O | 4-FPh |
| 170 | CH₂Hxᶜ | Me | CH₂OPrp | O | 4-FPh |
| 171 | CH=CHCH₃ | Me | CH₂OPrp | O | 2,4-diFPh |
| 172 | CH₂CH=CH₂ | Me | CH₂OPrp | O | 2,4-diFPh |
| 173 | CH₂CH=CHCH₃ | Me | CH₂OPrp | O | 2,4-diFPh |
| 174 | CH₂CH=CF₂ | Me | CH₂OPrp | O | 2,4-diFPh |
| 175 | Prᶜ | Me | CH₂OPrp | O | 2,4-diFPh |
| 176 | 2-MePrᶜ | Me | CH₂OPrp | O | 2,4-diFPh |
| 177 | CH₂Prᶜ | Me | CH₂OPrp | O | 2,4-diFPh |
| 178 | CH₂(2-MePrᶜ) | Me | CH₂OPrp | O | 2,4-diFPh |
| 179 | CH=CHCH₃ | Me | CH₂OPrp | O | 2-ClPh |
| 180 | CH₂CH=CH₂ | Me | CH₂OPrp | O | 2-ClPh |
| 181 | CH₂CH=CHCH₃ | Me | CH₂OPrp | O | 2-ClPh |
| 182 | CH₂Prᶜ | Me | CH₂OPrp | O | 2-ClPh |
| 183 | CH₂(2-MePrᶜ) | Me | CH₂OPrp | O | 2-ClPh |
| 184 | CH=CHCH₃ | Me | CH₂OPrp | O | 4-ClPh |
| 185 | CH₂CH=CH₂ | Me | CH₂OPrp | O | 4-ClPh |
| 186 | CH₂CH=CHCH₃ | Me | CH₂OPrp | O | 4-ClPh |
| 187 | CH₂Prᶜ | Me | CH₂OPrp | O | 4-ClPh |
| 188 | CH₂(2-MePrᶜ) | Me | CH₂OPrp | O | 4-ClPh |
| 189 | CH₂CH=CH₂ | Me | CH₂OPrp | O | 2-F,4-ClPh |
| 190 | CH₂CH=CHCH₃ | Me | CH₂OPrp | O | 2-F,4-ClPh |
| 191 | CH₂Prᶜ | Me | CH₂OPrp | O | 2-F,4-ClPh |
| 192 | CH₂(2-MePrᶜ) | Me | CH₂OPrp | O | 2-F,4-ClPh |
| 193 | CH₂CH=CH₂ | Me | CH₂OPrp | O | 2-Cl,4-FPh |
| 194 | CH₂CH=CHCH₃ | Me | CH₂OPrp | O | 2-Cl,4-FPh |
| 195 | CH₂Prᶜ | Me | CH₂OPrp | O | 2-Cl,4-FPh |
| 196 | CH₂(2-MePrᶜ) | Me | CH₂OPrp | O | 2-Cl,4-FPh |
| 197 | CH₂CH=CH₂ | Me | CH₂OPrp | O | 2,4-diClPh |
| 198 | CH₂CH=CHCH₃ | Me | CH₂OPrp | O | 2,4-diClPh |
| 199 | CH₂Prᶜ | Me | CH₂OPrp | O | 2,4-diClPh |
| 200 | CH₂(2-MePrᶜ) | Me | CH₂OPrp | O | 2,4-diClPh |
| 201 | CH₂CH=CH₂ | Me | CH₂OBur | O | Ph |
| 202 | CH₂CH=CHCH₃ | Me | CH₂OBur | O | Ph |
| 203 | CH₂Prᶜ | Me | CH₂OBur | O | Ph |
| 204 | CH₂(2-MePrᶜ) | Me | CH₂OBur | O | Ph |
| 205 | CH₂CH=CH₂ | Me | CH₂OBur | O | 2-FPh |
| 206 | CH₂CH=CHCH₃ | Me | CH₂OBur | O | 2-FPh |
| 207 | CH₂Prᶜ | Me | CH₂OBur | O | 2-FPh |
| 208 | CH₂(2-MePrᶜ) | Me | CH₂OBur | O | 2-FPh |
| 209 | CH=CHCH₃ | Me | CH₂OBur | O | 4-FPh |
| 210 | CH₂CH=CH₂ | Me | CH₂OBur | O | 4-FPh |
| 211 | CH₂CH=CHCH₃ | Me | CH₂OBur | O | 4-FPh |
| 212 | CH₂CH=CF₂ | Me | CH₂OBur | O | 4-FPh |
| 213 | Prᶜ | Me | CH₂OBur | O | 4-FPh |
| 214 | 2-MePrᶜ | Me | CH₂OBur | O | 4-FPh |
| 215 | CH₂Prᶜ | Me | CH₂OBur | O | 4-FPh |
| 216 | CH₂(2-MePrᶜ) | Me | CH₂OBur | O | 4-FPh |
| 217 | CH₂Buᶜ | Me | CH₂OBur | O | 4-FPh |
| 218 | CH₂Pnᶜ | Me | CH₂OBur | O | 4-FPh |
| 219 | CH₂Hxᶜ | Me | CH₂OBur | O | 4-FPh |
| 220 | CH₂CH=CH₂ | Me | CH₂OBur | O | 2,4-diFPh |
| 221 | CH₂CH=CHCH₃ | Me | CH₂OBur | O | 2,4-diFPh |
| 222 | Prᶜ | Me | CH₂OBur | O | 2,4-diFPh |
| 223 | 2-MePrᶜ | Me | CH₂OBur | O | 2,4-diFPh |

TABLE 1-continued (I)

Structure: R⁴CH₂—A— attached to a pyrrolo-pyridazine ring system with R¹ on N, R² and R³ on the pyrrole ring.

| Exemp. Comp. No. | R¹ | R² | R³ | A | R⁴ |
|---|---|---|---|---|---|
| 224 | CH₂Pr$^c$ | Me | CH₂OBur | O | 2,4-diFPh |
| 225 | CH₂(2-MePr$^c$) | Me | CH₂OBur | O | 2,4-diFPh |
| 226 | CH₂CH=CH₂ | Me | CH₂OBur | O | 2-ClPh |
| 227 | CH₂CH=CHCH₃ | Me | CH₂OBur | O | 2-ClPh |
| 228 | CH₂Pr$^c$ | Me | CH₂OBur | O | 2-ClPh |
| 229 | CH₂(2-MePr$^c$) | Me | CH₂OBur | O | 2-ClPh |
| 230 | CH₂CH=CH₂ | Me | CH₂OBur | O | 4-ClPh |
| 231 | CH₂CH=CHCH₃ | Me | CH₂OBur | O | 4-ClPh |
| 232 | CH₂Pr$^c$ | Me | CH₂OBur | O | 4-ClPh |
| 233 | CH₂(2-MePr$^c$) | Me | CH₂OBur | O | 4-ClPh |
| 234 | CH₂CH=CH₂ | Me | CH₂OBur | O | 2-F,4-ClPh |
| 235 | CH₂CH=CHCH₃ | Me | CH₂OBur | O | 2-F,4-ClPh |
| 236 | CH₂Pr$^c$ | Me | CH₂OBur | O | 2-F,4-ClPh |
| 237 | CH₂(2-MePr$^c$) | Me | CH₂OBur | O | 2-F,4-ClPh |
| 238 | CH₂CH=CH₂ | Me | CH₂OBur | O | 2-Cl,4-FPh |
| 239 | CH₂CH=CHCH₃ | Me | CH₂OBur | O | 2-Cl,4-FPh |
| 240 | CH₂Pr$^c$ | Me | CH₂OBur | O | 2-Cl,4-FPh |
| 241 | CH₂(2-MePr$^c$) | Me | CH₂OBur | O | 2-Cl,4-FPh |
| 242 | CH₂CH=CH₂ | Me | CH₂OBur | O | 2,4-diClPh |
| 243 | CH₂CH=CHCH₃ | Me | CH₂OBur | O | 2,4-diClPh |
| 244 | CH₂Pr$^c$ | Me | CH₂OBur | O | 2,4-diClPh |
| 245 | CH₂(2-MePr$^c$) | Me | CH₂OBur | O | 2,4-diClPh |
| 246 | CH₂CH=CH₂ | Me | CH₂OCOPh | O | Ph |
| 247 | CH₂Pr$^c$ | Me | CH₂OCOPh | O | Ph |
| 248 | CH₂(2-MePr$^c$) | Me | CH₂OCOPh | O | Ph |
| 249 | CH₂(2-MePr$^c$) | Me | CH₂OCO(4-Me)Ph | O | Ph |
| 250 | CH₂CH=CH₂ | Me | CH₂OCOPh | O | 2-FPh |
| 251 | CH₂Pr$^c$ | Me | CH₂OCOPh | O | 2-FPh |
| 252 | CH₂(2-MePr$^c$) | Me | CH₂OCOPh | O | 2-FPh |
| 253 | CH₂(2-MePr$^c$) | Me | CH₂OCO(4-Me)Ph | O | 2-FPh |
| 254 | CH=CHCH₃ | Me | CH₂OCOPh | O | 4-FPh |
| 255 | CH₂CH=CH₂ | Me | CH₂OCOPh | O | 4-FPh |
| 256 | CH₂CH=CH₂ | Me | CH₂OCO(4-Me)Ph | O | 4-FPh |
| 257 | CH₂CH=CHCH₃ | Me | CH₂OCOPh | O | 4-FPh |
| 258 | CH₂CH=CF₂ | Me | CH₂OCOPh | O | 4-FPh |
| 259 | Pr$^c$ | Me | CH₂OCOPh | O | 4-FPh |
| 260 | 2-MePr$^c$ | Me | CH₂OCOPh | O | 4-FPh |
| 261 | CH₂Pr$^c$ | Me | CH₂OCOPh | O | 4-FPh |
| 262 | CH₂Pr$^c$ | Me | CH₂OCO(4-Me)Ph | O | 4-FPh |
| 263 | CH₂(2-MePr$^c$) | Me | CH₂OCOPh | O | 4-FPh |
| 264 | CH₂(2-MePr$^c$) | Me | CH₂OCO(4-Me)Ph | O | 4-FPh |
| 265 | CH₂(2-MePr$^c$) | Me | CH₂OCO(4-MeO)Ph | O | 4-FPh |
| 266 | CH₂(2-MePr$^c$) | Me | CH₂OCO(4-F)Ph | O | 4-FPh |
| 267 | CH₂(2-MePr$^c$) | Me | CH₂OCO(4-Cl)Ph | O | 4-FPh |
| 268 | CH₂Bu$^c$ | Me | CH₂OCOPh | O | 4-FPh |
| 269 | CH₂Pn$^c$ | Me | CH₂OCOPh | O | 4-FPh |
| 270 | CH₂Hx$^c$ | Me | CH₂OCOPh | O | 4-FPh |
| 271 | CH₂CH=CH₂ | Me | CH₂OCOPh | O | 2,4-diFPh |
| 272 | CH₂CH=CH₂ | Me | CH₂OCO(4-Me)Ph | O | 2,4-diFPh |
| 273 | CH₂CH=CHCH₃ | Me | CH₂OCOPh | O | 2,4-diFPh |
| 274 | Pr$^c$ | Me | CH₂OCOPh | O | 2,4-diFPh |
| 275 | CH₂Pr$^c$ | Me | CH₂OCOPh | O | 2,4-diFPh |
| 276 | CH₂(2-MePr$^c$) | Me | CH₂OCOPh | O | 2,4-diFPh |
| 277 | CH₂(2-MePr$^c$) | Me | CH₂OCO(4-Me)Ph | O | 2,4-diFPh |
| 278 | CH₂CH=CH₂ | Me | CH₂OCOPh | O | 2-ClPh |
| 279 | CH₂Pr$^c$ | Me | CH₂OCOPh | O | 2-ClPh |
| 280 | CH₂(2-MePr$^c$) | Me | CH₂OCOPh | O | 2-ClPh |
| 281 | CH₂(2-MePr$^c$) | Me | CH₂OCO(4-Me)Ph | O | 2-ClPh |
| 282 | CH₂CH=CH₂ | Me | CH₂OCOPh | O | 4-ClPh |
| 283 | CH₂CH=CHCH₃ | Me | CH₂OCOPh | O | 4-ClPh |
| 284 | CH₂Pr$^c$ | Me | CH₂OCOPh | O | 4-ClPh |
| 285 | CH₂(2-MePr$^c$) | Me | CH₂OCOPh | O | 4-ClPh |

TABLE 1-continued

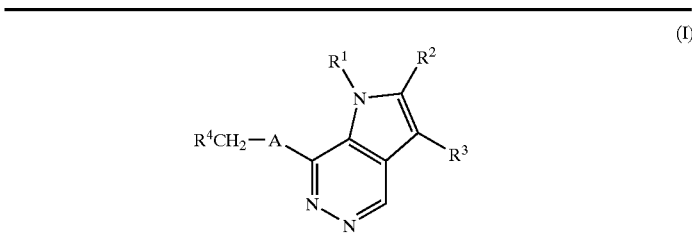

| Exemp. Comp. No. | R$^1$ | R$^2$ | R$^3$ | A | R$^4$ |
|---|---|---|---|---|---|
| 286 | CH$_2$(2-MePr$^c$) | Me | CH$_2$OCO(4-Me)Ph | O | 4-ClPh |
| 287 | CH$_2$CH=CHCH$_3$ | Me | CH$_2$OCOPh | O | 2-F,4-ClPh |
| 288 | CH$_2$Pr$^c$ | Me | CH$_2$OCOPh | O | 2-F,4-ClPh |
| 289 | CH$_2$(2-MePr$^c$) | Me | CH$_2$OCOPh | O | 2-F,4-ClPh |
| 290 | CH$_2$(2-MePr$^c$) | Me | CH$_2$OCO(4-Me)Ph | O | 2-F,4-ClPh |
| 291 | CH$_2$CH=CHCH$_3$ | Me | CH$_2$OCOPh | O | 2-Cl,4-FPh |
| 292 | CH$_2$Pr$^c$ | Me | CH$_2$OCOPh | O | 2-Cl,4-FPh |
| 293 | CH$_2$(2-MePr$^c$) | Me | CH$_2$OCOPh | O | 2-Cl,4-FPh |
| 294 | CH$_2$(2-MePr$^c$) | Me | CH$_2$OCO(4-Me)Ph | O | 2-Cl,4-FPh |
| 295 | CH$_2$CH=CHCH$_3$ | Me | CH$_2$OCOPh | O | 2,4-diClPh |
| 296 | CH$_2$Pr$^c$ | Me | CH$_2$OCOPh | O | 2,4-diClPh |
| 297 | CH$_2$(2-MePr$^c$) | Me | CH$_2$OCOPh | O | 2,4-diClPh |
| 298 | CH$_2$(2-MePr$^c$) | Me | CH$_2$OCO(4-Me)Ph | O | 2,4-diClPh |
| 299 | CH$_2$CH=CHCH$_3$ | Me | CH$_2$OCO$_2$Me | O | Ph |
| 300 | CH$_2$Pr$^c$ | Me | CH$_2$OCO$_2$Me | O | Ph |
| 301 | CH$_2$(2-MePr$^c$) | Me | CH$_2$OCO$_2$Me | O | Ph |
| 302 | CH$_2$CH=CH$_2$ | Me | CH$_2$OCO$_2$Me | O | 2-FPh |
| 303 | CH$_2$Pr$^c$ | Me | CH$_2$OCO$_2$Me | O | 2-FPh |
| 304 | CH$_2$(2-MePr$^c$) | Me | CH$_2$OCO$_2$Me | O | 2-FPh |
| 305 | CH=CHCH$_3$ | Me | CH$_2$OCO$_2$Me | O | 4-FPh |
| 306 | CH$_2$CH=CH$_2$ | Me | CH$_2$OCO$_2$Me | O | 4-FPh |
| 307 | CH$_2$CH=CHCH$_3$ | Me | CH$_2$OCO$_2$Me | O | 4-FPh |
| 308 | Pr$^c$ | Me | CH$_2$OCO$_2$Me | O | 4-FPh |
| 309 | 2-MePr$^c$ | Me | CH$_2$OCO$_2$Me | O | 4-FPh |
| 310 | CH$_2$Pr$^c$ | Me | CH$_2$OCO$_2$Me | O | 4-FPh |
| 311 | CH$_2$(2-MePr$^c$) | Me | CH$_2$OCO$_2$Me | O | 4-FPh |
| 312 | CH$_2$Bu$^c$ | Me | CH$_2$OCO$_2$Me | O | 4-FPh |
| 313 | CH$_2$Pn$^c$ | Me | CH$_2$OCO$_2$Me | O | 4-FPh |
| 314 | CH$_2$Hx$^c$ | Me | CH$_2$OCO$_2$Me | O | 4-FPh |
| 315 | CH$_2$CH=CHCH$_3$ | Me | CH$_2$OCO$_2$Me | O | 2,4-diFPh |
| 316 | CH$_2$Pr$^c$ | Me | CH$_2$OCO$_2$Me | O | 2,4-diFPh |
| 317 | CH$_2$(2-MePr$^c$) | Me | CH$_2$OCO$_2$Me | O | 2,4-diFPh |
| 318 | CH$_2$CH=CHCH$_3$ | Me | CH$_2$OCO$_2$Me | O | 2-ClPh |
| 319 | CH$_2$Pr$^c$ | Me | CH$_2$OCO$_2$Me | O | 2-ClPh |
| 320 | CH$_2$(2-MePr$^c$) | Me | CH$_2$OCO$_2$Me | O | 2-ClPh |
| 321 | CH$_2$CH=CHCH$_3$ | Me | CH$_2$OCO$_2$Me | O | 4-ClPh |
| 322 | CH$_2$Pr$^c$ | Me | CH$_2$OCO$_2$Me | O | 4-ClPh |
| 323 | CH$_2$(2-MePr$^c$) | Me | CH$_2$OCO$_2$Me | O | 4-ClPh |
| 324 | CH$_2$CH=CHCH$_3$ | Me | CH$_2$OCO$_2$Me | O | 2-F,4-ClPh |
| 325 | CH$_2$Pr$^c$ | Me | CH$_2$OCO$_2$Me | O | 2-F,4-ClPh |
| 326 | CH$_2$(2-MePr$^c$) | Me | CH$_2$OCO$_2$Me | O | 2-F,4-ClPh |
| 327 | CH$_2$CH=CHCH$_3$ | Me | CH$_2$OCO$_2$Me | O | 2-Cl,4-FPh |
| 328 | CH$_2$Pr$^c$ | Me | CH$_2$OCO$_2$Me | O | 2-Cl,4-FPh |
| 329 | CH$_2$(2-MePr$^c$) | Me | CH$_2$OCO$_2$Me | O | 2-Cl,4-FPh |
| 330 | CH$_2$CH=CHCH$_3$ | Me | CH$_2$OCO$_2$Me | O | 2,4-diClPh |
| 331 | CH$_2$Pr$^c$ | Me | CH$_2$OCO$_2$Me | O | 2,4-diClPh |
| 332 | CH$_2$(2-MePr$^c$) | Me | CH$_2$OCO$_2$Me | O | 2,4-diClPh |
| 333 | CH$_2$CH=CHCH$_3$ | Me | CH$_2$OCO$_2$Et | O | Ph |
| 334 | CH$_2$Pr$^c$ | Me | CH$_2$OCO$_2$Et | O | Ph |
| 335 | CH$_2$(2-MePr$^c$) | Me | CH$_2$OCO$_2$Et | O | Ph |
| 336 | CH$_2$CH=CHCH$_3$ | Me | CH$_2$OCO$_2$Et | O | 2-FPh |
| 337 | CH$_2$Pr$^c$ | Me | CH$_2$OCO$_2$Et | O | 2-FPh |
| 338 | CH$_2$(2-MePr$^c$) | Me | CH$_2$OCO$_2$Et | O | 2-FPh |
| 339 | CH=CHCH$_3$ | Me | CH$_2$OCO$_2$Et | O | 4-FPh |
| 340 | CH$_2$CH=CH$_2$ | Me | CH$_2$OCO$_2$Et | O | 4-FPh |
| 341 | CH$_2$CH=CHCH$_3$ | Me | CH$_2$OCO$_2$Et | O | 4-FPh |
| 342 | Pr$^c$ | Me | CH$_2$OCO$_2$Et | O | 4-FPh |
| 343 | 2-MePr$^c$ | Me | CH$_2$OCO$_2$Et | O | 4-FPh |
| 344 | CH$_2$Pr$^c$ | Me | CH$_2$OCO$_2$Et | O | 4-FPh |
| 345 | CH$_2$(2-MePr$^c$) | Me | CH$_2$OCO$_2$Et | O | 4-FPh |
| 346 | CH$_2$Bu$^c$ | Me | CH$_2$OCO$_2$Et | O | 4-FPh |
| 347 | CH$_2$Pn$^c$ | Me | CH$_2$OCO$_2$Et | O | 4-FPh |
| 348 | CH$_2$Hx$^c$ | Me | CH$_2$OCO$_2$Et | O | 4-FPh |

TABLE 1-continued

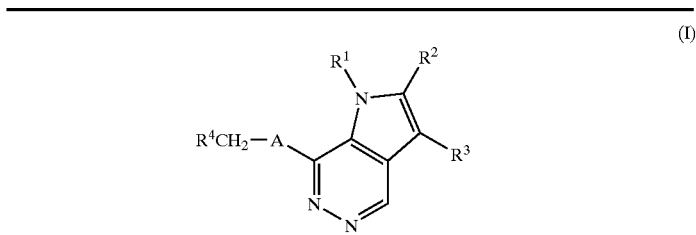

(I)

| Exemp. Comp. No. | $R^1$ | $R^2$ | $R^3$ | A | $R^4$ |
|---|---|---|---|---|---|
| 349 | $CH_2CH=CHCH_3$ | Me | $CH_2OCO_2Et$ | O | 2,4-diFPh |
| 350 | $CH_2Pr^c$ | Me | $CH_2OCO_2Et$ | O | 2,4-diFPh |
| 351 | $CH_2(2\text{-}MePr^c)$ | Me | $CH_2OCO_2Et$ | O | 2,4-diFPh |
| 352 | $CH_2CH=CHCH_3$ | Me | $CH_2OCO_2Et$ | O | 2-ClPh |
| 353 | $CH_2Pr^c$ | Me | $CH_2OCO_2Et$ | O | 2-ClPh |
| 354 | $CH_2(2\text{-}MePr^c)$ | Me | $CH_2OCO_2Et$ | O | 2-ClPh |
| 355 | $CH_2CH=CHCH_3$ | Me | $CH_2OCO_2Et$ | O | 4-ClPh |
| 356 | $CH_2Pr^c$ | Me | $CH_2OCO_2Et$ | O | 4-ClPh |
| 357 | $CH_2(2\text{-}MePr^c)$ | Me | $CH_2OCO_2Et$ | O | 4-ClPh |
| 358 | $CH_2CH=CHCH_3$ | Me | $CH_2OCO_2Et$ | O | 2-F,4-ClPh |
| 359 | $CH_2Pr^c$ | Me | $CH_2OCO_2Et$ | O | 2-F,4-ClPh |
| 360 | $CH_2(2\text{-}MePr^c)$ | Me | $CH_2OCO_2Et$ | O | 2-F,4-ClPh |
| 361 | $CH_2CH=CHCH_3$ | Me | $CH_2OCO_2Et$ | O | 2-Cl,4-FPh |
| 362 | $CH_2Pr^c$ | Me | $CH_2OCO_2Et$ | O | 2-Cl,4-FPh |
| 363 | $CH_2(2\text{-}MePr^c)$ | Me | $CH_2OCO_2Et$ | O | 2-Cl,4-FPh |
| 364 | $CH_2CH=CHCH_3$ | Me | $CH_2OCO_2Et$ | O | 2,4-diClPh |
| 365 | $CH_2Pr^c$ | Me | $CH_2OCO_2Et$ | O | 2,4-diClPh |
| 366 | $CH_2(2\text{-}MePr^c)$ | Me | $CH_2OCO_2Et$ | O | 2,4-diClPh |
| 367 | $CH_2CH=CHCH_3$ | Me | $CH_2OCO_2Pr$ | O | Ph |
| 368 | $CH_2(2\text{-}MePr^c)$ | Me | $CH_2OCO_2Pr$ | O | Ph |
| 369 | $CH_2CH=CHCH_3$ | Me | $CH_2OCO_2Pr$ | O | 2-FPh |
| 370 | $CH_2(2\text{-}MePr^c)$ | Me | $CH_2OCO_2Pr$ | O | 2-FPh |
| 371 | $CH_2CH=CHCH_3$ | Me | $CH_2OCO_2Pr$ | O | 4-FPh |
| 372 | $CH_2Pr^c$ | Me | $CH_2OCO_2Pr$ | O | 4-FPh |
| 373 | $CH_2(2\text{-}MePr^c)$ | Me | $CH_2OCO_2Pr$ | O | 4-FPh |
| 374 | $CH_2Pn^c$ | Me | $CH_2OCO_2Pr$ | O | 4-FPh |
| 375 | $CH_2Hx^c$ | Me | $CH_2OCO_2Pr$ | O | 4-FPh |
| 376 | $CH_2CH=CHCH_3$ | Me | $CH_2OCO_2Pr$ | O | 2,4-diFPh |
| 377 | $CH_2(2\text{-}MePr^c)$ | Me | $CH_2OCO_2Pr$ | O | 2,4-diFPh |
| 378 | $CH_2CH=CHCH_3$ | Me | $CH_2OCO_2Pr$ | O | 2-ClPh |
| 379 | $CH_2(2\text{-}MePr^c)$ | Me | $CH_2OCO_2Pr$ | O | 2-ClPh |
| 380 | $CH_2CH=CHCH_3$ | Me | $CH_2OCO_2Pr$ | O | 4-ClPh |
| 381 | $CH_2(2\text{-}MePr^c)$ | Me | $CH_2OCO_2Pr$ | O | 4-ClPh |
| 382 | $CH_2CH=CHCH_3$ | Me | $CH_2OCO_2Pr$ | O | 2-F,4-ClPh |
| 383 | $CH_2(2\text{-}MePr^c)$ | Me | $CH_2OCO_2Pr$ | O | 2-F,4-ClPh |
| 384 | $CH_2CH=CHCH_3$ | Me | $CH_2OCO_2Pr$ | O | 2-Cl,4-FPh |
| 385 | $CH_2(2\text{-}MePr^c)$ | Me | $CH_2OCO_2Pr$ | O | 2-Cl,4-FPh |
| 386 | $CH_2CH=CHCH_3$ | Me | $CH_2OCO_2Pr$ | O | 2,4-diClPh |
| 387 | $CH_2(2\text{-}MePr^c)$ | Me | $CH_2OCO_2Pr$ | O | 2,4-diClPh |
| 388 | $CH_2CH=CHCH_3$ | Me | $CH_2OCO_2Bu$ | O | Ph |
| 389 | $CH_2(2\text{-}MePr^c)$ | Me | $CH_2OCO_2Bu$ | O | Ph |
| 390 | $CH_2CH=CHCH_3$ | Me | $CH_2OCO_2Bu$ | O | 2-FPh |
| 391 | $CH_2(2\text{-}MePr^c)$ | Me | $CH_2OCO_2Bu$ | O | 2-FPh |
| 392 | $CH_2CH=CHCH_3$ | Me | $CH_2OCO_2Bu$ | O | 4-FPh |
| 393 | $CH_2Pr^c$ | Me | $CH_2OCO_2Bu$ | O | 4-FPh |
| 394 | $CH_2(2\text{-}MePr^c)$ | Me | $CH_2OCO_2Bu$ | O | 4-FPh |
| 395 | $CH_2Pn^c$ | Me | $CH_2OCO_2Bu$ | O | 4-FPh |
| 396 | $CH_2Hx^c$ | Me | $CH_2OCO_2Bu$ | O | 4-FPh |
| 397 | $CH_2CH=CHCH_3$ | Me | $CH_2OCO_2Bu$ | O | 2,4-diFPh |
| 398 | $CH_2(2\text{-}MePr^c)$ | Me | $CH_2OCO_2Bu$ | O | 2,4-diFPh |
| 399 | $CH_2CH=CHCH_3$ | Me | $CH_2OCO_2Bu$ | O | 2-ClPh |
| 400 | $CH_2(2\text{-}MePr^c)$ | Me | $CH_2OCO_2Bu$ | O | 2-ClPh |
| 401 | $CH_2CH=CHCH_3$ | Me | $CH_2OCO_2Bu$ | O | 4-ClPh |
| 402 | $CH_2(2\text{-}MePr^c)$ | Me | $CH_2OCO_2Bu$ | O | 4-ClPh |
| 403 | $CH_2CH=CHCH_3$ | Me | $CH_2OCO_2Bu$ | O | 2-F,4-ClPh |
| 404 | $CH_2(2\text{-}MePr^c)$ | Me | $CH_2OCO_2Bu$ | O | 2-F,4-ClPh |
| 405 | $CH_2CH=CHCH_3$ | Me | $CH_2OCO_2Bu$ | O | 2-Cl,4-FPh |
| 406 | $CH_2(2\text{-}MePr^c)$ | Me | $CH_2OCO_2Bu$ | O | 2-Cl,4-FPh |
| 407 | $CH_2CH=CHCH_3$ | Me | $CH_2OCO_2Bu$ | O | 2,4-diClPh |
| 408 | $CH_2(2\text{-}MePr^c)$ | Me | $CH_2OCO_2Bu$ | O | 2,4-diClPh |
| 409 | $CH_2CH=CHCH_3$ | Me | CHO | O | Ph |
| 410 | $CH_2Pr^c$ | Me | CHO | O | Ph |
| 411 | $CH_2(2\text{-}MePr^c)$ | Me | CHO | O | Ph |

TABLE 1-continued $$\text{(I)}$$

Structure: R4CH2—A attached to a pyrrolo-pyridazine core with R1 on N, R2 and R3 on the pyrrole ring.

| Exemp. Comp. No. | R¹ | R² | R³ | A | R⁴ |
|---|---|---|---|---|---|
| 412 | CH₂CH=CHCH₃ | Me | CHO | O | 2-FPh |
| 413 | CH₂Pr^c | Me | CHO | O | 2-FPh |
| 414 | CH₂(2-MePr^c) | Me | CHO | O | 2-FPh |
| 415 | CH=CHCH₃ | Me | CHO | O | 4-FPh |
| 416 | CH₂CH=CH₂ | Me | CHO | O | 4-FPh |
| 417 | CH₂CH=CHCH₃ | Me | CHO | O | 4-FPh |
| 418 | Pr^c | Me | CHO | O | 4-FPh |
| 419 | 2-MePr^c | Me | CHO | O | 4-FPh |
| 420 | CH₂Pr^c | Me | CHO | O | 4-FPh |
| 421 | CH₂(2-MePr^c) | Me | CHO | O | 4-FPh |
| 422 | CH₂Bu^c | Me | CHO | O | 4-FPh |
| 423 | CH₂Pn^c | Me | CHO | O | 4-FPh |
| 424 | CH₂Hx^c | Me | CHO | O | 4-FPh |
| 425 | CH₂CH=CHCH₃ | Me | CHO | O | 2,4-diFPh |
| 426 | CH₂Pr^c | Me | CHO | O | 2,4-diFPh |
| 427 | CH₂(2-MePr^c) | Me | CHO | O | 2,4-diFPh |
| 428 | CH₂CH=CHCH₃ | Me | CHO | O | 2-ClPh |
| 429 | CH₂Pr^c | Me | CHO | O | 2-ClPh |
| 430 | CH₂(2-MePr^c) | Me | CHO | O | 2-ClPh |
| 431 | CH₂CH=CHCH₃ | Me | CHO | O | 4-ClPh |
| 432 | CH₂Pr^c | Me | CHO | O | 4-ClPh |
| 433 | CH₂(2-MePr^c) | Me | CHO | O | 4-ClPh |
| 434 | CH₂CH=CHCH₃ | Me | CHO | O | 2-F,4-ClPh |
| 435 | CH₂Pr^c | Me | CHO | O | 2-F,4-ClPh |
| 436 | CH₂(2-MePr^c) | Me | CHO | O | 2-F,4-ClPh |
| 437 | CH₂CH=CHCH₃ | Me | CHO | O | 2-Cl,4-FPh |
| 438 | CH₂Pr^c | Me | CHO | O | 2-Cl,4-FPh |
| 439 | CH₂(2-MePr^c) | Me | CHO | O | 2-Cl,4-FPh |
| 440 | CH₂CH=CHCH₃ | Me | CHO | O | 2,4-diClPh |
| 441 | CH₂Pr^c | Me | CHO | O | 2,4-diClPh |
| 442 | CH₂(2-MePr^c) | Me | CHO | O | 2,4-diClPh |
| 443 | CH₂CH=CHCH₃ | Me | CO₂H | O | Ph |
| 444 | CH₂Pr^c | Me | CO₂H | O | Ph |
| 445 | CH₂(2-MePr^c) | Me | CO₂H | O | Ph |
| 446 | CH₂CH=CH₂ | Me | CO₂H | O | 2-FPh |
| 447 | CH₂Pr^c | Me | CO₂H | O | 2-FPh |
| 448 | CH₂(2-MePr^c) | Me | CO₂H | O | 2-FPh |
| 449 | CH=CHCH₃ | Me | CO₂H | O | 4-FPh |
| 450 | CH₂CH=CH₂ | Me | CO₂H | O | 4-FPh |
| 451 | CH₂CH=CHCH₃ | Me | CO₂H | O | 4-FPh |
| 452 | Pr^c | Me | CO₂H | O | 4-FPh |
| 453 | 2-MePr^c | Me | CO₂H | O | 4-FPh |
| 454 | CH₂Pr^c | Me | CO₂H | O | 4-FPh |
| 455 | CH₂(2-MePr^c) | Me | CO₂H | O | 4-FPh |
| 456 | CH₂Bu^c | Me | CO₂H | O | 4-FPh |
| 457 | CH₂Pn^c | Me | CO₂H | O | 4-FPh |
| 458 | CH₂Hx^c | Me | CO₂H | O | 4-FPh |
| 459 | CH₂CH=CHCH₃ | Me | CO₂H | O | 2,4-diFPh |
| 460 | CH₂Pr^c | Me | CO₂H | O | 2,4-diFPh |
| 461 | CH₂(2-MePr^c) | Me | CO₂H | O | 2,4-diFPh |
| 462 | CH₂CH=CHCH₃ | Me | CO₂H | O | 2-ClPh |
| 463 | CH₂Pr^c | Me | CO₂H | O | 2-ClPh |
| 464 | CH₂(2-MePr^c) | Me | CO₂H | O | 2-ClPh |
| 465 | CH₂CH=CHCH₃ | Me | CO₂H | O | 4-ClPh |
| 466 | CH₂Pr^c | Me | CO₂H | O | 4-ClPh |
| 467 | CH₂(2-MePr^c) | Me | CO₂H | O | 4-ClPh |
| 468 | CH₂CH=CHCH₃ | Me | CO₂H | O | 2-F,4-ClPh |
| 469 | CH₂Pr^c | Me | CO₂H | O | 2-F,4-ClPh |
| 470 | CH₂(2-MePr^c) | Me | CO₂H | O | 2-F,4-ClPh |
| 471 | CH₂CH=CHCH₃ | Me | CO₂H | O | 2-Cl,4-FPh |
| 472 | CH₂Pr^c | Me | CO₂H | O | 2-Cl,4-FPh |
| 473 | CH₂(2-MePr^c) | Me | CO₂H | O | 2-Cl,4-FPh |
| 474 | CH₂CH=CHCH₃ | Me | CO₂H | O | 2,4-diClPh |

TABLE 1-continued (I)

| Exemp. Comp. No. | R¹ | R² | R³ | A | R⁴ |
|---|---|---|---|---|---|
| 475 | CH₂Pr^c | Me | CO₂H | O | 2,4-diClPh |
| 476 | CH₂(2-MePr^c) | Me | CO₂H | O | 2,4-diClPh |
| 477 | CH₂CH=CHCH₃ | Me | CO₂Me | O | Ph |
| 478 | CH₂(2-MePr^c) | Me | CO₂Me | O | Ph |
| 479 | CH₂CH=CHCH₃ | Me | CO₂Me | O | 2-FPh |
| 480 | CH₂(2-MePr^c) | Me | CO₂Me | O | 2-FPh |
| 481 | CH=CHCH₃ | Me | CO₂Me | O | 4-FPh |
| 482 | CH₂CH=CH₂ | Me | CO₂Me | O | 4-FPh |
| 483 | CH₂CH=CHCH₃ | Me | CO₂Me | O | 4-FPh |
| 484 | CH₂Pr^c | Me | CO₂Me | O | 4-FPh |
| 485 | CH₂(2-MePr^c) | Me | CO₂Me | O | 4-FPh |
| 486 | CH₂CH=CHCH₃ | Me | CO₂Me | O | 2,4-diFPh |
| 487 | CH₂Pr^c | Me | CO₂Me | O | 2,4-diFPh |
| 488 | CH₂(2-MePr^c) | Me | CO₂Me | O | 2,4-diFPh |
| 489 | CH₂CH=CHCH₃ | Me | CO₂Me | O | 2-ClPh |
| 490 | CH₂(2-MePr^c) | Me | CO₂Me | O | 2-ClPh |
| 491 | CH₂CH=CHCH₃ | Me | CO₂Me | O | 4-ClPh |
| 492 | CH₂(2-MePr^c) | Me | CO₂Me | O | 4-ClPh |
| 493 | CH₂CH=CHCH₃ | Me | CO₂Me | O | 2-F,4-ClPh |
| 494 | CH₂(2-MePr^c) | Me | CO₂Me | O | 2-F,4-ClPh |
| 495 | CH₂CH=CHCH₃ | Me | CO₂Me | O | 2-Cl,4-FPh |
| 496 | CH₂(2-MePr^c) | Me | CO₂Me | O | 2-Cl,4-FPh |
| 497 | CH₂CH=CHCH₃ | Me | CO₂Me | O | 2,4-diClPh |
| 498 | CH₂(2-MePr^c) | Me | CO₂Me | O | 2,4-diClPh |
| 499 | CH₂CH=CHCH₃ | Me | CO₂Et | O | Ph |
| 500 | CH₂(2-MePr^c) | Me | CO₂Et | O | Ph |
| 501 | CH₂CH=CHCH₃ | Me | CO₂Et | O | 2-FPh |
| 502 | CH₂(2-MePr^c) | Me | CO₂Et | O | 2-FPh |
| 503 | CH₂CH=CH₂ | Me | CO₂Et | O | 4-FPh |
| 504 | CH₂CH=CHCH₃ | Me | CO₂Et | O | 4-FPh |
| 505 | CH₂Pr^c | Me | CO₂Et | O | 4-FPh |
| 506 | CH₂(2-MePr^c) | Me | CO₂Et | O | 4-FPh |
| 507 | CH₂CH=CHCH₃ | Me | CO₂Et | O | 2,4-diFPh |
| 508 | CH₂(2-MePr^c) | Me | CO₂Et | O | 2,4-diFPh |
| 509 | CH₂CH=CHCH₃ | Me | CO₂Et | O | 2-ClPh |
| 510 | CH₂(2-MePr^c) | Me | CO₂Et | O | 2-ClPh |
| 511 | CH₂CH=CHCH₃ | Me | CO₂Et | O | 4-ClPh |
| 512 | CH₂(2-MePr^c) | Me | CO₂Et | O | 4-ClPh |
| 513 | CH₂CH=CHCH₃ | Me | CO₂Et | O | 2-F,4-ClPh |
| 514 | CH₂(2-MePr^c) | Me | CO₂Et | O | 2-F,4-ClPh |
| 515 | CH₂CH=CHCH₃ | Me | CO₂Et | O | 2-Cl,4-FPh |
| 516 | CH₂(2-MePr^c) | Me | CO₂Et | O | 2-Cl,4-FPh |
| 517 | CH₂CH=CHCH₃ | Me | CO₂Et | O | 2,4-diClPh |
| 518 | CH₂(2-MePr^c) | Me | CO₂Et | O | 2,4-diClPh |
| 519 | CH₂(2-MePr^c) | Me | CO₂Pr | O | Ph |
| 520 | CH₂(2-MePr^c) | Me | CO₂Bu | O | Ph |
| 521 | CH₂CH=CHCH₃ | Me | CO₂Pr | O | 2-FPh |
| 522 | CH₂CH=CHCH₃ | Me | CO₂Bu | O | 2-FPh |
| 523 | CH₂CH=CHCH₃ | Me | CO₂Ph | O | 2-FPh |
| 524 | CH₂(2-MePr^c) | Me | CO₂Pr | O | 2-FPh |
| 525 | CH₂(2-MePr^c) | Me | CO₂Bu | O | 2-FPh |
| 526 | CH₂(2-MePr^c) | Me | CO₂Ph | O | 2-FPh |
| 527 | CH₂(2-MePr^c) | Me | CO₂(4-Me)Ph | O | 2-FPh |
| 528 | CH₂CH=CH₂ | Me | CO₂Pr | O | 4-FPh |
| 529 | CH₂CH=CH₂ | Me | CO₂Bu | O | 4-FPh |
| 530 | CH₂CH=CH₂ | Me | CO₂Ph | O | 4-FPh |
| 531 | CH₂CH=CH₂ | Me | CO₂(4-Me)Ph | O | 4-FPh |
| 532 | CH₂CH=CHCH₃ | Me | CO₂Pr | O | 4-FPh |
| 533 | CH₂CH=CHCH₃ | Me | CO₂Bu | O | 4-FPh |
| 534 | CH₂CH=CHCH₃ | Me | CO₂Ph | O | 4-FPh |
| 535 | CH₂Pr^c | Me | CO₂Pr | O | 4-FPh |
| 536 | CH₂Pr^c | Me | CO₂Bu | O | 4-FPh |
| 537 | CH₂Pr^c | Me | CO₂Ph | O | 4-FPh |

TABLE 1-continued

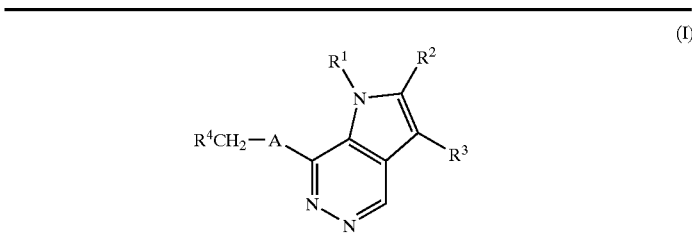

| Exemp. Comp. No. | $R^1$ | $R^2$ | $R^3$ | A | $R^4$ |
|---|---|---|---|---|---|
| 538 | $CH_2Pr^c$ | Me | $CO_2$(4-Me)Ph | O | 4-FPh |
| 539 | $CH_2$(2-$MePr^c$) | Me | $CO_2Pr$ | O | 4-FPh |
| 540 | $CH_2$(2-$MePr^c$) | Me | $CO_2Bu$ | O | 4-FPh |
| 541 | $CH_2$(2-$MePr^c$) | Me | $CO_2Ph$ | O | 4-FPh |
| 542 | $CH_2$(2-$MePr^c$) | Me | $CO_2$(4-Me)Ph | O | 4-FPh |
| 543 | $CH_2$(2-$MePr^c$) | Me | $CO_2$(4-MeO)Ph | O | 4-FPh |
| 544 | $CH_2$(2-$MePr^c$) | Me | $CO_2$(4-F)Ph | O | 4-FPh |
| 545 | $CH_2$(2-$MePr^c$) | Me | $CO_2$(4-Cl)Ph | O | 4-FPh |
| 546 | $CH_2CH=CHCH_3$ | Me | $CO_2Pr$ | O | 2,4-diFPh |
| 547 | $CH_2CH=CHCH_3$ | Me | $CO_2Bu$ | O | 2,4-diFPh |
| 548 | $CH_2$(2-$MePr^c$) | Me | $CO_2Pr$ | O | 2,4-diFPh |
| 549 | $CH_2$(2-$MePr^c$) | Me | $CO_2Bu$ | O | 2,4-diFPh |
| 550 | $CH_2$(2-$MePr^c$) | Me | $CO_2Ph$ | O | 2,4-diFPh |
| 551 | $CH_2CH=CHCH_3$ | Me | $CO_2Pr$ | O | 2-ClPh |
| 552 | $CH_2CH=CHCH_3$ | Me | $CO_2Bu$ | O | 2-ClPh |
| 553 | $CH_2$(2-$MePr^c$) | Me | $CO_2Pr$ | O | 2-ClPh |
| 554 | $CH_2$(2-$MePr^c$) | Me | $CO_2Bu$ | O | 2-ClPh |
| 555 | $CH_2$(2-$MePr^c$) | Me | $CO_2Ph$ | O | 2-ClPh |
| 556 | $CH_2CH=CHCH_3$ | Me | $CO_2Pr$ | O | 4-ClPh |
| 557 | $CH_2CH=CHCH_3$ | Me | $CO_2Bu$ | O | 4-ClPh |
| 558 | $CH_2$(2-$MePr^c$) | Me | $CO_2Pr$ | O | 4-ClPh |
| 559 | $CH_2$(2-$MePr^c$) | Me | $CO_2Bu$ | O | 4-ClPh |
| 560 | $CH_2$(2-$MePr^c$) | Me | $CO_2Ph$ | O | 4-ClPh |
| 561 | $CH_2CH=CHCH_3$ | Me | $CO_2Pr$ | O | 2-F,4-ClPh |
| 562 | $CH_2$(2-$MePr^c$) | Me | $CO_2Pr$ | O | 2-F,4-ClPh |
| 563 | $CH_2CH=CH_2$ | Me | $CO_2Pr$ | O | 2-Cl,4-FPh |
| 564 | $CH_2$(2-$MePr^c$) | Me | $CO_2Pr$ | O | 2-Cl,4-FPh |
| 565 | $CH_2CH=CH_2$ | Me | $CO_2Pr$ | O | 2,4-diClPh |
| 566 | $CH_2$(2-$MePr^c$) | Me | $CO_2Pr$ | O | 2,4-diClPh |
| 567 | $CH_2CH=CH_2$ | Et | $CH_2OH$ | O | Ph |
| 568 | $CH_2CH=CH_2$ | Pr | $CH_2OH$ | O | Ph |
| 569 | $CH_2Pr^c$ | Et | $CH_2OH$ | O | Ph |
| 570 | $CH_2Pr^c$ | Pr | $CH_2OH$ | O | Ph |
| 571 | $CH_2$(2-$MePr^c$) | Et | $CH_2OH$ | O | Ph |
| 572 | $CH_2$(2-$MePr^c$) | Pr | $CH_2OH$ | O | Ph |
| 573 | $CH=CHCH_3$ | Et | $CH_2OH$ | O | 2-FPh |
| 574 | $CH_2CH=CH_2$ | Et | $CH_2OH$ | O | 2-FPh |
| 575 | $CH_2CH=CH_2$ | Pr | $CH_2OH$ | O | 2-FPh |
| 576 | $CH_2CH=CHCH_3$ | Et | $CH_2OH$ | O | 2-FPh |
| 577 | $CH_2Pr^c$ | Et | $CH_2OH$ | O | 2-FPh |
| 578 | $CH_2Pr^c$ | Pr | $CH_2OH$ | O | 2-FPh |
| 579 | $CH_2$(2-$MePr^c$) | Et | $CH_2OH$ | O | 2-FPh |
| 580 | $CH_2$(2-$MePr^c$) | Pr | $CH_2OH$ | O | 2-FPh |
| 581 | $CH_2$(2-$MePr^c$) | Bu | $CH_2OH$ | O | 2-FPh |
| 582 | $CH=CH_2$ | Et | $CH_2OH$ | O | 4-FPh |
| 583 | $CH=CHCH_3$ | Et | $CH_2OH$ | O | 4-FPh |
| 584 | $CH=CHCH_3$ | Pr | $CH_2OH$ | O | 4-FPh |
| 585 | $CH_2CH=CH_2$ | Et | $CH_2OH$ | O | 4-FPh |
| 586 | $CH_2CH=CH_2$ | Pr | $CH_2OH$ | O | 4-FPh |
| 587 | $CH_2CH=CH_2$ | Bu | $CH_2OH$ | O | 4-FPh |
| 588 | $CH_2C(CH_3)=CH_2$ | Et | $CH_2OH$ | O | 4-FPh |
| 589 | $CH_2CH=CHCH_3$ | Et | $CH_2OH$ | O | 4-FPh |
| 590 | $CH_2CH=CHCH_3$ | Pr | $CH_2OH$ | O | 4-FPh |
| 591 | $CH_2CH=CF_2$ | Et | $CH_2OH$ | O | 4-FPh |
| 592 | $CH_2Pr^c$ | Et | $CH_2OH$ | O | 4-FPh |
| 593 | $CH_2Pr^c$ | Pr | $CH_2OH$ | O | 4-FPh |
| 594 | $CH_2$(2-$MePr^c$) | Et | $CH_2OH$ | O | 4-FPh |
| 595 | $CH_2$(2-$MePr^c$) | Pr | $CH_2OH$ | O | 4-FPh |
| 596 | $CH_2$(2-$MePr^c$) | Bu | $CH_2OH$ | O | 4-FPh |
| 597 | $CH_2Pn^c$ | Et | $CH_2OH$ | O | 4-FPh |
| 598 | $CH_2Hx^c$ | Et | $CH_2OH$ | O | 4-FPh |
| 599 | $CH=CHCH_3$ | Et | $CH_2OH$ | O | 2,4-diFPh |
| 600 | $CH_2CH=CH_2$ | Et | $CH_2OH$ | O | 2,4-diFPh |

TABLE 1-continued

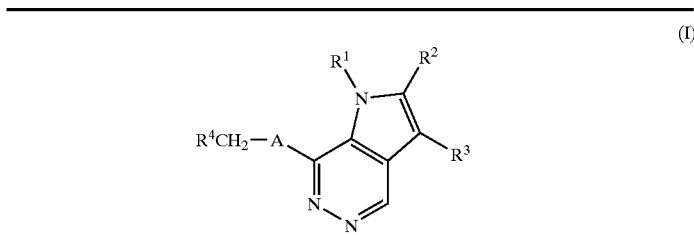

(I)

| Exemp. Comp. No. | R¹ | R² | R³ | A | R⁴ |
|---|---|---|---|---|---|
| 601 | CH₂CH=CH₂ | Pr | CH₂OH | O | 2,4-diFPh |
| 602 | CH₂CH=CHCH₃ | Et | CH₂OH | O | 2,4-diFPh |
| 603 | CH₂CH=CF₂ | Et | CH₂OH | O | 2,4-diFPh |
| 604 | CH₂Pr^c | Et | CH₂OH | O | 2,4-diFPh |
| 605 | CH₂Pr^c | Pr | CH₂OH | O | 2,4-diFPh |
| 606 | CH₂(2-MePr^c) | Et | CH₂OH | O | 2,4-diFPh |
| 607 | CH₂(2-MePr^c) | Pr | CH₂OH | O | 2,4-diFPh |
| 608 | CH₂(2-MePr^c) | Bu | CH₂OH | O | 2,4-diFPh |
| 609 | CH₂CH=CH₂ | Et | CH₂OAc | O | Ph |
| 610 | CH₂Pr^c | Et | CH₂OAc | O | Ph |
| 611 | CH₂(2-MePr^c) | Et | CH₂OAc | O | Ph |
| 612 | CH₂(2-MePr^c) | Pr | CH₂OAc | O | Ph |
| 613 | CH₂CH=CH₂ | Et | CH₂OAc | O | 2-FPh |
| 614 | CH₂Pr^c | Et | CH₂OAc | O | 2-FPh |
| 615 | CH₂(2-MePr^c) | Et | CH₂OAc | O | 2-FPh |
| 616 | CH₂(2-MePr^c) | Pr | CH₂OAc | O | 2-FPh |
| 617 | CH=CH₂ | Et | CH₂OAc | O | 4-FPh |
| 618 | CH=CHCH₃ | Et | CH₂OAc | O | 4-FPh |
| 619 | CH₂CH=CH₂ | Et | CH₂OAc | O | 4-FPh |
| 620 | CH₂CH=CH₂ | Pr | CH₂OAc | O | 4-FPh |
| 621 | CH₂CH=CHCH₃ | Et | CH₂OAc | O | 4-FPh |
| 622 | CH₂CH=CF₂ | Et | CH₂OAc | O | 4-FPh |
| 623 | CH₂Pr^c | Et | CH₂OAc | O | 4-FPh |
| 624 | CH₂Pr^c | Pr | CH₂OAc | O | 4-FPh |
| 625 | CH₂(2-MePr^c) | Et | CH₂OAc | O | 4-FPh |
| 626 | CH₂(2-MePr^c) | Pr | CH₂OAc | O | 4-FPh |
| 627 | CH₂(2-MePr^c) | Bu | CH₂OAc | O | 4-FPh |
| 628 | CH₂CH=CH₂ | Et | CH₂OAc | O | 2,4-diFPh |
| 629 | CH₂CH=CHCH₃ | Et | CH₂OAc | O | 2,4-diFPh |
| 630 | CH₂CH=CF₂ | Et | CH₂OAc | O | 2,4-diFPh |
| 631 | CH₂Pr^c | Et | CH₂OAc | O | 2,4-diFPh |
| 632 | CH₂Pr^c | Pr | CH₂OAc | O | 2,4-diFPh |
| 633 | CH₂(2-MePr^c) | Et | CH₂OAc | O | 2,4-diFPh |
| 634 | CH₂(2-MePr^c) | Pr | CH₂OAc | O | 2,4-diFPh |
| 635 | CH₂CH=CH₂ | Et | CHO | O | Ph |
| 636 | CH₂CH=CH₂ | Et | CO₂H | O | Ph |
| 637 | CH₂Pr^c | Et | CHO | O | Ph |
| 638 | CH₂Pr^c | Et | CO₂H | O | Ph |
| 639 | CH₂(2-MePr^c) | Et | CHO | O | Ph |
| 640 | CH₂(2-MePr^c) | Et | CO₂H | O | Ph |
| 641 | CH₂CH=CH₂ | Et | CHO | O | 2-FPh |
| 642 | CH₂CH=CH₂ | Et | CO₂H | O | 2-FPh |
| 643 | CH₂Pr^c | Et | CHO | O | 2-FPh |
| 644 | CH₂Pr^c | Et | CO₂H | O | 2-FPh |
| 645 | CH₂(2-MePr^c) | Et | CHO | O | 2-FPh |
| 646 | CH₂(2-MePr^c) | Et | CO₂H | O | 2-FPh |
| 647 | CH=CHCH₃ | Et | CHO | O | 4-FPh |
| 648 | CH=CHCH₃ | Et | CO₂H | O | 4-FPh |
| 649 | CH₂CH=CH₂ | Et | CHO | O | 4-FPh |
| 650 | CH₂CH=CH₂ | Et | CO₂H | O | 4-FPh |
| 651 | CH₂CH=CH₂ | Et | CO₂Me | O | 4-FPh |
| 652 | CH₂CH=CH₂ | Et | CO₂Et | O | 4-FPh |
| 653 | CH₂CH=CH₂ | Pr | CHO | O | 4-FPh |
| 654 | CH₂CH=CH₂ | Pr | CO₂H | O | 4-FPh |
| 655 | CH₂CH=CHCH₃ | Et | CHO | O | 4-FPh |
| 656 | CH₂CH=CHCH₃ | Et | CO₂H | O | 4-FPh |
| 657 | CH₂CH=CF₂ | Et | CHO | O | 4-FPh |
| 658 | CH₂CH=CF₂ | Et | CO₂H | O | 4-FPh |
| 659 | CH₂Pr^c | Et | CHO | O | 4-FPh |
| 660 | CH₂Pr^c | Et | CO₂H | O | 4-FPh |
| 661 | CH₂Pr^c | Et | CO₂Me | O | 4-FPh |
| 662 | CH₂Pr^c | Et | CO₂Et | O | 4-FPh |
| 663 | CH₂Pr^c | Pr | CHO | O | 4-FPh |

TABLE 1-continued

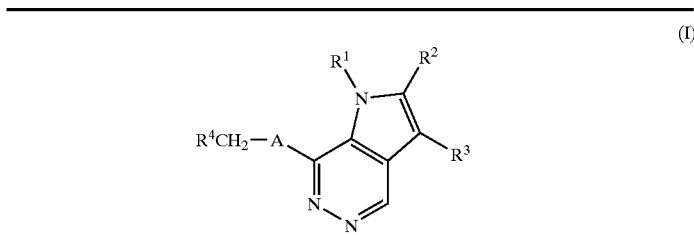

| Exemp. Comp. No. | R¹ | R² | R³ | A | R⁴ |
|---|---|---|---|---|---|
| 664 | CH₂Pr$^c$ | Pr | CO₂H | O | 4-FPh |
| 665 | CH₂(2-MePr$^c$) | Et | CHO | O | 4-FPh |
| 666 | CH₂(2-MePr$^c$) | Et | CO₂H | O | 4-FPh |
| 667 | CH₂(2-MePr$^c$) | Et | CO₂Me | O | 4-FPh |
| 668 | CH₂(2-MePr$^c$) | Et | CO₂Et | O | 4-FPh |
| 669 | CH₂(2-MePr$^c$) | Pr | CHO | O | 4-FPh |
| 670 | CH₂(2-MePr$^c$) | Pr | CO₂H | O | 4-FPh |
| 671 | CH₂(2-MePr$^c$) | Bu | CHO | O | 4-FPh |
| 672 | CH₂(2-MePr$^c$) | Bu | CO₂H | O | 4-FPh |
| 673 | CH₂CH=CH₂ | Et | CHO | O | 2,4-diFPh |
| 674 | CH₂CH=CH₂ | Et | CO₂H | O | 2,4-diFPh |
| 675 | CH₂CH=CHCH₃ | Et | CHO | O | 2,4-diFPh |
| 676 | CH₂CH=CHCH₃ | Et | CO₂H | O | 2,4-diFPh |
| 677 | CH₂CH=CF₂ | Et | CHO | O | 2,4-diFPh |
| 678 | CH₂CH=CF₂ | Et | CO₂H | O | 2,4-diFPh |
| 679 | CH₂Pr$^c$ | Et | CHO | O | 2,4-diFPh |
| 680 | CH₂Pr$^c$ | Et | CO₂H | O | 2,4-diFPh |
| 681 | CH₂(2-MePr$^c$) | Et | CHO | O | 2,4-diFPh |
| 682 | CH₂(2-MePr$^c$) | Et | CO₂H | O | 2,4-diFPh |
| 683 | CH₂(2-MePr$^c$) | Et | CO₂Me | O | 2,4-diFPh |
| 684 | CH₂(2-MePr$^c$) | Et | CO₂Et | O | 2,4-diFPh |
| 685 | CH₂(2-MePr$^c$) | Pr | CHO | O | 2,4-diFPh |
| 686 | CH₂(2-MePr$^c$) | Pr | CO₂H | O | 2,4-diFPh |
| 687 | CH₂CH=CH₂ | Me | CH₂OH | O | 4-MePh |
| 688 | CH₂CH=CH₂ | Me | CH₂OH | O | 4-CF₃Ph |
| 689 | CH₂CH=CH₂ | Me | CH₂OH | O | 4-MeOPh |
| 690 | CH₂CH=CH₂ | Me | CH₂OH | O | 4-CHF₂OPh |
| 691 | CH₂CH=CH₂ | Me | CH₂OH | O | 4-CF₃OPh |
| 692 | CH₂CH=CH₂ | Me | CH₂OH | O | 4-BrPh |
| 693 | CH₂CH=CHCH₃ | Me | CH₂OH | O | 4-CF₃Ph |
| 694 | CH₂CH=CHCH₃ | Me | CH₂OH | O | 4-CHF₂OPh |
| 695 | CH₂CH=CHCH₃ | Me | CH₂OH | O | 4-CF₃OPh |
| 696 | CH₂Pr$^c$ | Me | CH₂OH | O | 4-MePh |
| 697 | CH₂Pr$^c$ | Me | CH₂OH | O | 4-CF₃Ph |
| 698 | CH₂Pr$^c$ | Me | CH₂OH | O | 4-MeOPh |
| 699 | CH₂Pr$^c$ | Me | CH₂OH | O | 4-CHF₂OPh |
| 700 | CH₂Pr$^c$ | Me | CH₂OH | O | 4-CF₃OPh |
| 701 | CH₂Pr$^c$ | Me | CH₂OH | O | 4-BrPh |
| 702 | CH₂(2-MePr$^c$) | Me | CH₂OH | O | 4-MePh |
| 703 | CH₂(2-MePr$^c$) | Me | CH₂OH | O | 4-CF₃Ph |
| 704 | CH₂(2-MePr$^c$) | Me | CH₂OH | O | 4-MeOPh |
| 705 | CH₂(2-MePr$^c$) | Me | CH₂OH | O | 4-CHF₂OPh |
| 706 | CH₂(2-MePr$^c$) | Me | CH₂OH | O | 4-CF₃OPh |
| 707 | CH₂(2-MePr$^c$) | Me | CH₂OH | O | 4-BrPh |
| 708 | CH₂CH=CH₂ | Me | CH₂OAc | O | 4-MePh |
| 709 | CH₂CH=CH₂ | Me | CH₂OAc | O | 4-CF₃Ph |
| 710 | CH₂CH=CH₂ | Me | CH₂OAc | O | 4-MeOPh |
| 711 | CH₂CH=CH₂ | Me | CH₂OAc | O | 4-CHF₂OPh |
| 712 | CH₂CH=CH₂ | Me | CH₂OAc | O | 4-CF₃OPh |
| 713 | CH₂CH=CH₂ | Me | CH₂OAc | O | 4-BrPh |
| 714 | CH₂CH=CHCH₃ | Me | CH₂OAc | O | 4-CF₃Ph |
| 715 | CH₂CH=CHCH₃ | Me | CH₂OAc | O | 4-CHF₂OPh |
| 716 | CH₂CH=CHCH₃ | Me | CH₂OAc | O | 4-CF₃OPh |
| 717 | CH₂Pr$^c$ | Me | CH₂OAc | O | 4-MePh |
| 718 | CH₂Pr$^c$ | Me | CH₂OAc | O | 4-CF₃Ph |
| 719 | CH₂Pr$^c$ | Me | CH₂OAc | O | 4-MeOPh |
| 720 | CH₂Pr$^c$ | Me | CH₂OAc | O | 4-CHF₂OPh |
| 721 | CH₂Pr$^c$ | Me | CH₂OAc | O | 4-CF₃OPh |
| 722 | CH₂Pr$^c$ | Me | CH₂OAc | O | 4-BrPh |
| 723 | CH₂(2-MePr$^c$) | Me | CH₂OAc | O | 4-MePh |
| 724 | CH₂(2-MePr$^c$) | Me | CH₂OAc | O | 4-CF₃Ph |
| 725 | CH₂(2-MePr$^c$) | Me | CH₂OAc | O | 4-MeOPh |
| 726 | CH₂(2-MePr$^c$) | Me | CH₂OAc | O | 4-CHF₂OPh |

TABLE 1-continued

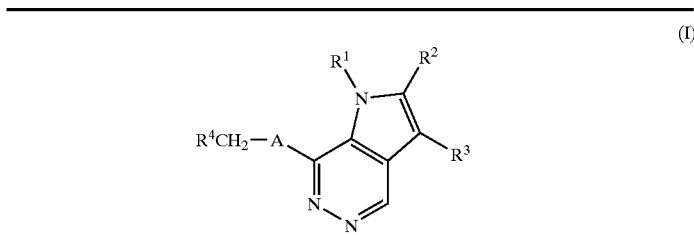

| Exemp. Comp. No. | $R^1$ | $R^2$ | $R^3$ | A | $R^4$ |
|---|---|---|---|---|---|
| 727 | $CH_2(2\text{-}MePr^c)$ | Me | $CH_2OAc$ | O | $4\text{-}CF_3OPh$ |
| 728 | $CH_2(2\text{-}MePr^c)$ | Me | $CH_2OAc$ | O | $4\text{-}BrPh$ |
| 729 | $CH_2CH=CH_2$ | Me | $CH_2OPrp$ | O | $4\text{-}CF_3Ph$ |
| 730 | $CH_2CH=CH_2$ | Me | $CH_2OBur$ | O | $4\text{-}CF_3Ph$ |
| 731 | $CH_2CH=CH_2$ | Me | $CH_2OCO_2Me$ | O | $4\text{-}CF_3Ph$ |
| 732 | $CH_2CH=CH_2$ | Me | $CH_2OCO_2Et$ | O | $4\text{-}CF_3Ph$ |
| 733 | $CH_2CH=CH_2$ | Me | CHO | O | $4\text{-}CF_3Ph$ |
| 734 | $CH_2CH=CH_2$ | Me | $CO_2H$ | O | $4\text{-}CF_3Ph$ |
| 735 | $CH_2CH=CH_2$ | Me | $CO_2Me$ | O | $4\text{-}CF_3Ph$ |
| 736 | $CH_2CH=CH_2$ | Me | $CO_2Et$ | O | $4\text{-}CF_3Ph$ |
| 737 | $CH_2CH=CH_2$ | Me | $CH_2OPrp$ | O | $4\text{-}CF_3OPh$ |
| 738 | $CH_2CH=CH_2$ | Me | $CH_2OBur$ | O | $4\text{-}CF_3OPh$ |
| 739 | $CH_2CH=CH_2$ | Me | $CH_2OCO_2Me$ | O | $4\text{-}CF_3OPh$ |
| 740 | $CH_2CH=CH_2$ | Me | $CH_2OCO_2Et$ | O | $4\text{-}CF_3OPh$ |
| 741 | $CH_2CH=CH_2$ | Me | CHO | O | $4\text{-}CF_3OPh$ |
| 742 | $CH_2CH=CH_2$ | Me | $CO_2H$ | O | $4\text{-}CF_3OPh$ |
| 743 | $CH_2CH=CH_2$ | Me | $CO_2Me$ | O | $4\text{-}CF_3OPh$ |
| 744 | $CH_2CH=CH_2$ | Me | $CO_2Et$ | O | $4\text{-}CF_3OPh$ |
| 745 | $CH_2Pr^c$ | Me | $CH_2OPrp$ | O | $4\text{-}CF_3Ph$ |
| 746 | $CH_2Pr^c$ | Me | $CH_2OBur$ | O | $4\text{-}CF_3Ph$ |
| 747 | $CH_2Pr^c$ | Me | $CH_2OCO_2Me$ | O | $4\text{-}CF_3Ph$ |
| 748 | $CH_2Pr^c$ | Me | $CH_2OCO_2Et$ | O | $4\text{-}CF_3Ph$ |
| 749 | $CH_2Pr^c$ | Me | CHO | O | $4\text{-}CF_3Ph$ |
| 750 | $CH_2Pr^c$ | Me | $CO_2H$ | O | $4\text{-}CF_3Ph$ |
| 751 | $CH_2Pr^c$ | Me | $CO_2Me$ | O | $4\text{-}CF_3Ph$ |
| 752 | $CH_2Pr^c$ | Me | $CO_2Et$ | O | $4\text{-}CF_3Ph$ |
| 753 | $CH_2Pr^c$ | Me | $CH_2OPrp$ | O | $4\text{-}CF_3OPh$ |
| 754 | $CH_2Pr^c$ | Me | $CH_2OBur$ | O | $4\text{-}CF_3OPh$ |
| 755 | $CH_2Pr^c$ | Me | $CH_2OCO_2Me$ | O | $4\text{-}CF_3OPh$ |
| 756 | $CH_2Pr^c$ | Me | $CH_2OCO_2Et$ | O | $4\text{-}CF_3OPh$ |
| 757 | $CH_2Pr^c$ | Me | CHO | O | $4\text{-}CF_3OPh$ |
| 758 | $CH_2Pr^c$ | Me | $CO_2H$ | O | $4\text{-}CF_3OPh$ |
| 759 | $CH_2Pr^c$ | Me | $CO_2Me$ | O | $4\text{-}CF_3OPh$ |
| 760 | $CH_2Pr^c$ | Me | $CO_2Et$ | O | $4\text{-}CF_3OPh$ |
| 761 | $CH_2(2\text{-}MePr^c)$ | Me | $CH_2OPrp$ | O | $4\text{-}MePh$ |
| 762 | $CH_2(2\text{-}MePr^c)$ | Me | $CH_2OBur$ | O | $4\text{-}MePh$ |
| 763 | $CH_2(2\text{-}MePr^c)$ | Me | $CH_2OCO_2Me$ | O | $4\text{-}MePh$ |
| 764 | $CH_2(2\text{-}MePr^c)$ | Me | $CH_2OCO_2Et$ | O | $4\text{-}MePh$ |
| 765 | $CH_2(2\text{-}MePr^c)$ | Me | CHO | O | $4\text{-}MePh$ |
| 766 | $CH_2(2\text{-}MePr^c)$ | Me | $CO_2H$ | O | $4\text{-}MePh$ |
| 767 | $CH_2(2\text{-}MePr^c)$ | Me | $CH_2OPrp$ | O | $4\text{-}CF_3Ph$ |
| 768 | $CH_2(2\text{-}MePr^c)$ | Me | $CH_2OBur$ | O | $4\text{-}CF_3Ph$ |
| 769 | $CH_2(2\text{-}MePr^c)$ | Me | $CH_2OCOPh$ | O | $4\text{-}CF_3Ph$ |
| 770 | $CH_2(2\text{-}MePr^c)$ | Me | $CH_2OCO_2Me$ | O | $4\text{-}CF_3Ph$ |
| 771 | $CH_2(2\text{-}MePr^c)$ | Me | $CH_2OCO_2Et$ | O | $4\text{-}CF_3Ph$ |
| 772 | $CH_2(2\text{-}MePr^c)$ | Me | $CH_2OCO_2Pr$ | O | $4\text{-}CF_3Ph$ |
| 773 | $CH_2(2\text{-}MePr^c)$ | Me | CHO | O | $4\text{-}CF_3Ph$ |
| 774 | $CH_2(2\text{-}MePr^c)$ | Me | $CO_2H$ | O | $4\text{-}CF_3Ph$ |
| 775 | $CH_2(2\text{-}MePr^c)$ | Me | $CO_2Me$ | O | $4\text{-}CF_3Ph$ |
| 776 | $CH_2(2\text{-}MePr^c)$ | Me | $CO_2Et$ | O | $4\text{-}CF_3Ph$ |
| 777 | $CH_2(2\text{-}MePr^c)$ | Me | $CO_2Ph$ | O | $4\text{-}CF_3Ph$ |
| 778 | $CH_2(2\text{-}MePr^c)$ | Me | $CH_2OPrp$ | O | $4\text{-}MeOPh$ |
| 779 | $CH_2(2\text{-}MePr^c)$ | Me | $CH_2OBur$ | O | $4\text{-}MeOPh$ |
| 780 | $CH_2(2\text{-}MePr^c)$ | Me | $CH_2OCO_2Me$ | O | $4\text{-}MeOPh$ |
| 781 | $CH_2(2\text{-}MePr^c)$ | Me | $CH_2OCO_2Et$ | O | $4\text{-}MeOPh$ |
| 782 | $CH_2(2\text{-}MePr^c)$ | Me | CHO | O | $4\text{-}MeOPh$ |
| 783 | $CH_2(2\text{-}MePr^c)$ | Me | $CO_2H$ | O | $4\text{-}MeOPh$ |
| 784 | $CH_2(2\text{-}MePr^c)$ | Me | $CH_2OPrp$ | O | $4\text{-}CHF_2OPh$ |
| 785 | $CH_2(2\text{-}MePr^c)$ | Me | $CH_2OBur$ | O | $4\text{-}CHF_2OPh$ |
| 786 | $CH_2(2\text{-}MePr^c)$ | Me | $CH_2OCO_2Me$ | O | $4\text{-}CHF_2OPh$ |
| 787 | $CH_2(2\text{-}MePr^c)$ | Me | $CH_2OCO_2Et$ | O | $4\text{-}CHF_2OPh$ |
| 788 | $CH_2(2\text{-}MePr^c)$ | Me | CHO | O | $4\text{-}CHF_2OPh$ |
| 789 | $CH_2(2\text{-}MePr^c)$ | Me | $CO_2H$ | O | $4\text{-}CHF_2OPh$ |

TABLE 1-continued (I)

| Exemp. Comp. No. | R¹ | R² | R³ | A | R⁴ |
|---|---|---|---|---|---|
| 790 | CH$_2$(2-MePr$^c$) | Me | CH$_2$OPrp | O | 4-CF$_3$OPh |
| 791 | CH$_2$(2-MePr$^c$) | Me | CH$_2$OBur | O | 4-CF$_3$OPh |
| 792 | CH$_2$(2-MePr$^c$) | Me | CH$_2$OCOPh | O | 4-CF$_3$OPh |
| 793 | CH$_2$(2-MePr$^c$) | Me | CH$_2$OCO$_2$Me | O | 4-CF$_3$OPh |
| 794 | CH$_2$(2-MePr$^c$) | Me | CH$_2$OCO$_2$Et | O | 4-CF$_3$OPh |
| 795 | CH$_2$(2-MePr$^c$) | Me | CH$_2$OCO$_2$Pr | O | 4-CF$_3$OPh |
| 796 | CH$_2$(2-MePr$^c$) | Me | CHO | O | 4-CF$_3$OPh |
| 797 | CH$_2$(2-MePr$^c$) | Me | CO$_2$H | O | 4-CF$_3$OPh |
| 798 | CH$_2$(2-MePr$^c$) | Me | CO$_2$Me | O | 4-CF$_3$OPh |
| 799 | CH$_2$(2-MePr$^c$) | Me | CO$_2$Et | O | 4-CF$_3$OPh |
| 800 | CH$_2$(2-MePr$^c$) | Me | CO$_2$Ph | O | 4-CF$_3$OPh |
| 801 | CH$_2$(2-MePr$^c$) | Me | CH$_2$OPrp | O | 4-BrPh |
| 802 | CH$_2$(2-MePr$^c$) | Me | CH$_2$OBur | O | 4-BrPh |
| 803 | CH$_2$(2-MePr$^c$) | Me | CH$_2$OCO$_2$Me | O | 4-BrPh |
| 804 | CH$_2$(2-MePr$^c$) | Me | CH$_2$OCO$_2$Et | O | 4-BrPh |
| 805 | CH$_2$(2-MePr$^c$) | Me | CHO | O | 4-BrPh |
| 806 | CH$_2$(2-MePr$^c$) | Me | CO$_2$H | O | 4-BrPh |
| 807 | CH$_2$CH=CH$_2$ | Me | CH$_2$OH | S | Ph |
| 808 | CH$_2$CH=CH$_2$ | Me | CH$_2$OH | NH | Ph |
| 809 | CH$_2$CH=CHCH$_3$ | Me | CH$_2$OH | S | Ph |
| 810 | CH$_2$Pr$^c$ | Me | CH$_2$OH | S | Ph |
| 811 | CH$_2$Pr$^c$ | Me | CH$_2$OH | NH | Ph |
| 812 | CH$_2$(2-MePr$^c$) | Me | CH$_2$OH | S | Ph |
| 813 | CH$_2$(2-MePr$^c$) | Me | CH$_2$OH | NH | Ph |
| 814 | CH$_2$CH=CH$_2$ | Me | CH$_2$OH | S | 2-FPh |
| 815 | CH$_2$CH=CH$_2$ | Me | CH$_2$OH | NH | 2-FPh |
| 816 | CH$_2$CH=CHCH$_3$ | Me | CH$_2$OH | S | 2-FPh |
| 817 | CH$_2$Pr$^c$ | Me | CH$_2$OH | S | 2-FPh |
| 818 | CH$_2$Pr$^c$ | Me | CH$_2$OH | NH | 2-FPh |
| 819 | CH$_2$(2-MePr$^c$) | Me | CH$_2$OH | S | 2-FPh |
| 820 | CH$_2$(2-MePr$^c$) | Me | CH$_2$OH | NH | 2-FPh |
| 821 | CH=CHCH$_3$ | Me | CH$_2$OH | S | 4-FPh |
| 822 | CH$_2$CH=CH$_2$ | Me | CH$_2$OH | S | 4-FPh |
| 823 | CH$_2$CH=CH$_2$ | Me | CH$_2$OH | NH | 4-FPh |
| 824 | CH$_2$C(CH$_3$)=CH$_2$ | Me | CH$_2$OH | S | 4-FPh |
| 825 | CH$_2$CH=CHCH$_3$ | Me | CH$_2$OH | S | 4-FPh |
| 826 | CH$_2$CH=CHCH$_3$ | Me | CH$_2$OH | NH | 4-FPh |
| 827 | CH$_2$CH=CF$_2$ | Me | CH$_2$OH | S | 4-FPh |
| 828 | CH$_2$CH=CHCl | Me | CH$_2$OH | S | 4-FPh |
| 829 | CH$_2$CH=CCl$_2$ | Me | CH$_2$OH | S | 4-FPh |
| 830 | Pr$^c$ | Me | CH$_2$OH | S | 4-FPh |
| 831 | 2-MePr$^c$ | Me | CH$_2$OH | S | 4-FPh |
| 832 | CH$_2$Pr$^c$ | Me | CH$_2$OH | S | 4-FPh |
| 833 | CH$_2$Pr$^c$ | Me | CH$_2$OH | NH | 4-FPh |
| 834 | CH$_2$(2-MePr$^c$) | Me | CH$_2$OH | S | 4-FPh |
| 835 | CH$_2$(2-MePr$^c$) | Me | CH$_2$OH | NH | 4-FPh |
| 836 | CH$_2$Bu$^c$ | Me | CH$_2$OH | S | 4-FPh |
| 837 | CH$_2$Pn$^c$ | Me | CH$_2$OH | S | 4-FPh |
| 838 | CH$_2$(2-MePn$^c$) | Me | CH$_2$OH | S | 4-FPh |
| 839 | CH$_2$Hx$^c$ | Me | CH$_2$OH | S | 4-FPh |
| 840 | CH$_2$(2-MeHx$^c$) | Me | CH$_2$OH | S | 4-FPh |
| 841 | CH$_2$CH=CH$_2$ | Me | CH$_2$OH | S | 2,4-diFPh |
| 842 | CH$_2$CH=CH$_2$ | Me | CH$_2$OH | NH | 2,4-diFPh |
| 843 | CH$_2$CH=CHCH$_3$ | Me | CH$_2$OH | S | 2,4-diFPh |
| 844 | CH$_2$CH=CHCH$_3$ | Me | CH$_2$OH | NH | 2,4-diFPh |
| 845 | CH$_2$Pr$^c$ | Me | CH$_2$OH | S | 2,4-diFPh |
| 846 | CH$_2$(2-MePr$^c$) | Me | CH$_2$OH | S | 2,4-diFPh |
| 847 | CH$_2$(2-MePr$^c$) | Me | CH$_2$OH | NH | 2,4-diFPh |
| 848 | CH$_2$Bu$^c$ | Me | CH$_2$OH | S | 2,4-diFPh |
| 849 | CH$_2$Pn$^c$ | Me | CH$_2$OH | S | 2,4-diFPh |
| 850 | CH$_2$Hx$^c$ | Me | CH$_2$OH | S | 2,4-diFPh |
| 851 | CH$_2$CH=CH$_2$ | Me | CH$_2$OH | S | 2-ClPh |
| 852 | CH$_2$Pr$^c$ | Me | CH$_2$OH | S | 2-ClPh |

TABLE 1-continued

Structure (I): R⁴CH₂—A— attached to a pyrrolo-pyridazine core with R¹ on N, R² and R³ on the pyrrole ring.

| Exemp. Comp. No. | R¹ | R² | R³ | A | R⁴ |
|---|---|---|---|---|---|
| 853 | CH₂(2-MePr^c) | Me | CH₂OH | S | 2-ClPh |
| 854 | CH₂(2-MePr^c) | Me | CH₂OH | NH | 2-ClPh |
| 855 | CH₂CH=CH₂ | Me | CH₂OH | S | 4-ClPh |
| 856 | CH₂CH=CHCH₃ | Me | CH₂OH | S | 4-ClPh |
| 857 | CH₂Pr^c | Me | CH₂OH | S | 4-ClPh |
| 858 | CH₂(2-MePr^c) | Me | CH₂OH | S | 4-ClPh |
| 859 | CH₂(2-MePr^c) | Me | CH₂OH | NH | 4-ClPh |
| 860 | CH₂CH=CH₂ | Me | CH₂OH | S | 2,4-diClPh |
| 861 | CH₂Pr^c | Me | CH₂OH | S | 2,4-diClPh |
| 862 | CH₂(2-MePr^c) | Me | CH₂OH | S | 2,4-diClPh |
| 863 | CH₂CH=CH₂ | Me | CH₂OAc | S | Ph |
| 864 | CH₂CH=CH₂ | Me | CH₂OAc | NH | Ph |
| 865 | CH₂CH=CHCH₃ | Me | CH₂OAc | S | Ph |
| 866 | CH₂Pr^c | Me | CH₂OAc | S | Ph |
| 867 | CH₂(2-MePr^c) | Me | CH₂OAc | S | Ph |
| 868 | CH₂(2-MePr^c) | Me | CH₂OAc | NH | Ph |
| 869 | CH₂CH=CH₂ | Me | CH₂OAc | S | 2-FPh |
| 870 | CH₂CH=CH₂ | Me | CH₂OAc | NH | 2-FPh |
| 871 | CH₂CH=CHCH₃ | Me | CH₂OAc | S | 2-FPh |
| 872 | CH₂Pr^c | Me | CH₂OAc | S | 2-FPh |
| 873 | CH₂(2-MePr^c) | Me | CH₂OAc | S | 2-FPh |
| 874 | CH₂(2-MePr^c) | Me | CH₂OAc | NH | 2-FPh |
| 875 | CH=CH₂ | Me | CH₂OAc | S | 4-FPh |
| 876 | CH=CHCH₃ | Me | CH₂OAc | S | 4-FPh |
| 877 | CH₂CH=CH₂ | Me | CH₂OAc | S | 4-FPh |
| 878 | CH₂CH=CH₂ | Me | CH₂OAc | NH | 4-FPh |
| 879 | CH₂C(CH₃)=CH₂ | Me | CH₂OAc | S | 4-FPh |
| 880 | CH₂CH=CHCH₃ | Me | CH₂OAc | S | 4-FPh |
| 881 | CH₂CH=CHCH₃ | Me | CH₂OAc | NH | 4-FPh |
| 882 | CH₂CH=CF₂ | Me | CH₂OAc | S | 4-FPh |
| 883 | CH₂CH=CHCl | Me | CH₂OAc | S | 4-FPh |
| 884 | CH₂CH=CCl₂ | Me | CH₂OAc | S | 4-FPh |
| 885 | Pr^c | Me | CH₂OAc | S | 4-FPh |
| 886 | 2-MePr^c | Me | CH₂OAc | S | 4-FPh |
| 887 | CH₂Pr^c | Me | CH₂OAc | S | 4-FPh |
| 888 | CH₂Pr^c | Me | CH₂OAc | NH | 4-FPh |
| 889 | CH₂(2-MePr^c) | Me | CH₂OAc | S | 4-FPh |
| 890 | CH₂(2-MePr^c) | Me | CH₂OAc | NH | 4-FPh |
| 891 | CH₂Bu^c | Me | CH₂OAc | S | 4-FPh |
| 892 | CH₂Pn^c | Me | CH₂OAc | S | 4-FPh |
| 893 | CH₂(2-MePn^c) | Me | CH₂OAc | S | 4-FPh |
| 894 | CH₂Hx^c | Me | CH₂OAc | S | 4-FPh |
| 895 | CH₂(2-MeHx^c) | Me | CH₂OAc | S | 4-FPh |
| 896 | CH₂CH=CH₂ | Me | CH₂OAc | S | 2,4-diFPh |
| 897 | CH₂CH=CH₂ | Me | CH₂OAc | NH | 2,4-diFPh |
| 898 | CH₂CH=CHCH₃ | Me | CH₂OAc | S | 2,4-diFPh |
| 899 | CH₂CH=CF₂ | Me | CH₂OAc | S | 2,4-diFPh |
| 900 | CH₂Pr^c | Me | CH₂OAc | S | 2,4-diFPh |
| 901 | CH₂(2-MePr^c) | Me | CH₂OAc | S | 2,4-diFPh |
| 902 | CH₂(2-MePr^c) | Me | CH₂OAc | NH | 2,4-diFPh |
| 903 | CH₂CH=CH₂ | Me | CH₂OAc | S | 2-ClPh |
| 904 | CH₂CH=CH₂ | Me | CH₂OAc | NH | 2-ClPh |
| 905 | CH₂CH=CHCH₃ | Me | CH₂OAc | S | 2-ClPh |
| 906 | CH₂Pr^c | Me | CH₂OAc | S | 2-ClPh |
| 907 | CH₂(2-MePr^c) | Me | CH₂OAc | S | 2-ClPh |
| 908 | CH₂(2-MePr^c) | Me | CH₂OAc | NH | 2-ClPh |
| 909 | CH₂CH=CH₂ | Me | CH₂OAc | S | 4-ClPh |
| 910 | CH₂CH=CH₂ | Me | CH₂OAc | NH | 4-ClPh |
| 911 | CH₂CH=CHCH₃ | Me | CH₂OAc | S | 4-ClPh |
| 912 | CH₂Pr^c | Me | CH₂OAc | S | 4-ClPh |
| 913 | CH₂(2-MePr^c) | Me | CH₂OAc | S | 4-ClPh |
| 914 | CH₂(2-MePr^c) | Me | CH₂OAc | NH | 4-ClPh |
| 915 | CH₂CH=CH₂ | Me | CH₂OAc | S | 2,4-diClPh |

TABLE 1-continued (I)

$$R^4CH_2-A-\text{[pyrrolopyridazine core with } R^1, R^2, R^3\text{]}$$

| Exemp. Comp. No. | R¹ | R² | R³ | A | R⁴ |
|---|---|---|---|---|---|
| 916 | CH$_2$Pr$^c$ | Me | CH$_2$OAc | S | 2,4-diClPh |
| 917 | CH$_2$(2-MePr$^c$) | Me | CH$_2$OAc | S | 2,4-diClPh |
| 918 | CH$_2$CH=CH$_2$ | Me | CH$_2$OPrp | S | Ph |
| 919 | CH$_2$Pr$^c$ | Me | CH$_2$OPrp | S | Ph |
| 920 | CH$_2$(2-MePr$^c$) | Me | CH$_2$OPrp | S | Ph |
| 921 | CH$_2$(2-MePr$^c$) | Me | CH$_2$OPrp | NH | Ph |
| 922 | CH$_2$CH=CH$_2$ | Me | CH$_2$OPrp | S | 2-FPh |
| 923 | CH$_2$Pr$^c$ | Me | CH$_2$OPrp | S | 2-FPh |
| 924 | CH$_2$(2-MePr$^c$) | Me | CH$_2$OPrp | S | 2-FPh |
| 925 | CH$_2$(2-MePr$^c$) | Me | CH$_2$OPrp | NH | 2-FPh |
| 926 | CH$_2$CH=CH$_2$ | Me | CH$_2$OPrp | S | 4-FPh |
| 927 | CH$_2$CH=CH$_2$ | Me | CH$_2$OPrp | NH | 4-FPh |
| 928 | CH$_2$CH=CHCH$_3$ | Me | CH$_2$OPrp | S | 4-FPh |
| 929 | CH$_2$Pr$^c$ | Me | CH$_2$OPrp | S | 4-FPh |
| 930 | CH$_2$(2-MePr$^c$) | Me | CH$_2$OPrp | S | 4-FPh |
| 931 | CH$_2$(2-MePr$^c$) | Me | CH$_2$OPrp | NH | 4-FPh |
| 932 | CH$_2$Bu$^c$ | Me | CH$_2$OPrp | S | 4-FPh |
| 933 | CH$_2$Pn$^c$ | Me | CH$_2$OPrp | S | 4-FPh |
| 934 | CH$_2$Hx$^c$ | Me | CH$_2$OPrp | S | 4-FPh |
| 935 | CH$_2$CH=CH$_2$ | Me | CH$_2$OPrp | S | 2,4-diFPh |
| 936 | CH$_2$CH=CH$_2$ | Me | CH$_2$OPrp | NH | 2,4-diFPh |
| 937 | CH$_2$CH=CHCH$_3$ | Me | CH$_2$OPrp | S | 2,4-diFPh |
| 938 | CH$_2$Pr$^c$ | Me | CH$_2$OPrp | S | 2,4-diFPh |
| 939 | CH$_2$(2-MePr$^c$) | Me | CH$_2$OPrp | S | 2,4-diFPh |
| 940 | CH$_2$(2-MePr$^c$) | Me | CH$_2$OPrp | NH | 2,4-diFPh |
| 941 | CH$_2$CH=CH$_2$ | Me | CH$_2$OPrp | S | 2-ClPh |
| 942 | CH$_2$Pr$^c$ | Me | CH$_2$OPrp | S | 2-ClPh |
| 943 | CH$_2$(2-MePr$^c$) | Me | CH$_2$OPrp | S | 2-ClPh |
| 944 | CH$_2$(2-MePr$^c$) | Me | CH$_2$OPrp | NH | 2-ClPh |
| 945 | CH$_2$CH=CH$_2$ | Me | CH$_2$OPrp | S | 4-ClPh |
| 946 | CH$_2$Pr$^c$ | Me | CH$_2$OPrp | S | 4-ClPh |
| 947 | CH$_2$(2-MePr$^c$) | Me | CH$_2$OPrp | S | 4-ClPh |
| 948 | CH$_2$(2-MePr$^c$) | Me | CH$_2$OPrp | NH | 4-ClPh |
| 949 | CH$_2$CH=CH$_2$ | Me | CH$_2$OPrp | S | 2,4-diClPh |
| 950 | CH$_2$Pr$^c$ | Me | CH$_2$OPrp | S | 2,4-diClPh |
| 951 | CH$_2$(2-MePr$^c$) | Me | CH$_2$OPrp | S | 2,4-diClPh |
| 952 | CH$_2$(2-MePr$^c$) | Me | CH$_2$OBur | S | Ph |
| 953 | CH$_2$CH=CH$_2$ | Me | CH$_2$OBur | S | 2-FPh |
| 954 | CH$_2$Pr$^c$ | Me | CH$_2$OBur | S | 2-FPh |
| 955 | CH$_2$(2-MePr$^c$) | Me | CH$_2$OBur | S | 2-FPh |
| 956 | CH$_2$CH=CH$_2$ | Me | CH$_2$OBur | S | 4-FPh |
| 957 | CH$_2$CH=CH$_2$ | Me | CH$_2$OBur | NH | 4-FPh |
| 958 | CH$_2$CH=CHCH$_3$ | Me | CH$_2$OBur | S | 4-FPh |
| 959 | Pr$^c$ | Me | CH$_2$OBur | S | 4-FPh |
| 960 | 2-MePr$^c$ | Me | CH$_2$OBur | S | 4-FPh |
| 961 | CH$_2$Pr$^c$ | Me | CH$_2$OBur | S | 4-FPh |
| 962 | CH$_2$(2-MePr$^c$) | Me | CH$_2$OBur | S | 4-FPh |
| 963 | CH$_2$(2-MePr$^c$) | Me | CH$_2$OBur | NH | 4-FPh |
| 964 | CH$_2$Bu$^c$ | Me | CH$_2$OBur | S | 4-FPh |
| 965 | CH$_2$Pn$^c$ | Me | CH$_2$OBur | S | 4-FPh |
| 966 | CH$_2$Hx$^c$ | Me | CH$_2$OBur | S | 4-FPh |
| 967 | CH$_2$CH=CH$_2$ | Me | CH$_2$OBur | S | 2,4-diFPh |
| 968 | CH$_2$CH=CH$_2$ | Me | CH$_2$OBur | NH | 2,4-diFPh |
| 969 | CH$_2$Pr$^c$ | Me | CH$_2$OBur | S | 2,4-diFPh |
| 970 | CH$_2$(2-MePr$^c$) | Me | CH$_2$OBur | S | 2,4-diFPh |
| 971 | CH$_2$(2-MePr$^c$) | Me | CH$_2$OBur | NH | 2,4-diFPh |
| 972 | CH$_2$CH=CH$_2$ | Me | CH$_2$OBur | S | 2-ClPh |
| 973 | CH$_2$Pr$^c$ | Me | CH$_2$OBur | S | 2-ClPh |
| 974 | CH$_2$(2-MePr$^c$) | Me | CH$_2$OBur | S | 2-ClPh |
| 975 | CH$_2$(2-MePr$^c$) | Me | CH$_2$OBur | NH | 2-ClPh |
| 976 | CH$_2$CH=CH$_2$ | Me | CH$_2$OBur | S | 4-ClPh |
| 977 | CH$_2$Pr$^c$ | Me | CH$_2$OBur | S | 4-ClPh |
| 978 | CH$_2$(2-MePr$^c$) | Me | CH$_2$OBur | S | 4-ClPh |

TABLE 1-continued

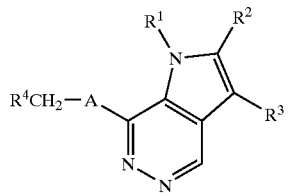

| Exemp. Comp. No. | R¹ | R² | R³ | A | R⁴ |
|---|---|---|---|---|---|
| 979 | CH₂(2-MePr$^c$) | Me | CH₂OBur | NH | 4-ClPh |
| 980 | CH₂CH=CH₂ | Me | CH₂OBur | S | 2,4-diClPh |
| 981 | CH₂Pr$^c$ | Me | CH₂OBur | S | 2,4-diClPh |
| 982 | CH₂(2-MePr$^c$) | Me | CH₂OBur | S | 2,4-diClPh |
| 983 | CH₂(2-MePr$^c$) | Me | CH₂OBur | NH | 2,4-diClPh |
| 984 | CH₂(2.MePr$^c$) | Me | CH₂OCOPh | S | Ph |
| 985 | CH₂CH=CH₂ | Me | CH₂OCOPh | S | 2-FPh |
| 986 | CH₂(2-MePr$^c$) | Me | CH₂OCOPh | S | 2-FPh |
| 987 | CH₂CH=CH₂ | Me | CH₂OCOPh | S | 4-FPh |
| 988 | CH₂CH=CHCH₃ | Me | CH₂OCOPh | S | 4-FPh |
| 989 | CH₂Pr$^c$ | Me | CH₂OCOPh | S | 4-FPh |
| 990 | CH₂(2-MePr$^c$) | Me | CH₂OCOPh | S | 4-FPh |
| 991 | CH₂(2-MePr$^c$) | Me | CH₂OCOPh | NH | 4-FPh |
| 992 | CH₂CH=CH₂ | Me | CH₂OCOPh | S | 2,4-diFPh |
| 993 | CH₂CH=CHCH₃ | Me | CH₂OCOPh | S | 2,4-diFPh |
| 994 | CH₂Pr$^c$ | Me | CH₂OCOPh | S | 2,4-diFPh |
| 995 | CH₂(2-MePr$^c$) | Me | CH₂OCOPh | S | 2,4-diFPh |
| 996 | CH₂(2-MePr$^c$) | Me | CH₂OCOPh | NH | 2,4-diFPh |
| 997 | CH₂CH=CH₂ | Me | CH₂OCOPh | S | 2-ClPh |
| 998 | CH₂(2-MePr$^c$) | Me | CH₂OCOPh | S | 2-ClPh |
| 999 | CH₂CH=CH₂ | Me | CH₂OCOPh | S | 4-ClPh |
| 1000 | CH₂Pr$^c$ | Me | CH₂OCOPh | S | 4-ClPh |
| 1001 | CH₂(2-MePr$^c$) | Me | CH₂OCOPh | S | 4-ClPh |
| 1002 | CH₂(2-MePr$^c$) | Me | CH₂OCOPh | NH | 4-ClPh |
| 1003 | CH₂CH=CH₂ | Me | CH₂OCOPh | S | 2,4-diClPh |
| 1004 | CH₂Pr$^c$ | Me | CH₂OCOPh | S | 2,4-diClPh |
| 1005 | CH₂(2-MePr$^c$) | Me | CH₂OCOPh | S | 2,4-diClPh |
| 1006 | CH₂(2-MePr$^c$) | Me | CH₂OCOPh | NH | 2,4-diClPh |
| 1007 | CH₂(2-MePr$^c$) | Me | CH₂OCO₂Me | S | Ph |
| 1008 | CH₂CH=CH₂ | Me | CH₂OCO₂Me | S | 2-FPh |
| 1009 | CH₂(2-MePr$^c$) | Me | CH₂OCO₂Me | S | 2-FPh |
| 1010 | CH₂CH=CH₂ | Me | CH₂OCO₂Me | S | 4-FPh |
| 1011 | CH₂CH=CH₂ | Me | CH₂OCO₂Me | NH | 4-FPh |
| 1012 | CH₂CH=CHCH₃ | Me | CH₂OCO₂Me | S | 4-FPh |
| 1013 | CH₂Pr$^c$ | Me | CH₂OCO₂Me | S | 4-FPh |
| 1014 | CH₂(2-MePr$^c$) | Me | CH₂OCO₂Me | S | 4-FPh |
| 1015 | CH₂(2-MePr$^c$) | Me | CH₂OCO₂Me | NH | 4-FPh |
| 1016 | CH₂CH=CH₂ | Me | CH₂OCO₂Me | S | 2,4-diFPh |
| 1017 | CH₂Pr$^c$ | Me | CH₂OCO₂Me | S | 2,4-diFPh |
| 1018 | CH₂(2-MePr$^c$) | Me | CH₂OCO₂Me | S | 2,4-diFPh |
| 1019 | CH₂(2-MePr$^c$) | Me | CH₂OCO₂Me | NH | 2,4-diFPh |
| 1020 | CH₂CH=CH₂ | Me | CH₂OCO₂Me | S | 2-ClPh |
| 1021 | CH₂(2-MePr$^c$) | Me | CH₂OCO₂Me | S | 2-ClPh |
| 1022 | CH₂CH=CH₂ | Me | CH₂OCO₂Me | S | 4-ClPh |
| 1023 | CH₂Pr$^c$ | Me | CH₂OCO₂Me | S | 4-ClPh |
| 1024 | CH₂(2-MePr$^c$) | Me | CH₂OCO₂Me | S | 4-ClPh |
| 1025 | CH₂(2-MePr$^c$) | Me | CH₂OCO₂Me | NH | 4-ClPh |
| 1026 | CH₂CH=CH₂ | Me | CH₂OCO₂Me | S | 2,4-diClPh |
| 1027 | CH₂Pr$^c$ | Me | CH₂OCO₂Me | S | 2,4-diClPh |
| 1028 | CH₂(2-MePr$^c$) | Me | CH₂OCO₂Me | S | 2,4-diClPh |
| 1029 | CH₂(2-MePr$^c$) | Me | CH₂OCO₂Me | NH | 2,4-diClPh |
| 1030 | CH₂(2-MePr$^c$) | Me | CH₂OCO₂Et | S | Ph |
| 1031 | CH₂CH=CH₂ | Me | CH₂OCO₂Et | S | 2-FPh |
| 1032 | CH₂(2-MePr$^c$) | Me | CH₂OCO₂Et | S | 2-FPh |
| 1033 | CH₂CH=CH₂ | Me | CH₂OCO₂Et | S | 4-FPh |
| 1034 | CH₂CH=CH₂ | Me | CH₂OCO₂Et | NH | 4-FPh |
| 1035 | CH₂CH=CHCH₃ | Me | CH₂OCO₂Et | S | 4-FPh |
| 1036 | CH₂Pr$^c$ | Me | CH₂OCO₂Et | S | 4-FPh |
| 1037 | CH₂(2-MePr$^c$) | Me | CH₂OCO₂Et | S | 4-FPh |
| 1038 | CH₂(2-MePr$^c$) | Me | CH₂OCO₂Et | NH | 4-FPh |
| 1039 | CH₂CH=CH₂ | Me | CH₂OCO₂Et | S | 2,4-diFPh |
| 1040 | CH₂Pr$^c$ | Me | CH₂OCO₂Et | S | 2,4-diFPh |
| 1041 | CH₂(2-MePr$^c$) | Me | CH₂OCO₂Et | S | 2,4-diFPh |

TABLE 1-continued

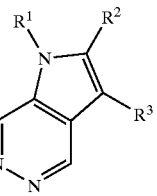

(I)

| Exemp. Comp. No. | R$^1$ | R$^2$ | R$^3$ | A | R$^4$ |
|---|---|---|---|---|---|
| 1042 | CH$_2$(2-MePr$^c$) | Me | CH$_2$OCO$_2$Et | NH | 2,4-diFPh |
| 1043 | CH$_2$CH=CH$_2$ | Me | CH$_2$OCO$_2$Et | S | 2-ClPh |
| 1044 | CH$_2$(2-MePr$^c$) | Me | CH$_2$OCO$_2$Et | S | 2-ClPh |
| 1045 | CH$_2$CH=CH$_2$ | Me | CH$_2$OCO$_2$Et | S | 4-ClPh |
| 1046 | CH$_2$Pr$^c$ | Me | CH$_2$OCO$_2$Et | S | 4-ClPh |
| 1047 | CH$_2$(2-MePr$^c$) | Me | CH$_2$OCO$_2$Et | S | 4-ClPh |
| 1048 | CH$_2$(2-MePr$^c$) | Me | CH$_2$OCO$_2$Et | NH | 4-ClPh |
| 1049 | CH$_2$CH=CH$_2$ | Me | CH$_2$OCO$_2$Et | S | 2,4-diClPh |
| 1050 | CH$_2$Pr$^c$ | Me | CH$_2$OCO$_2$Et | S | 2,4-diClPh |
| 1051 | CH$_2$(2-MePr$^c$) | Me | CH$_2$OCO$_2$Et | S | 2,4-diClPh |
| 1052 | CH$_2$(2-MePr$^c$) | Me | CH$_2$OCO$_2$Et | NH | 2,4-diClPh |
| 1053 | CH$_2$(2-MePr$^c$) | Me | CH$_2$OCO$_2$Pr | S | Ph |
| 1054 | CH$_2$(2-MePr$^c$) | Me | CH$_2$OCO$_2$Pr | S | 2-FPh |
| 1055 | CH$_2$CH=CH$_2$ | Me | CH$_2$OCO$_2$Pr | S | 4-FPh |
| 1056 | CH$_2$Pr$^c$ | Me | CH$_2$OCO$_2$Pr | S | 4-FPh |
| 1057 | CH$_2$(2-MePr$^c$) | Me | CH$_2$OCO$_2$Pr | S | 4-FPh |
| 1058 | CH$_2$(2-MePr$^c$) | Me | CH$_2$OCO$_2$Pr | NH | 4-FPh |
| 1059 | CH$_2$CH=CH$_2$ | Me | CH$_2$OCO$_2$Pr | S | 2,4-diFPh |
| 1060 | CH$_2$(2-MePr$^c$) | Me | CH$_2$OCO$_2$Pr | S | 2,4-diFPh |
| 1061 | CH$_2$(2-MePr$^c$) | Me | CH$_2$OCO$_2$Pr | NH | 2,4-diFPh |
| 1062 | CH$_2$(2-MePr$^c$) | Me | CH$_2$OCO$_2$Pr | S | 2-ClPh |
| 1063 | CH$_2$CH=CH$_2$ | Me | CH$_2$OCO$_2$Pr | S | 4-ClPh |
| 1064 | CH$_2$(2-MePr$^c$) | Me | CH$_2$OCO$_2$Pr | S | 4-ClPh |
| 1065 | CH$_2$CH=CH$_2$ | Me | CH$_2$OCO$_2$Pr | S | 2,4-diClPh |
| 1066 | CH$_2$(2-MePr$^c$) | Me | CH$_2$OCO$_2$Pr | S | 2,4-diClPh |
| 1067 | CH$_2$(2-MePr$^c$) | Me | CH$_2$OCO$_2$Pr | NH | 2,4-diClPh |
| 1068 | CH$_2$(2-MePr$^c$) | Me | CH$_2$OCO$_2$Bu | S | Ph |
| 1069 | CH$_2$(2-MePr$^c$) | Me | CH$_2$OCO$_2$Bu | S | 2-FPh |
| 1070 | CH$_2$CH=CH$_2$ | Me | CH$_2$OCO$_2$Bu | S | 4-FPh |
| 1071 | CH$_2$Pr$^c$ | Me | CH$_2$OCO$_2$Bu | S | 4-FPh |
| 1072 | CH$_2$(2-MePr$^c$) | Me | CH$_2$OCO$_2$Bu | S | 4-FPh |
| 1073 | CH$_2$(2-MePr$^c$) | Me | CH$_2$OCO$_2$Bu | NH | 4-FPh |
| 1074 | CH$_2$CH=CH$_2$ | Me | CH$_2$OCO$_2$Bu | S | 2,4-diFPh |
| 1075 | CH$_2$(2-MePr$^c$) | Me | CH$_2$OCO$_2$Bu | S | 2,4-diFPh |
| 1076 | CH$_2$(2-MePr$^c$) | Me | CH$_2$OCO$_2$Bu | NH | 2,4-diFPh |
| 1077 | CH$_2$(2-MePr$^c$) | Me | CH$_2$OCO$_2$Bu | S | 2-ClPh |
| 1078 | CH$_2$CH=CH$_2$ | Me | CH$_2$OCO$_2$Bu | S | 4-ClPh |
| 1079 | CH$_2$(2-MePr$^c$) | Me | CH$_2$OCO$_2$Bu | S | 4-ClPh |
| 1080 | CH$_2$CH=CH$_2$ | Me | CH$_2$OCO$_2$Bu | S | 2,4-diClPh |
| 1081 | CH$_2$(2-MePr$^c$) | Me | CH$_2$OCO$_2$Bu | S | 2,4-diClPh |
| 1082 | CH$_2$(2-MePr$^c$) | Me | CH$_2$OCO$_2$Bu | NH | 2,4-diClPh |
| 1083 | CH$_2$(2-MePr$^c$) | Me | CHO | S | Ph |
| 1084 | CH$_2$CH=CH$_2$ | Me | CHO | S | 2-FPh |
| 1085 | CH$_2$(2-MePr$^c$) | Me | CHO | S | 2-FPh |
| 1086 | CH$_2$CH=CH$_2$ | Me | CHO | S | 4-FPh |
| 1087 | CH$_2$CH=CH$_2$ | Me | CHO | NH | 4-FPh |
| 1088 | CH$_2$CH=CHCH$_3$ | Me | CHO | S | 4-FPh |
| 1089 | CH$_2$Pr$^c$ | Me | CHO | S | 4-FPh |
| 1090 | CH$_2$(2-MePr$^c$) | Me | CHO | S | 4-FPh |
| 1091 | CH$_2$(2-MePr$^c$) | Me | CHO | NH | 4-FPh |
| 1092 | CH$_2$CH=CH$_2$ | Me | CHO | S | 2,4-diFPh |
| 1093 | CH$_2$Pr$^c$ | Me | CHO | S | 2,4-diFPh |
| 1094 | CH$_2$(2-MePr$^c$) | Me | CHO | S | 2,4-diFPh |
| 1095 | CH$_2$(2-MePr$^c$) | Me | CHO | NH | 2,4-diFPh |
| 1096 | CH$_2$CH=CH$_2$ | Me | CHO | S | 2-ClPh |
| 1097 | CH$_2$(2-MePr$^c$) | Me | CHO | S | 2-ClPh |
| 1098 | CH$_2$CH=CH$_2$ | Me | CHO | S | 4-ClPh |
| 1099 | CH$_2$Pr$^c$ | Me | CHO | S | 4-ClPh |
| 1100 | CH$_2$(2-MePr$^c$) | Me | CHO | S | 4-ClPh |
| 1101 | CH$_2$(2-MePr$^c$) | Me | CHO | NH | 4-ClPh |
| 1102 | CH$_2$CH=CH$_2$ | Me | CHO | S | 2,4-diClPh |
| 1103 | CH$_2$Pr$^c$ | Me | CHO | S | 2,4-diClPh |
| 1104 | CH$_2$(2-MePr$^c$) | Me | CHO | S | 2,4-diClPh |

TABLE 1-continued

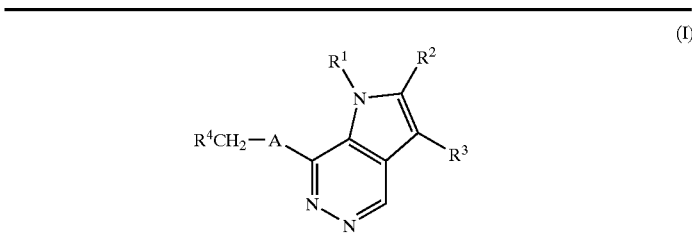

| Exemp. Comp. No. | R¹ | R² | R³ | A | R⁴ |
|---|---|---|---|---|---|
| 1105 | CH₂(2-MePr^c) | Me | CHO | NH | 2,4-diClPh |
| 1106 | CH₂(2-MePr^c) | Me | CO₂H | S | Ph |
| 1107 | CH₂CH=CH₂ | Me | CO₂H | S | 2-FPh |
| 1108 | CH₂(2-MePr^c) | Me | CO₂H | S | 2-FPh |
| 1109 | CH₂CH=CH₂ | Me | CO₂H | S | 4-FPh |
| 1110 | CH₂CH=CH₂ | Me | CO₂H | NH | 4-FPh |
| 1111 | CH₂CH=CHCH₃ | Me | CO₂H | S | 4-FPh |
| 1112 | CH₂Pr^c | Me | CO₂H | S | 4-FPh |
| 1113 | CH₂(2-MePr^c) | Me | CO₂H | S | 4-FPh |
| 1114 | CH₂(2-MePr^c) | Me | CO₂H | NH | 4-FPh |
| 1115 | CH₂CH=CH₂ | Me | CO₂H | S | 2,4-diFPh |
| 1116 | CH₂Pr^c | Me | CO₂H | S | 2,4-diFPh |
| 1117 | CH₂(2-MePr^c) | Me | CO₂H | S | 2,4-diFPh |
| 1118 | CH₂(2-MePr^c) | Me | CO₂H | NH | 2,4-diFPh |
| 1119 | CH₂CH=CH₂ | Me | CO₂H | S | 2-ClPh |
| 1120 | CH₂(2-MePr^c) | Me | CO₂H | S | 2-ClPh |
| 1121 | CH₂CH=CH₂ | Me | CO₂H | S | 4-ClPh |
| 1122 | CH₂Pr^c | Me | CO₂H | S | 4-ClPh |
| 1123 | CH₂(2-MePr^c) | Me | CO₂H | S | 4-ClPh |
| 1124 | CH₂(2-MePr^c) | Me | CO₂H | NH | 4-ClPh |
| 1125 | CH₂CH=CH₂ | Me | CO₂H | S | 2,4-diClPh |
| 1126 | CH₂Pr^c | Me | CO₂H | S | 2,4-diClPh |
| 1127 | CH₂(2-MePr^c) | Me | CO₂H | S | 2,4-diClPh |
| 1128 | CH₂(2-MePr^c) | Me | CO₂H | NH | 2,4-diClPh |
| 1129 | CH₂(2-MePr^c) | Me | CO₂Me | S | Ph |
| 1130 | CH₂(2-MePr^c) | Me | CO₂Me | S | 2-FPh |
| 1131 | CH₂CH=CH₂ | Me | CO₂Me | S | 4-FPh |
| 1132 | CH₂Pr^c | Me | CO₂Me | S | 4-FPh |
| 1133 | CH₂(2-MePr^c) | Me | CO₂Me | S | 4-FPh |
| 1134 | CH₂(2-MePr^c) | Me | CO₂Me | NH | 4-FPh |
| 1135 | CH₂CH=CH₂ | Me | CO₂Me | S | 2,4-diFPh |
| 1136 | CH₂(2-MePr^c) | Me | CO₂Me | S | 2,4-diFPh |
| 1137 | CH₂(2-MePr^c) | Me | CO₂Me | NH | 2,4-diFPh |
| 1138 | CH₂(2-MePr^c) | Me | CO₂Me | S | 2-ClPh |
| 1139 | CH₂CH=CH₂ | Me | CO₂Me | S | 4-ClPh |
| 1140 | CH₂(2-MePr^c) | Me | CO₂Me | S | 4-ClPh |
| 1141 | CH₂CH=CH₂ | Me | CO₂Me | S | 2,4-diClPh |
| 1142 | CH₂(2-MePr^c) | Me | CO₂Me | S | 2,4-diClPh |
| 1143 | CH₂(2-MePr^c) | Me | CO₂Me | NH | 2,4-diClPh |
| 1144 | CH₂(2-MePr^c) | Me | CO₂Et | S | Ph |
| 1145 | CH₂(2-MePr^c) | Me | CO₂Et | S | 2-FPh |
| 1146 | CH₂CH=CH₂ | Me | CO₂Et | S | 4-FPh |
| 1147 | CH₂Pr^c | Me | CO₂Et | S | 4-FPh |
| 1148 | CH₂(2-MePr^c) | Me | CO₂Et | S | 4-FPh |
| 1149 | CH₂(2-MePr^c) | Me | CO₂Et | NH | 4-FPh |
| 1150 | CH₂CH=CH₂ | Me | CO₂Et | S | 2,4-diFPh |
| 1151 | CH₂(2-MePr^c) | Me | CO₂Et | S | 2,4-diFPh |
| 1152 | CH₂(2-MePr^c) | Me | CO₂Et | NH | 2,4-diFPh |
| 1153 | CH₂(2-MePr^c) | Me | CO₂Et | S | 2-ClPh |
| 1154 | CH₂CH=CH₂ | Me | CO₂Et | S | 4-ClPh |
| 1155 | CH₂(2-MePr^c) | Me | CO₂Et | S | 4-ClPh |
| 1156 | CH₂CH=CH₂ | Me | CO₂Et | S | 2,4-diClPh |
| 1157 | CH₂(2-MePr^c) | Me | CO₂Et | S | 2,4-diClPh |
| 1158 | CH₂(2-MePr^c) | Me | CO₂Et | NH | 2,4-diClPh |
| 1159 | CH₂(2-MePr^c) | Me | CO₂Pr | S | 4-FPh |
| 1160 | CH₂(2-MePr^c) | Me | CO₂Bu | S | 4-FPh |
| 1161 | CH₂(2-MePr^c) | Me | CO₂Ph | S | 4-FPh |
| 1162 | CH₂CH=CH₂ | Me | CH₂OH | O | 2,6-diFPh |
| 1163 | CH₂CH=CHCH₃ | Me | CH₂OH | O | 2,6-diFPh |
| 1164 | CH₂Pr^c | Me | CH₂OH | O | 2,6-diFPh |
| 1165 | CH₂(2-MePr^c) | Me | CH₂OH | O | 2,6-diFPh |
| 1166 | CH₂CH=CH₂ | Me | CH₂OH | O | 2,6-diClPh |
| 1167 | CH₂CH=CHCH₃ | Me | CH₂OH | O | 2,6-diClPh |

TABLE 1-continued

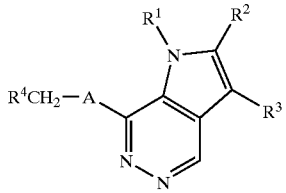

(I)

| Exemp. Comp. No. | R¹ | R² | R³ | A | R⁴ |
|---|---|---|---|---|---|
| 1168 | CH₂Pr^c | Me | CH₂OH | O | 2,6-diClPh |
| 1169 | CH₂(2-MePr^c) | Me | CH₂OH | O | 2,6-diClPh |
| 1170 | CH₂CH=CH₂ | Me | CH₂OAc | O | 2,6-diFPh |
| 1171 | CH₂CH=CHCH₃ | Me | CH₂OAc | O | 2,6-diFPh |
| 1172 | CH₂Pr^c | Me | CH₂OAc | O | 2,6-diFPh |
| 1173 | CH₂(2-MePr^c) | Me | CH₂OAc | O | 2,6-diFPh |
| 1174 | CH₂CH=CH₂ | Me | CH₂OAc | O | 2,6-diFPh |
| 1175 | CH₂CH=CHCH₃ | Me | CH₂OAc | O | 2,6-diClPh |
| 1176 | CH₂Pr^c | Me | CH₂OAc | O | 2,6-diClPh |
| 1177 | CH₂(2-MePr^c) | Me | CH₂OAc | O | 2,6-diClPh |
| 1178 | CH₂CH=CH₂ | Me | CHO | O | 2,6-diFPh |
| 1179 | CH₂CH=CHCH₃ | Me | CHO | O | 2,6-diFPh |
| 1180 | CH₂Pr^c | Me | CHO | O | 2,6-diFPh |
| 1181 | CH₂(2-MePr^c) | Me | CHO | O | 2,6-diFPh |
| 1182 | CH₂CH=CH₂ | Me | CHO | O | 2,6-diClPh |
| 1183 | CH₂CH=CHCH₃ | Me | CHO | O | 2,6-diClPh |
| 1184 | CH₂Pr^c | Me | CHO | O | 2,6-diClPh |
| 1185 | CH₂(2-MePr^c) | Me | CHO | O | 2,6-diClPh |
| 1186 | CH₂CH=CH₂ | Me | CO₂H | O | 2,6-diFPh |
| 1187 | CH₂CH=CHCH₃ | Me | CO₂H | O | 2,6-diFPh |
| 1188 | CH₂Pr^c | Me | CO₂H | O | 2,6-diFPh |
| 1189 | CH₂(2-MePr^c) | Me | CO₂H | O | 2,6-diFPh |
| 1190 | CH₂CH=CH₂ | Me | CO₂H | O | 2,6-diClPh |
| 1191 | CH₂CH=CHCH₃ | Me | CO₂H | O | 2,6-diClPh |
| 1192 | CH₂Pr^c | Me | CO₂H | O | 2,6-diClPh |
| 1193 | CH₂(2-MePr^c) | Me | CO₂H | O | 2,6-diClPh |
| 1194 | CH₂CH=CH₂ | Et | CH₂OH | O | 2,6-diFPh |
| 1195 | CH₂CH=CHCH₃ | Et | CH₂OH | O | 2,6-diFPh |
| 1196 | CH₂Pr^c | Et | CH₂OH | O | 2,6-diFPh |
| 1197 | CH₂(2-MePr^c) | Et | CH₂OH | O | 2,6-diFPh |
| 1198 | CH₂CH=CH₂ | Et | CH₂OH | O | 2,6-diClPh |
| 1199 | CH₂CH=CHCH₃ | Et | CH₂OH | O | 2,6-diClPh |
| 1200 | CH₂Pr^c | Et | CH₂OH | O | 2,6-diClPh |
| 1201 | CH₂(2-MePr^c) | Et | CH₂OH | O | 2,6-diClPh |
| 1202 | CH₂(2-MePr^c) | Me | CH₂OH | S | 2,6-diFPh |
| 1203 | CH₂(2-MePr^c) | Me | CH₂OH | NH | 2,6-diFPh |
| 1204 | CH₂(2-MePr^c) | Me | CH₂OH | S | 2,6-diClPh |
| 1205 | CH₂(2-MePr^c) | Me | CH₂OH | NH | 2,6-diClPh |

Throughout the table 1 the following abbreviations are used with the following meanings.

Exemp. Comp. No.: Exemplification compound number, Ac: acetyl, Bu: butyl, BU^c: cyclobutyl, Bur: butyryl, Et: ethyl, Hx^c: cyclohexyl, Me: methyl, Pn^c: cyclopentyl Ph: phenyl, Pr: propyl, Prp : propionyl, Pr^c: cyclopropyl.

In Table 1, preferred compounds are the compounds of Exemplification Compound numbers 2,4, 8, 9, 17, 19, 20, 21, 22, 24, 25, 26, 27, 28, 29, 30, 31, 32, 33, 34, 35, 36, 37, 38, 39, 40, 41, 42, 43, 44, 45, 46, 47, 48, 49, 50, 51, 56, 59, 61, 62, 63, 64, 65, 66, 67, 68, 69, 70, 71, 72, 73, 82, 90, 93, 95, 105, 106, 114, 116, 120, 121, 129, 132, 134, 138, 140, 142, 144, 146, 167, 178, 188, 192, 196, 200, 216, 225, 233, 237, 241, 245, 264, 277, 286, 290, 294, 298, 306, 307, 310, 311, 317, 323, 326, 329, 332, 345, 351, 357, 360, 363, 366, 373, 377, 381, 383, 385, 387, 394, 411, 414, 415, 416, 417, 418, 419, 420,421, 422, 423, 424, 425, 426, 427, 430, 433, 436, 439, 442, 449, 450, 451, 452, 453, 454, 455, 456, 457, 458, 461, 467, 470, 473, 476, 478, 480, 481, 482, 483, 484, 485, 486, 487, 488, 492, 494, 496, 498, 503, 504, 505, 506, 507, 508, 512, 514, 516, 518, 539, 542, 548, 558, 562, 564, 566, 583, 585, 589, 592, 594, 595, 596, 597, 598, 600, 602, 604, 606, 607, 608, 625, 626, 627, 633, 634, 665, 666, 667, 668, 669, 670, 671, 672, 675, 676, 681, 682, 683, 684, 685, 686, 702, 703, 704, 705, 706, 707, 723, 724, 725, 726, 727, 728, 834, 846, 858, 862, 889, 901, 930, 939, 990, 1014, 1018, 1072, 1090, 1094, 1113, 1117, 1133, 1136, 1148, 1149, 1159, 1163, 1164, 1165, 1167, 1169, 1171, 1173, 1175, 1177, 1181, 1185, 1189 and 1193.

More preferred compounds are the compounds of Exemplification Compound numbers 9, 19, 20, 22, 25, 32, 33, 40, 41, 43, 47, 48, 59, 61, 62, 63, 64, 65, 66, 67, 68, 69, 70, 71, 72, 73, 82, 93, 95, 105, 106, 114, 116, 120, 121, 134, 138, 142, 146, 167, 178, 311, 317, 416, 417, 420, 421, 427, 436, 439, 442, 450, 451, 454, 455, 461, 485, 506, 508, 589, 592, 594, 595, 596, 602, 606, 625, 633, 665, 666, 681, 682, 834, 846, 889, 1090, 1113, 1133, 1163, 1164, 1165, 1167, 1169, 1171, 1173, 1175 and 1177.

Further more preferred compounds are the compounds of Exemplification Compound numbers 9, 20, 22, 32, 33, 41, 43, 47, 48, 61, 63, 65, 69, 71, 73, 95, 106, 121, 421, 427, 455, 589, 594, 602, 606, 625, 1165 and 1169.

Still more preferred compounds are the compounds of Exemplification Compound numbers 22, 33, 43, 48, 106, 121, 421, 455 and 594.

Most preferred compounds are the compounds of:

Exemplification compound number 22: 1-(2-butenyl)-7-(4-fluorobenzyloxy)-3-hydroxymethyl-2-methylpyrrolo[2,3-d]pyridazine, Exemplification compound number 33: 7-(4fluorobenzyloxy)-3-hydroxymethyl-2-methyl-1-(2-methylcyclopropylmethyl)pyrrolo[2,3-d]pyridazine, Exemplification compound number 43: 1-(2-butenyl)-7-(2,4difluorobenzyloxy)-3-hydroxymethyl-2-methylpyrrolo[2,3-d]pyridazine, Exemplification compound number 48: 7-(2,4-difluorobenzyloxy)-3-hydroxymethyl-2-methyl-1-(2-methylcyclopropylmethyl)pyrrolo[2,3-d]py-ridazine, Exemplification compound number 106: 3-acetoxymethyl-7-4fluorobenzyloxy)-2-methyl-1-(2-methylcyclopropylmethyl)pyrrolo[2,3-d]pyridazine, and Exemplification compound number 121: 3-acetoxymethyl-7-(2,4difluorobenzyloxy)-2-methyl-1-(2-methylcyclopropylmethyl)pyrrolo[2,3-d]pyridazine.

In addition, of the compounds described above, 1-[(1S,2S)-2-methylcyclopropylmethyl] derivatives are preferred compounds.

The pyrrolopyridazine compounds of formula (I) can be prepared according to the following method.

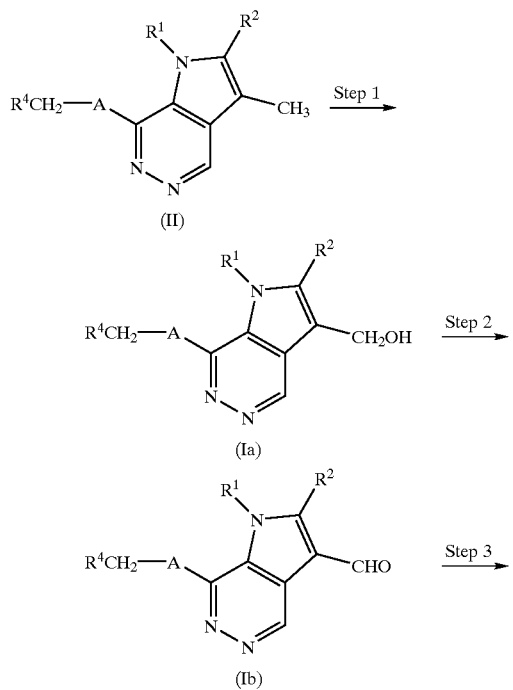

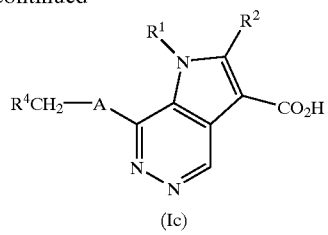

In the above reaction scheme $R^1$, $R^2$, $R^4$ and A have the same meanings as described above.

The step 1 is a process preparing a compound of formula (Ia) and is accomplished by reaction of a compound of formula (II) with an oxidizing agent in an inert solvent.

The oxidizing agent employed is, for example, an oxidizing agent by which a methyl group can be converted into a hydroxymethyl group, such as ammonium cerium (IV) nitrate, manganese (III) acetate or selenium dioxide; preferably ammonium cerium (IV) nitrate. The amount of the oxidizing agent is from 1.5 to 10 (preferably 2 to 6) moles to one mole of the compound of formula (II).

The employed inert solvent is not particularly limited provided that it has no adverse effect on the reaction and can dissolve the starting materials to a certain extent. Such a solvent is, for example, a halogeno-hydrocarbon such as methylene chloride, chloroform, carbon tetrachloride, dichloroethane, chlorobenzene, or dichlorobenzene; an ether such as diethyl ether, diisopropyl ether, tetrahydrofuran, dioxane, dimethoxyethane, or diethylene glycol dimethyl ether; a carboxylic acid or a carboxylic acid anhydride such as acetic acid, acetic anhydride, propionic acid, or benzoic acid; water; or mixtures thereof; and is preferably a carboxylic acid, a carboxylic acid anhydride, a carboxylic acid containing water or a mixture of a carboxylic acid and a carboxylic acid anhydride; and is more preferably acetic acid, acetic anhydride, acetic acid containing water or a mixture of acetic acid and acetic anhydride.

The reaction temperature is usually from 0° C. to 150° C. (preferably from room temperature to 100° C.). The reaction time varies depending on the reaction temperature and other factors but it is from 30 minutes to 20 hours (preferably from 1 hour to 10 hours).

When a carboxylic acid or a carboxylic acid anhydride is used as the inert solvent in the step 1, in certain cases a product esterified at the hydroxymethyl group of compound (Ia) by the carboxylic acid can be obtained. The esterified compound is hydrolyzed according to a conventional method to give the compound of formula (Ia). For example the esterified compound is treated with a base (for example an alkali metal hydroxide such as lithium hydroxide, sodium hydroxide, or potassium hydroxide; or an alkali metal carbonate such as sodium carbonate, potassium carbonate; preferably an alkali metal hydroxide and most preferably lithium hydroxide) at from 0° C. to 100° C. (preferably from 10° C. to 50° C.) for from 10 minutes to 10 hours (preferably from 20 minutes to 5 hours) in an inert solvent containing water (for example, an alcohol containing water such as methanol containing water or ethanol containing water) to give a compound of formula (Ia).

A compound of formula (Id), which is a compound of formula (I) wherein $R^3$ is a $C_2$–$C_6$ aliphatic acyloxymethyl group, a $C_6$–$C_{10}$arylcarbonyloxymethyl group which may be optionally substituted with substituents selected from the group consisting of $C_1$–$C_6$ alkyl, $C_1$–$C_6$ alkoxy and halogeno, or a $C_1$–$C_6$ alkoxycarbonyloxymethyl group, can be prepared by acylation of a compound of formula (Ia).

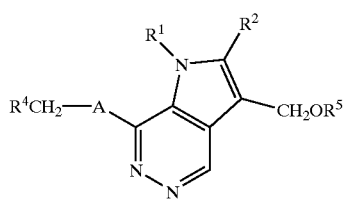

(Id)

In the formula of (Id), $R^5$ represents a $C_2$–$C_6$ aliphatic acyl group, a $C_6$–$C_{10}$ arylcarbonyl group which may be optionally substituted with substituents selected from the group consisting of $C_1$–$C_6$ alkyl, $C_1$–$C_6$ alkoxy and halogeno, or a $C_1$–$C_6$ alkoxycarbonyl group, and $R^1$, $R^2$, $R^4$ and A have the same meanings as described above.

The acylating reagent is, for example, a $C_2$–$C_6$ aliphatic acyl halide such as acetyl chloride, acetyl bromide, propionyl chloride, propionyl bromide, butyryl chloride, isobutyryl chloride, valeryl chloride, or hexanoyl chloride; a $C_2$–$C_6$ aliphatic carboxylic acid anhydride such as acetic anhydride, propionic anhydride, or hexanoic anhydride; a $C_6$–$C_{10}$ arylcarbonyl halide which may be optionally substituted with substituents selected from the group consisting of $C_1$–$C_6$ alkyl, $C_1$–$C_6$ alkoxy and halogeno, such as benzoyl chloride, benzoyl bromide, toluoyl chloride, toluoyl bromide, methoxybenzoyl chloride, chlorobenzoyl chloride, fluorobenzoyl chloride, or naphthoyl chloride; or a $C_1$–$C_6$ alkoxycarbonyl halide such as methoxycarbonyl chloride, ethoxycarbonyl chloride, ethoxycarbonyl bromide, propoxycarbonyl chloride, butoxycarbonyl chloride, pentyloxycarbonyl chloride, or hexyloxycarbonyl chloride; preferably a $C_2$–$C_6$ aliphatic acyl chloride, a $C_6$–$C_{10}$ arylcarbonyl chloride which may be optionally substituted with substituents selected from the group consisting of $C_1$–$C_6$ alkyl $C_1$–$C_6$ alkoxy and halogeno or a $C_1$–$C_6$ alkoxycarbonyl chloride.

The employed base is, for example, an alkali metal amide such as lithium amide, sodium amide, or potassium amide; an alkali metal carbonate such as lithium carbonate, sodium carbonate, or potassium carbonate; an alkali metal alkoxide such as lithium methoxide, sodium methoxide, sodium ethoxide, or potassium t-butoxide; or an organic amine such as triethylamine, tributylamine, diisopropylethylamine, N-ethylmorpholine, pyridine, picoline, 4-(N,N-dimethylamino)pyridine, quinoline, N,N-dimethylaniline, N,N-diethylaniline, 1,5-diazabicyclo[4.3.0]non-5-ene (DBN), 1,4-diazabicyclo[2.2.2]octane (DABCO), or 1,8-diazabicyclo[5.4.0]undec-7-ene (DBU); preferably an organic amine and most preferably triethylamine or pyridine.

The employed inert solvent is not particularly limited provided that it has no adverse effect on the reaction and can dissolve the starting materials to a certain extent. Such a solvent is, for example, an aromatic hydrocarbon such as benzene, toluene, or xylene; a halogeno-hydrocarbon such as methylene chloride, chloroform, carbon tetrachloride, dichloroethane, chlorobenzene, or dichlorobenzene; an ether such as diethyl ether, diisopropyl ether, tetrahydrofuran, dioxane, dimethoxyethane, or diethylene glycol dimethyl ether-, or mixtures thereof; and is preferably a halogeno-hydrocarbon or an ether; and is more preferably methylene chloride, chloroform, diethyl ether or tetrahydrofuran.

The reaction temperature is usually from 0° C. to 100° C. (preferably from 10° C. to 50° C.). The reaction time varies depending on the reaction temperature and other factors but it is from 10 minutes to 100 hours (preferably from 30 minutes to 5 hours).

The step 2 is a process for preparing a compound of formula (Ib) and is accomplished by reaction of a compound of formula (Ia) with an oxidizing agent in an inert solvent.

The employed oxidizing agent is, for example, an oxidizing agent by which a hydroxymethyl group can be converted into a formyl group, such as manganese dioxide, pyridinium chlorochromate (PCC), pyridinium dichromate (PDC), or a mixture of dimethyl sulfoxide and an acid anhydride (for example an aliphatic carboxylic acid anhydride which may be optionally substituted with halogeno, such as acetic anhydride, trifluoroacetic anhydride, or propionic anhydride; preferably acetic anhydride or trifluoroacetic anhydride); preferably manganese dioxide. The amount of the oxidizing agent is usually from 1 to 50 (preferably 2 to 30) moles to one mole of the compound of formula (Ia).

The employed inert solvent is not particularly limited provided that it has no adverse effect on the reaction and can dissolve the starting materials to a certain extent. Such a solvent is, for example, an aromatic hydrocarbon such as benzene, toluene, or xylene; a halogeno-hydrocarbon such as methylene chloride, chloroform, carbon tetrachloride, dichloroethane, chlorobenzene, or dichlorobenzene; an ether such as diethyl ether, diisopropyl ether, tetrahydrofuran, dioxane, dimethoxyethane, or diethylene glycol dimethyl ether; or mixtures thereof; and is preferably a halogeno-hydrocarbon; and is most preferably methylene chloride.

The reaction temperature is usually from 0° C. to 150° C. (preferably from room temperature to 100° C.). The reaction time varies depending on the reaction temperature and other factors but it is from 30 minutes to 40 hours (preferably from 1 hour to 20 hours).

The step 3 is a process preparing a compound of formula (Ic) and is accomplished by reaction of a compound of formula (Ib) with an oxidizing agent in an inert solvent.

The employed oxidizing agent is, for example, an oxidizing agent by which a formyl group can be converted into a carboxyl group, such as silver oxide, pyridinium chlorochromate (PCC), or pyridinium dichromate (PDC); preferably silver oxide. The amount of the oxidizing agent is usually from 1 to 20 (preferably 2 to 10) moles to one mole of the compound of formula (Ib). When silver oxide is used as an oxidizing agent, silver oxide prepared by reaction of silver nitrate with an alkali metal hydroxide (preferably sodium hydroxide) is preferably used.

The employed inert solvent is not particularly limited provided that it has no adverse effect on the reaction and can dissolve the starting materials to a certain extent. Such a solvent is, for example, a halogeno-hydrocarbon such as methylene chloride, chloroform, carbon tetrachloride, dichloroethane, chlorobenzene, or dichlorobenzene; an ether such as diethyl ether, diisopropyl ether, tetrahydrofuran, dioxane, dimethoxyethane, or diethylene glycol dimethyl ether; an alcohol such as methanol, or ethanol; a carboxylic acid such as acetic acid, propionic acid, or benzoic acid; water; or mixtures thereof; and is preferably an alcohol, an alchohol containing water, a carboxylic acid, a carboxylic acid containing water or water; and is more preferably an alcohol containing water; and is most preferably ethanol containing water.

The reaction temperature is usually from 0° C. to 150° C. (preferably from room temperature to 100° C.). The reaction time varies depending on the reaction temperature and other factors but it is from 1 hour to 72 hours (preferably from 12 hours to 48 hours).

A compound of formula (Ie), which is a compound of formula (I) wherein $R^3$ is a $C_1$–$C_6$ alkoxycarbonyl group or a $C_6$–$C_{10}$ aryloxycarbonyl group which may be optionally substituted with substituents selected from the group consisting of $C_1$-$C_6$ alkyl, $C_1$-$C_6$ alkoxy and halogeno, can be prepared by esterification of a compound of formula (Ic).

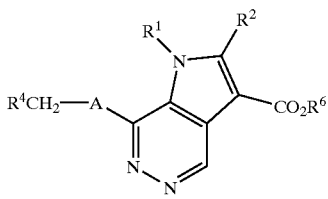

(Ie)

In the formula (Ie), $R^6$ represents a $C_1$-$C_6$ alkyl group, or a $C_6$-$C_{10}$ aryl group which may be optionally substituted with substituents selected from the group consisting of $C_1$-$C_6$ alkyl, $C_1$-$C_6$ alkoxy and halogeno and $R^1$, $R^2$, $R^4$ and A have the same meanings as described above.

The esterification is accomplished by reaction of a compound of formula (Ic) with a halogenating agent in an inert solvent to afford a carboxylic acid halide, followed by reaction of the carboxylic acid halide with an alcohol or a phenol derivative in the presence of a base in an inert solvent. The two step reactions can be carried out in a single reaction vessel, wherein the compound of formula (Ic) is reacted with a halogenating agent and, if necessary, the solvent can be removed from the reaction mixture.

The halogenating agent employed is, for example, a thionyl halide such as thionyl chloride, thionyl bromide or a phosphorus halide such as phosphorus trichloride, phosphorus pentachloride, phosphorus oxychloride, or phosphorus oxybromide; preferably thionyl chloride or phosphorus oxychloride.

The inert solvent employed in the reaction of the compound of formula (Ic) with a halogenating agent is not particularly limited provided that it has no adverse effect on the reaction and can dissolve the starting materials to a certain extent. Such a solvent is, for example, an aromatic hydrocarbon such as benzene, toluene, or xylene; a halogeno-hydrocarbon such as methylene chloride, chloroform, carbon tetrachloride, dichloroethane, chlorobenzene, or dichlorobenzene; an ether such as diethyl ether, diisopropyl ether, tetrahydrofuran, dioxane, dimethoxyethane, or diethylene glycol dimethyl ether; or mixtures thereof; and is preferably an ether; and is most preferably diethyl ether or tetrahydrofuran.

The reaction temperature is usually from 0° C. to 100° C. (preferably 10° C. to 50° C.). The reaction time varies depending on the reaction temperature and other factors but it is from 10 minutes to 10 hours (preferably from 30 minutes to 5 hours).

The inert solvent employed in the reaction of the carboxylic acid halide with an alcohol or phenol derivative is the same solvent as described in the reaction of the compound of formula (Ic) with a halogenating agent. The reaction temperature and the time required for the reaction are in the same range as described in the reaction of the compound of formula (Ic) with a halogenating agent.

In each step described above each desired compound may be isolated by conventional procedures from the reaction mixture. For example, it may be obtained 1) by filtration of the reaction mixture when insoluble material exists in the reaction mixture, followed by evaporation of the solvent of the filtrate; or by 1) concentration of the reaction mixture, 2) addition of water to the residue followed by partition between water and an appropriate organic solvent immiscible with water, 3) drying the extract over anhydrous magnesium sulfate and the like, followed by 4) concentration of the extract. The desired compound can be, if necessary, be further purified by conventional procedures such as recrystallization, column chromatography and the like.

A compound of formula (I) can be transformed into a pharmaceutically acceptable salt thereof by treatment of the compound of formula (I) with an acid according to a conventional technique. For example the desired salt can be obtained by reaction of a compound of formula (I) with an acid in an inert solvent (preferably an ether such as diethyl ether, tetrahydrofuran, or dioxane; an alcohol such as methanol, ethanol, or propanol; or a halogeno-hydrocarbon such as methylene chloride, or chloroform) at room temperature for from 5 minutes to 1 hour, followed by evaporation of the solvent.

The starting compound of formula (II) is known or can easily be prepared by the reaction of a pyrrole compound of formula (III) with a compound of formula $R^1$-X (IV) according to a known method (for example Japanese Patent Application Publication Hei 7-247285);

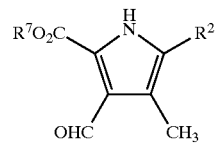

(III)

wherein $R^7$ represents a $C_1$-$C_6$ alkyl group, $R^2$ has the same meanings as described above, X represents a halogen atom (preferably a chlorine or bromine atom), and $R^1$ has the same meanings as described above.

The compounds of formula (III) and (IV) are also known or can easily be obtained by a known procedure (for example Japanese Patent Application Publication Hei 7-247825; Monatschefte fur Chemie (1973), 104, 925; J. Chem. Soc., Perkin.Trans.II (1979) 287 and the like).

In addition each desired optically active compound of formula (I) and (IV) (for example 1S,2S-form) can be obtained by optical resolution of a racemic form of the corresponding compound (a mixture of 1S,2S-form and 1R,2R-form and the like). The optical resolution can be carried out by an appropriate selection from conventional techniques such as chromatography on a column for optical resolution, preferential crystallization, and resolution of a mixture of diastereomeric salts.

The compounds of formula (I) or pharmaceutically acceptable salts thereof of this invention exhibit potent gastric acid secretion inhibition activity, gastric mucous membrane protection activity and potent antibacterial activity against *Helicobacter pylori* and they have excellent properties as a medicament. The compounds of formula (I) or pharmaceutically acceptable salts thereof are useful as a prophylactic or therapeutic medicament for the prevention and treatment of ulcerative diseases such as peptic ulcer, acute or chronic gastric ulcer, gastrisis, reflux esophagitis, gastroesophageal reflux disorder, dyspepsia, gastric hyperacidity, Zollinger-Ellison syndrome etc. and for bacterial infections arising from *Helicobacter pylori*.

When used as a prophylactic or therapeutic medicament for the diseases described above, a compound of formula (I) or a pharmaceutically acceptable salt thereof (the active ingredient) can be administered alone or can be presented as part of a pharmaceutical formulation. The pharmaceutical formulation is prepared by blending the active ingredient with appropriate pharmaceutically acceptable carriers, e.g., excipients, diluents and the like, followed by formulation in the form of tablets, capsules, granules, powders or syrups and the like for oral administration or in the form of injections and the like for parenteral administration (preferably oral administration).

The production of such pharmaceutical formulations is carried out according to general techniques known to those skilled in the art using carriers which may includes such additives as an excipient, a binder, a disintegrant, a lubricant, a stabilizer, a corrigent, a diluent and a solvent for injections.

The excipient is, for example, a sugar derivative such as lactose, sucrose, glucose, mannitol, or sorbitol; a starch derivative such as corn starch, potato starch, α-starch, dextrin, or carboxymethyl starch; a cellulose derivative such as crystalline cellulose, low-substituted hydroxypropyl cellulose, hydroxypropylmethyl cellulose, carboxymethyl cellulose, calcium carboxymethyl cellulose, or internally bridged sodium carboxymethyl cellulose; acacia; dextran; pullulan; a silicate derivative such as light silicic acid anhydride, synthetic aluminium silicate, or magnesium aluminate meta-silicate; a phosphonate derivative such as calcium phosphonate; a carbonate derivative such as calcium carbonate; a sulfate derivative such as calcium sulfate; and the like.

The binder is, for example, one of the excipients described above; gelatin; polyvinylpyrrolidone; macrogol (trade mark) and the like.

The disintegrant is, for example, one of the excipients described above; a chemically modified starch or cellulose derivative such as sodium croscarmellose or sodium carboxymethyl starch; bridged polyvinylpyrrolidone; and the like.

The lubricant is, for example, talc; stearic acid; a metal salt of stearic acid such as calcium stearate, or magnesium stearate; colloidal silica; a wax such as bee gum and spermaceti; boric acid; glycol; a carboxylic acid such as fumaric acid, or adipic acid; a sodium carboxylate such as sodium benzoate; a sulfate such as sodium sulfate; leucine; a laurylsulfate such as sodium laurylsulfate, or magnesium laurylsulfate; a silicic acid such as silicic acid anhydride, or a silicic acid hydrate; one of the starch derivatives described above in relation to the excipients; and the like.

The stabilizer is, for example, a p-hydroxybenzoate derivative such as methylparaben, or propylparaben; an alcohol such as chlorobutanol, benzyl alcohol, or phenylethyl alcohol; benzalkonium chloride; a phenol derivative such as phenol, or cresol; thimerosal; dehydroacetic acid; sorbic acid; and the like.

The corrigent is, for example, a sweetening, souring, or flavoring agent, which are conventionally used; and the like.

The solvent for injection is, for example, water, ethanol, glycerin and the like.

Suitable dosage levels will depend on the condition of the patient, human or other animal, the disease, whether the drug administration is for prevention or treatment, the age of the patient and the like, but typically suitable dosage levels for an active ingredient of the present invention are from 1 mg (preferably 5 mg) to 1000 mg (preferably 500 mg) for oral administration and from 0.1 mg (preferably 1 mg) to 500 mg (preferably 300 mg) for intravenous administration per unit dose, per day, for an adult human, respectively. The dosages described above are preferably administered from one time to six times throughout the day, depending on the condition of the disease.

The following Examples, Reference Examples, Test Examples and Formulation Examples are intended to further illustrate the present invention and are not intended to limit the scope of the invention.

EXAMPLE 1

3-Acetoxymethyl-7-(4-fluorobenzyloxy)-2-methyl-1-[(1S,2S)-2-methylcyclopropylmethyl]pyrrolo[2,3-d]-pyridazine To a solution of 7-(4-fluorobenzyloxy)-2,3-dimethyl-1-[(1S,2S)-2-methylcyclopropylmethyl]pyrrolo[2,3-d] pyridazine (0.679 g, 2.00 mmol) in acetic acid (40 ml) was added ammonium cerium (IV) nitrate (6.58 g, 12.0 mmol) at room temperature. The mixture was stirred at 60° C. for 3 hours, poured into water and extracted with ethyl acetate. The extract was washed with a saturated aqueous sodium chloride solution, dried over anhydrous magnesium sulfate and concentrated in vacuo. The residue was chromatographed on a silica gel column using hexane/ethyl acetate= 1/1 as the eluant to afford an oil which was crystallized in hexane to give the title compound (0.255 g, 28%) as pale yellow crystals.

Melting point: 122–123° C. Mass spectrum (CI, m/z): 398 ($M^+$+1). NMR spectrum $CDCl_3$, δppm): 0.13-0.20 (m, 1H), 0.37–0.44 (m, 1H), 0.61–0.68 (m, 1H), 0.84–0.91 (m, 1H), 0.90 (d; J=5.9 Hz, 3H), 2.05 (s, 3H), 2.48 (s, 3H), 4.14 (dd; J=14.6 Hz, 7.3 Hz, 1H), 4.31 (dd; J=14.6 Hz, 6.3 Hz, 1H), 5.27 (s, 2H), 5.65 J=12.0 Hz, 1H), 5.70 (d; J=12.0 Hz, 1H), 7.05–7.12 (m, 2H), 7.48–7.53 (m,2H), 9.12 (s, 1H).

EXAMPLE 2

7-(4-Fluorobenzyloxy)-3-hydroxymethyl-2-methyl-1-[(1S,2S)-2-methylcyclopropylmethyl]pyrrolo[2,3-d]-pyridazine To a solution of 7-(4-fluorobenzyloxy)-2,3-dimethyl-1-[(1S,2S)-2-methylcyclopropylmethyl]pyrrolo[2,3d] pyridazine (67.9 g, 200 mmol) in acetic acid (800 ml) was added ammonium cerium (IV) nitrate (329 g, 600 mmol) at room temperature. The mixture was stirred at 55° C. for 8 hours, poured into water and extracted with ethyl acetate. The extract was washed with a saturated aqueous sodium chloride solution, dried over anhydrous magnesium sulfate and concentrated in vacuo. To the residue were added methanol (500 ml) and a 2N aqueous lithium hydroxide solution (160 ml) and the mixture was stirred at room temperature for 40 minutes. The reaction mixture was neutralized with 1N hydrochloric acid and the methanol was evaporated off in vacuo. The resulting mixture was extracted with chloroform. The extract was washed with a saturated aqueous sodium chloride solution, dried over anhydrous magnesium sulfate and concentrated in vacuo. The residue was chromatographed on a silica gel column using ethyl acetate and ethyl acetate/methanol=9/1 as the eluant to afford crystals which were washed with ethyl acetate to give the title compound (24.6 g, 35%) as pale yellow crystals.

Melting point: 128–129° C. Mass spectrum (CI, m/z): 356 ($M^+$+1). NMR spectrum $CDCl_3$, δppm): 0.10-0.16 (m, 1H), 0.340.40 (m, 1H), 0.58–0.68 (m, 1H), 0.77–0.86 (m, 1H), 0.87 (d; J=5.9 Hz,3H), 2.44 (s, 3H), 4.09 (dd; J=14.6 Hz, 7.3 Hz, 1H), 4.26 (dd; J=14.6 Hz, 6.3 Hz, 1H), 4.82 (s, 2H), 5.57 (d; J=11.7 Hz, 1H), 5.62 (d; J=11.7 Hz, 1H), 7.04–7.09 (m, 2H), 7.47 (dd; J=8.8 Hz, 5.4 Hz, 2H), 9.07 (s, 1H). Optical rotation: $[\alpha]_D^{20}$ =+18.2°(C=1.00, MeOH).

EXAMPLE 3

7-(4-Fluorobenzyloxy)-3-formyl-2-methyl-1-[(1S,2S)-2-methylcyclopropylmethyl]pyrrolo[2,3-d]pyridazine To a solution of 7-(4-fluorobenzyloxy)-3-hydroxymethyl-2-methyl-1-[(1S,2S)-2-methylcyclopropylmethyl]pyrrolo[2, 3-d]pyridazine (64.3 g, 181 mmol) in methylene chloride (900 ml) was added activated manganese dioxide (472 g, 5.43 mol) at room temperature. The mixture was stirred at room temperature for 18 hours. The reaction mixture was filtered through celite (trade mark) and the filtrate was concentrated in vacuo. The crude crystals (45.7 g) were washed with ethyl acetate and hexane to give the title compound (44.3 g, 69%) as pale yellow crystals.

Melting point: 138.5–139.5° C. Mass spectrum (CI, m/z): 354 (M$^+$+1). NMR spectrum (CDCl$_3$, δppm): 0.19-0.26 (m, 1H), 0.40–0.47 (m, 1H), 0.71–0.78 (m, 1H), 0.84–0.91 (m, 1H), 0.92 (d; J=5.9 Hz, 3H), 2.75 (s, 3H), 4.19 (dd; J=14.6 Hz, 7.1 Hz, 1H), 4.35 (dd; J=14.6 Hz, 6.6 Hz, 1H), 5.67 (d; J=12.0 Hz, 1H), 5.73 (d; J=12.0 Hz, 1H), 7.07–7.14 (m, 2H), 7.51 (dd; J=8.5 Hz, 5.4 Hz, 2H), 9.63 (s, 1H), 10.22 (s, 1H). Optical rotation: $[\alpha]_D^{20}$=+20.4° (C=1.00, MeOH).

EXAMPLE 4

3-Carboxy-7-(4-fluorobenzyloxy)-2-methyl-1-[(1S, 2S)-2-methylcyclopropylmethyl]pyrrolo[2,3-d] pyridazine To a solution of silver nitrate (0.85 g, 5 mmol) in water (2.5 ml) was added an aqueous 2N lithium hydroxide solution (3 ml), followed by a solution of 7-(4-fluorobenzyloxy)-3-formyl-2-methyl-1-[(1S,2S)-2-methylcyclopropylmethyl]pyrrolo[2,3-d]pyridazine (0.177 g, 0.5 mmol) in ethanol (10 ml). The mixture was stirred at room temperature for 48 hours. To the reaction mixture was added 1N hydrochloric acid (3 ml) and the resulting mixture was filtered through celite (trade mark). The celite (trade mark) was washed with ethanol (30 ml). To the combined filtrates was added water and the resulting mixture was extracted with chloroform. The extract was dried over anhydrous magnesium sulfate and concentrated in vacuo. The residue was chromatographed on a silica gel column using chloroform/isopropanol=19/1 as the eluant to give the title compound (0.094 g, 51%) as pale yellow crystals.

Melting point: 170–225° C. Mass spectrum (CI, m/z): 370 (M$^+$+1). NMR spectrum CDCl$_3$, δppm): 0.20-0.25 (m, 1H), 0.40–0.46 (m, 1H), 0.63–0.69 (m, 1H), 0.86–0.92 (m, 1H), 0.91 (d; J=5.9 Hz, 3H), 2.86 (s, 3H), 3.60 (bs, 1H), 4.26 (dd; J=14.7 Hz, 7.3 Hz, 1H), 4.40 (dd; J=14.7 Hz, 6.8 Hz, 1H), 5.67 (d; J=11.7 Hz, 1H), 5.72 (d; J=11.7 Hz, 1H), 7.08–7.14 (m, 2H), 7.53 (dd; J=8.8 Hz, 5.4 Hz, 2H), 9.88 (bs, 1H). Optical rotation: $[\alpha]_D^{20}$=+15.8° (C=1.00, MeOH), Reference Example 1

7-(4-Fluorobenzyloxy)-2,3-dimethyl-1-[(1S,2S)-2-methylcyclopropylmethyl]pyrrolo[2,3-]-pyridazine
(a) Methyl 3-formyl-4,5-dimethyl-1-[(1S,2S)-2-methylcyclopropylmethyl]pyrrole-2-carboxylate Potassium tert-butoxide (3.49 g, 35.1 mmol) was added to a solution of methyl 3-formyl-4,5-dimethylpyrrole-2-carboxylate (5.79 g, 31.9 mmol) and 18-crown-6 (0.41 g, 1.55 mmol) in tetrahydrofuran (130 ml) and the mixture was stirred at room temperature for 1 hour. After dropwise addition over 30 minutes of (1S,2S)-2-methylcyclopropylmethyl bromide (5.71 g, 38.3 mmol) to the reaction mixture at 50° C., the mixture was heated under reflux for 3 hours. Potassium tert-butoxide (0.36 g, 3.22 mmol) and (1S,2S)-2-methylcyclopropylmethyl bromide (0.48 g, 3.21 mmol) were further added to the mixture and this mixture was heated for 1 hour. The reaction mixture was poured into ice-water and extracted with ethyl acetate. The extract was washed with water and a saturated aqueous sodium chloride solution and then dried over anhydrous magnesium sulfate. The solvent was removed in vacuo to afford the desired compound (8.26 g, 100%) as a pale brown oil.

Mass spectrum (CI, m/z): 250 (M$^+$+1) NMR spectrum CDCl$_3$, δppm): 0.25 (dt; J=8 Hz, 5 Hz, 1H), 0.48 (dt; J=8 Hz, 5 Hz 1H), 0.71–0.80 (m, 1H), 0.82–0.89 (m, 1H), 1.00 (d; J=6 Hz, 3H), 2.20 (s, 3H), 3.89 (s, 3H), 4.25 (d; J=7 Hz, 2H), 10.43 (s, 1H). Optical rotation: $[\alpha]_D^{20}$=+17.6° (C=1.02, EtOH).

(b) 2,3-Dimethyl-1-[(1S,2S)-2-methylcyclopropylmethyl]-6,7-dihydropyrrolo[2,3-d]pyridazine-7-one Hydrazine hydrate (1.92 g, 38.4 mmol) was added to a solution of methyl 3-formyl-4,5-dimethyl-1-[(1S,2S)-2-methylcyclopropylmethyl]pyrrole-2-carboxylate (7.96 g 31.9 mmol) in acetic acid (38 ml) at room temperature and the mixture was stirred at 90° C. for 1 hour. After the reaction was completed, the reaction mixture was cooled to room temperature and poured into ice-water. The crude crystals were collected by filtration, washed with water and dissolved in a mixture of chloroform and methanol (9:1). The organic layer was separated, washed with a saturated aqueous sodium chloride solution and then dried over anhydrous magnesium sulfate. The solvent was removed in vacuo and to the residue was added a mixture of toluene and hexane. The precipitate was collected by filtration to afford the desired compound (7.02 g, 95.0%) as a pale yellowish white powder.

Mass spectrum (CI, m/z): 232 (M$^+$+1) NMR spectrum (CDCl$_3$, δppm): 0.22 (dt; J=8 Hz, 5 Hz, 1H), 0.64 (dt; J=8 Hz, 5 Hz, 1H), 0.86–0.95 (m, 2H), 0.98 (d; J=5 Hz, 3H), 2.21 (s, 3H), 2.35 (s, 3H), 4.44(d; J=7 Hz, 2Hl), 8.05 (s, 1H), 9.97 (s, 1H). Optical rotation: $[\alpha]_D^{20}$=+11.2° (C=0.50, EtOH).

(c) 7-Chloro-2,3-dimethyl-1-[(1S,2S)-2-methylcyclopropylmethyl]pyrrolo[2,3-d]pyridazine Phosphorus oxychloride (55 ml, 590 mmol) was added to 2,3-dimethyl-1-[(1S,2S)-2-methylcyclopropylmethyl]-6,7-dihydropyrrolo[2,3-d]pyridazine-7-one (6.95 g, 30.1 mmol) and the mixture was stirred at 90° C. for 3.5 hours. After the reaction was completed, the reaction mixture was cooled to room temperature and poured into ice-water. The aqueous solution was neutralized with a 5N aqueous sodium hydroxide solution and extracted with methylene chloride. The extract was washed with water, dried over anhydrous magnesium sulfate and then concentrated in vacuo. Hexane was added to the residue and the precipitate was collected by filtration to afford the desired compound (6.90 g, 92.0%) as a pale yellow powder.

Mass spectrum (CI, m/z): 250 (M$^+$+1) NMR spectrum CDCl$_3$, δppm): 0.29 (dt; J=8 Hz, 5 Hz, 1H), 0.54 (dt; J=8 Hz, 5 Hz, 1H), 0.73–1.02 (m, 5H), 2.30 (s, 3H), 2.43 (s, 3H), 4.44 (d; J=6 Hz, 2H), 9.15 (s,1H). Optical rotation: $[\alpha]_D^{20}$+ 12.3° (C=1.01, EtOH).

(d) 7-(4-Fluorobenzyloxy)-2,3-dimethyl-1-[(1S,2S)-2-methylcyclopropylmethyl]pyrrolo[2,3-d]-pyridazine A solution of p-fluorobenzyl alcohol (1.45 g, 11.5 mmol) in tetrahydrofuran (2 ml) was added dropwise to a solution of sodium hydride (0.26 g, 10.8 mmol) in tetrahydrofuran (6 ml) and the mixture was stirred at room temperature for 30 minutes. A solution of 7-chloro-2,3-dimethyl-1-[(1S,2S)-2-methylcyclopropylmethyl]pyrrolo[2,3-d]pyridazine (2.50 g, 10.0 mmol) in tetrahydrofuran (13 ml) was added dropwise to the reaction mixture at room temperature and the mixture was heated under reflux for 3 hours. After the reaction was completed, the reaction mixture was poured into ice-water and extracted with ethyl acetate. The extract was washed with a saturated aqueous sodium chloride solution, dried over anhydrous magnesium sulfate and then concentrated in vacuo. Hexane was added to the concentrated solution, and the precipitate was collected by filtration and then recrystallized from a mixture of ethyl acetate and hexane to afford the title compound (2.25 g, 66.4%) as pale brown crystals.

Mp: 114–115° C. Mass spectrum (CI, m/z): 340 (M$^+$+1) 1H-NMR spectrum (CDCl$_3$, δppm): 0.14 (dt; J=8 Hz, 5 Hz, 1H), 0.39 (dt; J=8 Hz, 5 Hz, 1H), 0.59–0.65 (m, 1H), 0.76–0.85 (m, 1H), 0.89 (d; J=6 Hz, 3H), 2.26 (s,3H), 2.36 (s, 3H), 4.13 (dd; J=15 Hz, 7 Hz, 1H), 4.27 (dd; J=15 Hz, 6 Hz, 1H), J=12 Hz, 1H), 5.68 (d; J=12 Hz, 1H), 7.05–7.12 (m, 2H), 7.47–7.52 (m, 2H), 8.96 (s, 1H). Optical rotation: $[\alpha]_D^{20}$=+17.9° (C=0.50, EtOH).

Reference Example 2

Methyl 3-formyl-4,5-dimethyl-1-[(1S,2S)-2-methylcyclopropylmethyl]pyrrole-2-carboxylate (a) Methyl-4,5-dimethyl-1-[(E)-2-methylcyclopropylmethyl]pyrrole-2-carboxylate Potassium tert-butoxide (18.33 g, 164 mmol) was added to a solution of methyl 4,5-dimethylpyrrole-2-carboxylate (25.02 g, 163 mmol) and 18-crown-6 (3.19 g, 12.1 mmol) in tetrahydrofuran (150 ml) and the mixture was stirred at room temperature for 1 hour. To this mixture was added a solution of (E)-2-methylcyclopropylmethyl bromide (racemate, 12.70 g, 85.2 mmol) and the mixture was heated under reflux for 7 hours. After the reaction was completed, the reaction mixture was poured into ice-water and extracted with ethyl acetate. The extract was washed with water and a saturated aqueous sodium chloride solution, dried over anhydrous magnesium sulfate and then concentrated in vacuo. The residue was chromatographed on a column using toluene as the eluant to afford the desired compound (racemate, 13.50 g, 71.6%) as a brown oil.

Mass spectrum (CI, m/z): 222 (M$^+$+1) NMR spectrum (CDCl$_3$, δppm): 0.20 (dt; J=8 Hz, 5 Hz, 1H), 0.48 (dt; J=8 Hz, 5 Hz, 1H), 0.67–0.93 (m, 2H), 0.98 (d; J=6 Hz, 3H), 2.01 (s, 3H), 2.18 (s, 3H), 3.76 (s,3H) 4.21 (d; J=7 Hz, 2H), 6.76 (s, 1H).

(b) Methyl 4,5-dimethyl-1-[(1S,2S)-2-methylcyclopropylmethyl]pyrrole-2-carboxylate Methyl 4,5-dimethyl-1-[(E)-2-methylcyclopropylmethyl] pyrrole-2-carboxylate (10.00 g) was chromatographed by high pressure liquid chromatography to afford the title [(S,S) form] compound (3.33 g) and the [(R,R) form] compound (3.97 g), which is the antipode of the [(S,S) form] compound.

Separation conditions;
Column: CHIRALCEL OJ, 50Φ×500 mm, Daicel Chemical Industries, Ltd.
Eluant: hexane/2-propanol=1000/1
Flow rate: 25 ml per minute
The title [(S,S) form] compound:
Mass spectrum (CI, m/z): 222 (M$^+$+1) NMR spectrum CDCl$_3$, δppm): 0.20 (dt; J=8 Hz, 5 Hz, 1H), 0.48 (dt; J=8 Hz, 5 Hz, 1H), 0.66–0.80 (m, 1H), 0.82–0.91 (m, 1H), 0.98 (d; J=6 Hz, 3H), 2.01 (s, 3H), 3.76 (s, 3H), 4.21 (d; J=7 Hz, 2H), 6.76 (s, 1H). Optical rotation: $[\alpha]_D^{20}$=+17.6° (C=1.00, EtOH).

The antipode [(R,R) form] compound: Mass spectrum (CI, m/z): 222 (M$^+$+1) NMR spectrum (CDCl$_3$, δppm): 0.20 (dt; J=8 Hz, 5 Hz, 1H), 0.48 (dt; J=8 Hz, 5 Hz, 1H), 0.66–0.80 (m, 1H), 0.82–0.91 (m, 1H), 0.98 (d; J=6 Hz, 3H), 2.01 (s,3H),2.18 (s, 3H), 3.77 (s, 3H), 4.21 (d; J=7 Hz, 2H), 6.76 (s, 1H). Optical rotation: $[\alpha]_D^{20}$=−17.0° (C=1.01, EtOH).

(c) Methyl 3-formyl-4,5-dimethyl-1-[(1S 2S)-2-methylcyclopropylmethyl]pyrrole-2 -carboxylate Phosphorus oxychloride (2.15 g, 14 mmol) was added to a solution of dimethylformamide (1.10 g, 15 mmol) in toluene (2 ml) and the mixture was stirred at room temperature for 30 minutes. To this mixture was added a solution of methyl 4,5-dimethyl-1-[(1S,2S)-2-methylcyclopropylmethyl]pyrrole-2-carboxylate (2.21 g, 10 mmol) in toluene (6 ml) and the mixture was heated at 80° C. for 10 hours. After the reaction was completed, the reaction mixture was poured into water and neutralized with a saturated aqueous sodium hydrogencarbonate solution. The organic layer was separated, washed with a saturated aqueous sodium chloride solution, dried over anhydrous magnesium sulfate and then concentrated in vacuo. The residue was chromatographed on a column using ethyl acetate/hexane=10/1 as the eluant to afford the title compound (1.95 g, 78.2%) as a pale yellow oil.

Reference Example 3

7-(4-Fluorobenzyloxy)-2,3-dimethyl-1-1-[(1S,2S)-2-methylcyclopropylmethyl]pyrrolo[2.3-d]-pyridazine (a) 7-(4-Fluorobenzyloxy)-1-[(E)-2-methylcyclopropylmethyl]-2,3-dimethylpyrrolo[2,3-d]pyridazine (racemate)

A reaction was carried out in a similar manner to that described in Reference example 1 using (E)-2-methylcyclopropylmethyl bromide (racemate) instead of (1S,2S)-2-methylcyclopropylmethyl bromide to afford the desired compound (56%).

Mp: 120–122° C. Mass spectrum (CI, m/z): 340 (M$^+$+1) 1H-NMR spectrum CDCl$_3$, δppm): 0.14 (dt; J=8 Hz, 5 Hz, 1H), 0.39 (dt; J=8 Hz, 5 Hz, 1H), 0.59–0.65 (m, 1H), 0.76–0.85 (m, 1H), 0.89 (d; J=6 Hz, 3H), 2.26 (s, 3H), 2.36 (s, 3H), 4.13 (dd; J=15 Hz, 7 Hz, 1H), 4.27 (dd; J=15 Hz, 6 Hz, 1H), 5.63 (d; J=12 Hz, 1H), 5.68 (d; J=12 Hz, 1H), 7.05–7.12 (m, 2H), 7.47–7.52 (m, 2H), 8.96(s, 1H).

(b) 7-(4-Fluorobenzyloxy)-2,3-dimethyl-1-[(1S,2S)-2-methylcyclopropylmethyl]pyrrolo[2,3-d]pyridazine 7-(4-Fluorobenzyloxy)-1-[(E)-2-methylcyclopropylmethyl]-2,3-dimethylpyrrolo[2,3-d] pyridazine (racemate, 25 g) was chromatographed by high pressure liquid chromatography and recrystallized from ethyl acetate to afford the title [(S,S) form] compound (8.54 g) and the [(R,R) form] compound (7.60 g), which is the antipode of the [(S,S) form] compound.

Separation conditions;
Column: CHIRALCEL OJ, 50Φ×500 mm, Daicel Chemical Industries, Ltd.
Eluant: hexane/ethanol=90/10
Flow rate: 25 ml per minute
The title [(S,S) form] compound:
Mp: 114–115° C. Mass spectrum (CI, m/z): 340 (M$^+$+1) 1H-NMR spectrum (CDCl$_3$, δppm): 0.14 (dt; J=8 Hz, 5 Hz, 1H), 0.39 (dt; J=8 Hz, 5 Hz, 1H), 0.59–0.65 (m, 1H), 0.76–0.85 (m, 1H), 0.89 (d; J=6 Hz, 3H), 2.26 (s,3H), 2.36 (s, 3H), 4.13 (dd; J=15 Hz, 7 Hz, 1H), 4.27 (dd; J=15 Hz, 6 Hz, 1H), 5.63(d; J=12 Hz, 1H), 5.68 (d; J=12.2 Hz, 1H), 7.05–7.12 (m, 2H), 7.47–7.52 (m, 2H ), 8.96(s, 1H). Optical rotation: $[\alpha]_D^{20}$=+19.0° (C=0.99, MeOH).

The antipode [(R,R) form] compound:
Mp: 114–115° C. Mass spectrum (CI, m/z): 340 (M$^+$+1) NMR spectrum (CDCl$_3$, δppm): 0.15 (dt; J=8 Hz, 5 Hz, 1H), 0.39 (dt; J=8 Hz, 5 Hz, 1H), 0.58–0.66 (m, 1H), 0.78–0.85 (m, 1H), 0.89 (d; J=6 Hz, 3H), 2.26 (s, 3H), 2.37(s, 3H), 4.13

(dd; J=15 Hz, 7 Hz, 1H), 4.27 (dd; J=15 Hz, 6 Hz, 1H), 5.63 (d; J=12 Hz, 1H), 5.68 (d; J=12 Hz, 1H), 7.06–7.11 (m, 2H), 7.49–7.52 (m, 2H), 8.97 (s, 1H). Optical rotations: $[\alpha]_D^{20}$= 18.8° (C=0.98, MeOH).

Test Example 1

Test on Activity of Proton·potassium-adenosine Triphosphatase ($H^+.K^+$-ATPase)

A microsomal fraction prepared in accordance with the method of Sachs, et al. [J. Bio. Chem., 251, 7690(1976)] by homogenizing a fresh gastric mucosal layer of swine and then subjecting the homogenate to density gradient ultra centrifugation was employed as a proton potassium-adenosine triphosphatase preparation. A solution (10 $\mu$l) of a test compound dissolved in dimethyl sulfoxide was added to 0.75 ml of a 70 mM tris hydrochloric acid buffer (5 mM magnesium chloride, 20 mM potassium chloride, pH=6.85) containing 30 to 80 $\mu$g/ml, in terms of the protein concentration, of the enzyme preparation. The mixture was incubated with 200 times/min of agitation at 37° C. for 45 minutes. The enzymatic reaction was started by adding 0.25 ml of an 8 mM solution of disodium adenosine triphosphate. After this enzymatic reaction was continued for 20 minutes, 1 ml of a 10% trichloroacetic acid—activated charcoal (100 mg) solution was added to terminate the reaction. The reaction mixture was centrifuged (at 4° C. and 3000 rpm for 15 minutes). Inorganic phosphoric acid formed by the hydrolysis of adenosine triphosphate in the supernatant was subjected to colorimetry by the method of Yoda, et al. [Biochem. Biophys. Res. Commun., 40, 880(1970)]. The amount of inorganic phosphoric acid in a reaction mixture free from potassium chloride was also measured. By subtracting this amount from the amount of inorganic phosphoric acid in the presence of potassium chloride, protonpotassium-adenosine triphosphatase activity ($H^+.K^+$-ATPase) was determined. An inhibition ratio (%) was determined from the active value of the control and the active value of the test compound at each concentration, whereby a 50% inhibitory concentration ($IC_{50}$ $\mu$g/ml) against protonpotassium-adenosine triphosphatase was determined. As a result, the compound of Example 2 had a 50% inhibitory concentration ($IC_{50}$) of 0.015 $\mu$g/ml, exhibiting excellent activity.

Test Example 2

Test for Inhibition on Gastric Acid Secretion in Rats

After a group of rats was fasted overnight, they were subjected to midline abdominal incision and their pylorus was ligated under anesthesia with ether. The stomach and duodenum were returned to their original positions in the body, followed by closing at the abdominal incision part. A test compound (0.3 to 10 mg/ml) was suspended in an aqueous solution containing 0.5% of sodium carboxymethylcellulose and 0.4% of Tween 80 (trade mark). The resulting suspension (1 ml/kg of body weight) was orally administered to the rats through a stomach tube. Four hours after the ligation, the rats were sacrificed by inhalation of $CO_2$ gas. They were subjected to abdominal incision to remove their stomach. The content of the stomach was collected in a glass-made graduated centrifuge tube. After centrifugation, the amount (ml) of the supernatant and the amount (ml) of the precipitate were measured. The precipitate of the amount exceeding 0.5 ml was regarded as feces and excluded from the data. The supernatant (100 $\mu$g) was poured into a test tube. Distilled water (4 ml) was added to the solution, and the solution was titrated to pH 7.0 with 0.01 N sodium hydroxide. A standard acid concentration solution obtained by adding 4 ml of distilled water to 100 $\mu$l of 0.1 N hydrochloric acid was titrated in a similar manner. Each parameter was calculated in accordance with the following equations:

(1) Acid concentration of gastric juice (mEq/l)=A/B×100
 A: amount (ml) of sodium hydroxide required for titration of 100 $\mu$l of supernatant
 B: amount (ml) of sodium hydroxide required for titration of 100 $\mu$l of 0.1 N hydrochloric acid
(2) Gastric acid output (AO, $\mu$Eq/hr)=amount (ml) of supernatant of gastric juice×acid concentration of gastric juice (mEq/l)/4
(3) Inhibition ratio (%)=(C–D)/C×100
 C: AO ($\mu$Eq/hr) of vehicle-administered group
 D: AO ($\mu$Eq/hr) of test-compound-administered group
 A 50% inhibitory dose ($ID_{50}$) was determined from a dose-inhibition ratio curve on which an inhibition ratio at each dose versus logarithmic dose was drawn in accordance with the least squares. 95% confidence limit was determined according to Fieller's equation. As the results, the compound of Example 2 exhibited excellent activity, that is, an $ID_{50}$ less than 10 mg/kg.

Test Example 3

Antibacterial Action Against *Helicobacter Pylori*

The antibacterial activity of the compound of the invention was evaluated by using *Helicobacter pylori* strains 9470, 9472 and 9474 and determining MIC (Minimum Inhibitory Concentration) of the compound of the invention against *Helicobacter pylori*.

*Helicobacter pylori* was cultured by plating for 4 days. A medium was prepared by dissolving Brain Heart Infusion Agar (product of Difco Laboratories) in a prescribed amount of distilled water, sterilizing in an autoclave, adding equine blood (product of Nippon Seibutsu Zairyo) to give a concentration thereof of 7% and then solidifying the mixture.

Under microaerophilic conditions, *Helicobacter pylori* which had been cultured at 37° C. for 4 days was suspended in physiological saline to give its viable count of about $10^8$ CFU/ml. The suspension was then diluted to 100 times and a portion (about 10 $\mu$l) of the diluted suspension was inoculated in a medium for measuring MIC. The medium employed for measuring MIC has the same composition as the preculture medium. A compound of this invention was dissolved in dimethyl sulfoxide (DMSO) and two-fold serial dilutions were made with sterilized water. After mixing the solution and the medium in a ratio of 1:99, a solidified product in the Petri dish was employed as an MIC measuring medium. In a similar manner to that employed for the preculture, *Helicobacter pylori* was cultured at 37° C. for 3 days under microaerophilic conditions. After completion of the culturing, growth of the bacteria in the inoculated portion was visually observed. The minimum concentration of a compound of this invention at which no bacterial growth was observed was designated as MIC ($\mu$g/ml). The compound of Example 2 exhibited excellent antibacterial activity, that is, an MIC less than 12.5 $\mu$g/ml.

| Formulation Example 1 | |
|---|---|
| Tablets | |
| The compound of Example 2 | 30.0 mg |
| Lactose | 144.0 mg |
| Corn starch | 25.0 mg |
| Magnesium stearate | 1.0 mg |
| | 200.0 mg |

A tablet is prepared using the ingredients above. The components are blended and compressed by a tablet machine to form a tablet weighing 200 mg. The tablet may be coated if necessary, for example, to form a sugar-coated tablet.

The compounds of formula (I) or pharmaceutically acceptable salts thereof of this invention exhibit potent gastric acid secretion inhibition activity, gastric mucous membrane protection activity and potent antibacterial activity against *Helicobacter pylori* and they have excellent properties as medicaments. The compounds of formula (I) or pharmaceutically acceptable salts thereof are useful as a medicament, particularly for prevention or for therapeutic treatment for ulcerative diseases such as peptic ulcer, acute or chronic gastric ulcer, gastrisis, reflux esophagitis, gastroesophageal reflux disorder, dyspepsia, gastric hyperacidity or Zollinger-Ellison syndrome etc. and for administration for prevention or for treatment of bacterial infections arising from *Helicobacter pylori*.

What is claimed is:

1. A pyrrolopyridazine compound having the following formula or a pharmaceutically acceptable salt thereof:

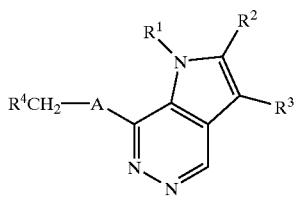

wherein:
$R^1$ is selected from the group consisting of $C_2$–$C_6$ alkenyl groups, halogeno $C_2$–$C_6$ alkenyl groups, $C_3$–$C_7$ cycloalkyl groups which may be optionally substituted with a $C_1$–$C_6$ alkyl group and $C_3$–$C_7$ cycloalkyl-$C_1$–$C_6$ alkyl groups which may be optionally substituted with a $C_1$–$C_6$ alkyl group;
$R^2$ represents a $C_1$–$C_6$ alkyl group;
$R^3$ is selected from the group consisting of hydroxymethyl groups, $C_2$–$C_6$ aliphatic acyloxymethyl groups, $C_6$–$C_{10}$ arylcarbonyloxymethyl groups which may be optionally substituted with substituents selected from the group consisting of $C_1$–$C_6$ alkyl groups, $C_1$–$C_6$ alkoxy groups and halogen atoms, $C_1$–$C_6$ alkoxycarbonyloxymethyl groups, formyl groups, carboxyl groups, $C_1$–$C_6$ alkoxycarbonyl groups and $C_6$–$C_{10}$ aryloxycarbonyl groups which may be optionally substituted with substituents selected from the group consisting of $C_1$–$C_6$ alkyl groups, $C_1$–$C_6$ alkoxy groups and halogen atoms;
$R^4$ represents a $C_6$–$C_{10}$ aryl group which may be optionally substituted with substituents selected from the group consisting of $C_1$–$C_6$ alkyl groups, halogeno $C_1$–$C_6$ alkyl groups, $C_1$–$C_6$ alkoxy groups, halogeno $C_1$–$C_6$ alkoxy groups and halogen atoms; and
A is selected from the group consisting of imino groups, oxygen atoms and sulfur atoms.

2. A pyrrolopyridazine compound or a pharmaceutically acceptable salt thereof according to claim 1, wherein $R^1$ is selected from the group consisting of $C_2$–$C_4$ alkenyl groups, $C_3$–$C_4$ alkenyl groups substituted with fluoro or chloro, $C_3$–$C_6$ cycloalkyl groups which may be optionally substituted with a $C_1$–$C_2$ alkyl group and $C_3$–$C_6$ cycloalkyl-$C_1$–$C_2$ alkyl groups which may be optionally substituted with a $C_1$–$C_2$ alkyl group.

3. A pyrrolopyridazine compound or a pharmaceutically acceptable salt thereof according to claim 1, wherein $R^1$ is selected from the group consisting of $C_3$–$C_4$ alkenyl groups, 3-chloro-2-propenyl groups, 3,3-difluoro-2-propenyl groups, 3,3-dichloro-2-propenyl groups, cyclopropyl groups, 2-methylcyclopropyl groups, 2-ethylcyclopropyl groups, cyclobutyl groups, cyclopentyl groups, 2-methylcyclopentyl groups, cyclohexyl groups, 2-methylcyclohexyl groups, cyclopropylmethyl groups, 2-methylcyclopropylmethyl groups, 2-ethylcyclopropylmethyl groups, cyclobutylmethyl groups, 2-methylcyclobutylmethyl groups, cyclopentylmethyl groups and 2-methylcyclohexylmethyl groups.

4. A pyrrolopyridazine compound or a pharmaceutically acceptable salt thereof according to claim 1, wherein $R^1$ is selected from the group consisting of 2-propenyl groups, 2-butenyl groups, cyclopropyl groups, 2-methylcyclopropyl groups, cyclopentyl groups, 2-methylcyclopentyl groups, cyclohexyl groups, 2-methylcyclohexyl groups, cyclopropylmethyl groups, 2-methylcyclopropylmethyl groups, cyclopentylmethyl groups and 2-methylcyclohexylmethyl groups.

5. A pyrrolopyridazine compound or a pharmaceutically acceptable salt thereof according to claim 1, wherein $R^1$ is selected from the group consisting of 2-propenyl groups, 2-butenyl groups, cyclopropyl groups, 2-methylcyclopropyl groups, cyclopropylmethyl groups and 2-methylcyclopropylmethyl groups.

6. A pyrrolopyridazine compound or a pharmaceutically acceptable salt thereof according to claim 1, wherein $R^1$ is selected from the group consisting of 2-butenyl groups, cyclopropylmethyl groups and 2-methylcyclopropylmethyl groups.

7. A pyrrolopyridazine compound or a pharmaceutically acceptable salt thereof according to claim 1, wherein $R^2$ is a $C_1$–$C_4$ alkyl group.

8. A pyrrolopyridazine compound or a pharmaceutically acceptable salt thereof according to claim 1, wherein $R^2$ is a $C_1$–$C_2$ alkyl group.

9. A pyrrolopyridazine compound or a pharmaceutically acceptable salt thereof according to claim 1, wherein $R^2$ is a methyl group.

10. A pyrrolopyridazine compound or a pharmaceutically acceptable salt thereof according to claim 1, wherein $R^3$ is selected from the group consisting of hydroxymethyl groups, $C_2$–$C_6$ aliphatic acyloxymethyl groups, benzoyloxymethyl groups which may be optionally substituted with a substituent selected from the group consisting of methyl groups, methoxy groups, fluoro and chloro, $C_1$–$C_4$ alkoxycarbonyloxymethyl groups, formyl groups, carboxyl groups, $C_1$–$C_4$ alkoxycarbonyl groups and phenyloxycarbonyl groups which may be optionally substituted with a substituent selected from the group consisting of methyl groups, methoxy groups, fluoro and chloro.

11. A pyrrolopyridazine compound or a pharmaceutically acceptable salt thereof according to claim 1, wherein $R^3$ is selected from the group consisting of hydroxymethyl groups, $C_2$–$C_6$ aliphatic acyloxymethyl groups, benzoyloxymethyl groups, $C_1$–$C_2$ alkoxycarbonyloxymethyl groups, formyl groups, carboxyl groups, $C_1$–$C_2$ alkoxycarbonyl groups and phenyloxycarbonyl groups.

12. A pyrrolopyridazine compound or a pharmaceutically acceptable salt thereof according to claim 1, wherein $R^3$ is selected from the group consisting of hydroxymethyl groups, $C_2$–$C_4$ aliphatic acyloxymethyl groups, $C_1$–$C_2$ alkoxycarbonyloxymethyl groups, formyl groups, carboxyl groups and $C_1$–$C_2$ alkoxycarbonyl groups.

13. A pyrrolopyridazine compound or a pharmaceutically acceptable salt thereof according to claim 1, wherein $R^3$ is selected from the group consisting of hydroxymethyl groups, $C_2$–$C_3$ aliphatic acyloxymethyl groups, formyl groups and carboxyl groups.

14. A pyrrolopyridazine compound or a pharmaceutically acceptable salt thereof according to claim 1, wherein $R^3$ is a hydroxymethyl group or an acetoxymethyl group.

15. A pyrrolopyridazine compound or a pharmaceutically acceptable salt thereof according to claim 1, wherein $R^4$ is a phenyl group which is substituted with 1 to 3 substituents selected from the group consisting of $C_1$–$C_4$ alkyl groups, halogeno $C_1$–$C_4$ alkyl groups, $C_1$–$C_4$ alkoxy groups, halogeno $C_1$–$C_4$ alkoxy groups, fluoro, chloro and bromo.

16. A pyrrolopyridazine compound or a pharmaceutically acceptable salt thereof according to claim 1, wherein $R^4$ is a phenyl group which is substituted with 1 to 3 substituents selected from the group consisting of a methyl group, a trifluoromethyl group, a methoxy group, a trifluoromethoxy groups, a difluoromethoxy group, fluoro, chloro and bromo.

17. A pyrrolopyridazine compound or a pharmaceutically acceptable salt thereof according to claim 1, wherein $R^4$ is a phenyl group which is substituted at the position(s) selected from the group consisting of 2-, 4- and 6-position of the phenyl group with 1 or 2 substituents selected from the group consisting of fluoro and chloro.

18. A pyrrolopyridazine compound or a pharmaceutically acceptable salt thereof according to claim 1, wherein $R^4$ is a phenyl group which is substituted at the 4-position, 2,4-positions or 2,6-positions of the phenyl group with 1 or 2 substituents selected from the group consisting of fluoro and chloro.

19. A pyrrolopyridazine compound or a pharmaceutically acceptable salt thereof according to claim 1, wherein A is an oxygen atom or a sulfur atom.

20. A pyrrolopyridazine compound or a pharmaceutically acceptable salt thereof according to claim 1, wherein A is an oxygen atom.

21. A pyrrolopyridazine compound or a pharmaceutically acceptable salt thereof according to claim 1, wherein:
$R^1$ is selected from the group consisting of $C_2$–$C_4$ alkenyl groups, $C_3$–$C_4$ alkenyl groups substituted with fluoro or chloro, $C_3$–$C_6$ cycloalkyl groups which may be optionally substituted with a $C_1$–$C_2$ alkyl group and $C_3$–$C_6$ cycloalkyl-$C_1$–$C_2$ alkyl groups which may be optionally substituted with a $C_1$–$C_2$ alkyl group;
$R^2$ is a $C_1$–$C_4$ alkyl group;
$R^3$ is selected from the group consisting of hydroxymethyl groups, $C_2$–$C_6$ aliphatic acyloxymethyl groups, benzoyloxymethyl groups which may be optionally substituted with a substituent selected from the group consisting of methyl groups, methoxy groups, fluoro and chloro, $C_1$–$C_4$ alkoxycarbonyloxymethyl groups, formyl groups, carboxyl groups, $C_1$–$C_4$ alkoxycarbonyl groups and phenyloxycarbonyl groups which may be optionally substituted with a substituent selected from the group consisting of methyl groups, methoxy groups, fluoro and chloro;
$R^4$ is a phenyl group which is substituted with 1 to 3 substituents selected from the group consisting of $C_1$–$C_4$ alkyl, halogeno $C_1$–$C_4$ alkyl, $C_1$–$C_4$ alkoxy, halogeno-$C_1$–$C_4$ alkoxy, fluoro, chloro and bromo; and
A is an oxygen atom or a sufur atom.

22. A pyrrolopyridazine compound or a pharmaceutically acceptable salt thereof according to claim 1, wherein:
$R^1$ is selected from the group consisting of $C_3$–$C_4$ alkenyl groups, 3-chloro-2-propenyl groups, 3,3-difluoro-2-propenyl groups, 3,3-dichloro-2-propenyl groups, cyclopropyl groups, 2-methylcyclpropyl groups, 2-ethylcyclopropyl groups, cyclobutyl groups, cyclopentyl groups, 2-methylcyclopentyl groups, cyclohexyl groups, 2-methylcyclohexyl groups, cyclopropylmethyl groups, 2-methylcyclopropylmethyl groups, 2-ethylcyclopropylmethyl groups, cyclobutylmethyl groups, 2-methylcyclobutylmethyl groups, cyclopentylmethyl groups and 2-methylcyclohexylmethyl groups;
$R^2$ is a $C_1$–$C_4$ alkyl group;
$R^3$ is selected from the group consisting of hydroxymethyl groups, $C_2$–$C_6$ aliphatic acyloxymethyl groups, benzoyloxymethyl groups, $C_1$–$C_2$ alkoxycarbonyloxymethyl groups, formyl groups, carboxyl groups, $C_1$–$C_2$ alkoxycarbonyl groups and phenyloxycarbonyl groups;
$R^4$ is a phenyl group which is substituted with 1 to 3 substituents selected from the group consisting of methyl groups, trifluoromethyl groups, methoxy groups, trifluoromethoxy groups, difluoromethoxy groups, fluoro, chloro and bromo; and
A is an oxygen atom or a sulfur atom.

23. A pyrrolopyridazine compound or a pharmaceutically acceptable salt thereof according to claim 1, wherein:
$R^1$ is selected from the group consisting of 2-propenyl groups, 2-butenyl groups, cyclopropyl groups, 2-methylcyclopropyl groups, cyclopentyl groups, 2-methylcyclopentyl groups, cyclohexyl groups, 2-methylcyclohexyl groups, cyclopropylmethyl groups, 2-methylcyclopropylmethyl groups, cyclopentylmethyl groups and 2-methylcyclohexylmethyl groups;
$R^2$ is a $C_1$–$C_2$ alkyl group;
$R^3$ is selected from the group consisting of hydroxymethyl groups, $C_2$–$C_4$ aliphatic acyloxymethyl groups, $C_1$–$C_2$ alkoxycarbonyloxymethyl groups, formyl groups, carboxyl groups and $C_1$–$C_2$ alkoxycarbonyl groups;
$R^4$ is a phenyl group which is substituted at the position(s) selected from the group consisting of 2-, 4- and 6-position of the phenyl group with 1 or 2 substituents selected from the group consisting of fluoro and chloro; and
A is an oxygen atom.

24. A pyrrolopyridazine compound or a pharmaceutically acceptable salt thereof according to claim 1, wherein:
$R^1$ is selected from the group consisting of 2-propenyl groups, 2-butenyl groups, cyclopropyl groups, 2-methylcyclopropyl groups, cyclopropylmethyl groups and 2-methylcyclopropylmethyl groups,
$R^2$ is a $C_1$–$C_2$ alkyl group;

$R^3$ is selected from the group consisting of hydroxymethyl groups, $C_2$–$C_3$ aliphatic acyloxymethyl groups, formyl groups and carboxyl groups;

$R^4$ is a phenyl group which is substituted at the position(s) selected from the group consisting of 2-, 4- and 6-position of the phenyl group with 1 or 2 substituents selected from the group consisting of fluoro and chloro; and A is an oxygen atom.

25. A pyrrolopyridazine compound or a pharmaceutically acceptable salt thereof according to claim 1, wherein:

$R^1$ is selected from the group consisting of 2-butenyl groups, cyclopropylmethyl groups and 2-methylcyclopropylmethyl groups;

$R^2$ is a methyl group;

$R^3$ is a hydroxymethyl group or an acetoxymethyl group;

$R^4$ is a phenyl group which is substituted at the 4-position, 2,4-positions or, 2,6-positions of the phenyl group with 1 or 2 substituents selected from the group consisting of fluoro and chloro; and A is an oxygen atom.

26. A pyrrolopyridazine compound selected from the following group or a pharmaceutically acceptable salt thereof:

1-(2-butenyl)-7-(4-fluorobenzyloxy)-3-hydroxymethyl-2-methylpyrrolo[2,3-d]pyridazine, 7-(4-fluorobenzyloxy)-3-hydroxymethyl-2-methyl-1-(2-methylcyclopropylmethyl)pyrrolo[2,3-d]pyridazine, 1-(2-butenyl)-7-(2,4-difluorobenzyloxy)-3-hydroxymethyl-2-methylpyrrolo[2,3-d]pyridazine, 7-(2,4-difluorobenzyloxy)-3-hydroxymethyl-2-methyl-1-(2-methylcyclopropylmethyl)pyrrolo[2,3-d]pyridazine, 3-acetoxymethyl-7-(4-fluorobenzyloxy)-2-methyl-1-(2-methylcyclopropylmethyl)pyrrolo[2,3-d]pyridazine, and 3-acetoxymethyl-7-(2,4-difluorobenzyloxy)-2-methyl-1-(2-methylcyclopropylmethyl)pyrrolo[2,3-d]pyridazine.

27. A pyrrolopyridazine compound according to claim 26.

28. A pyrrolopyridazine compound or a pharmaceutically acceptable salt thereof according to claim 1, which is 3-acetoxymethyl-7-(4-fluorobenzyloxy)-2-methyl-1-[(1S,2S)-2-methylcyclopropylmethyl]pyrrolo[2,3-d]pyridazine or a pharmaceutically acceptable salt thereof.

29. A pyrrolopyridazine compound according to claim 28.

30. A pyrrolopyridazine compound or a pharmaceutically acceptable salt thereof according to claim 1, which is 7-(4-fluorobenzyloxy)-3-hydroxymethyl-2-methyl-1-[(1S,2S)-2-methylcyclopropylmethyl]pyrrolo[2,3-d]pyridazine or a pharmaceutically acceptable salt thereof.

31. A pyrrolopyridazine compound according to claim 30.

32. A pyrrolopyridazine compound or a pharmaceutically acceptable salt thereof according to claim 1, which is 7-(4-fluorobenzyloxy)-3-formyl-2-methyl-1-[(1S,2S)-2-methylcyclopropylmethyl]pyrrolo[2,3-d]pyridazine or a pharmaceutically acceptable salt thereof.

33. A pyrrolopyridazine compound according to claim 32.

34. A pyrrolopyridazine compound or a pharmaceutically acceptable salt thereof according to claim 1, which is 3-carboxy-7-(4-fluorobenzyloxy)-2-methyl-1-[(1S,2S)-2-methylcyclopropylmethyl]pyrrolo[2,3-d]pyridazine or a pharmaceutically acceptable salt thereof.

35. A pyrrolopyridazine compound according to claim 34.

36. A pharmaceutical composition comprising (i) a pharmacologically acceptable carrier and (ii) a pyrrolopyridazine compound or a pharmaceutically acceptable salt thereof according to any one of claims 1 to 35.

37. A method for the prophylaxis or treatment of an ulcerative disease which comprises administering to a warm-blooded animal in need thereof a pharmaceutically effective amount of a pyrrolopyridazine compound or a pharmaceutically acceptable salt thereof according to anyone of claims 1 to 35.

38. A method for the prophylaxis or treatment of an ulcerative disease which comprises administering to a human in need thereof a pharmaceutically effective amount of a pyrrolopyridazine compound or a pharmaceutically acceptable salt thereof according to anyone of claims 1 to 35.

39. A method for the treatment of a *Helicobacter pylori* infection in a warm-blooded animal which comprises administering to said warm-blooded animal a pharmaceutically effective amount of a pyrrolopyridazine compound or a pharmaceutically acceptable salt thereof according to anyone of claims 1 to 20.

40. A method for the treatment of a *Helicobacter pylori* infection in a human which comprises administering to said human a pharmaceutically effective amount of a pyrrolopyridazine compound or a pharmaceutically acceptable salt thereof according to anyone of claims 21 to 35.

* * * * *